(12) United States Patent
Taylor et al.

(10) Patent No.: US 8,178,294 B2
(45) Date of Patent: May 15, 2012

(54) METHOD OF HAPLOTYPE-BASED GENETIC ANALYSIS FOR DETERMINING RISK FOR DEVELOPING INSULIN RESISTANCE, CORONARY ARTERY DISEASE AND OTHER PHENOTYPES

(75) Inventors: Kent D. Taylor, Ventura, CA (US); Jerome I. Rotter, Los Angeles, CA (US); Huiying Yang, Hockessin, DE (US); Willa A. Hsueh, Pacific Palisades, CA (US); Xiuqing Guo, Santa Monica, CA (US); Leslie J. Raffel, Los Angeles, CA (US); Mark O. Goodarzi, Los Angeles, CA (US); Yii-Der Ida Chen, Saratoga, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 550 days.

(21) Appl. No.: 11/564,243

(22) Filed: Nov. 28, 2006

(65) Prior Publication Data

US 2008/0032291 A1 Feb. 7, 2008

Related U.S. Application Data

(63) Continuation-in-part of application No. 10/463,301, filed on Jun. 16, 2003, now Pat. No. 7,141,373.

(60) Provisional application No. 60/388,726, filed on Jun. 14, 2002.

(51) Int. Cl.
C12Q 1/68 (2006.01)
C12P 19/34 (2006.01)

(52) U.S. Cl. ........................................ 435/6.1; 435/91.2
(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,988,617 A | 1/1991 | Landegren | |
| 5,384,242 A | 1/1995 | Oakes | |
| 6,297,014 B1 | 10/2001 | Rotter et al. | |
| 6,869,766 B2 | 3/2005 | Reue et al. | |
| 7,135,303 B2 | 11/2006 | Levine | |
| 7,141,373 B2 | 11/2006 | Rotter et al. | |
| 2002/0106657 A1 | 8/2002 | Rotter et al. | |
| 2003/0065139 A1 | 4/2003 | Rosen et al. | |
| 2003/0224418 A1 | 12/2003 | Braun et al. | |
| 2004/0030110 A1 | 2/2004 | Guo et al. | |
| 2004/0072170 A1 | 4/2004 | Bunk et al. | |
| 2004/0192583 A1 | 9/2004 | Medicherla et al. | |
| 2005/0272054 A1* | 12/2005 | Cargill et al. | 435/6 |
| 2006/0019896 A1 | 1/2006 | Li et al. | |
| 2006/0173629 A1 | 8/2006 | Poynard | |

FOREIGN PATENT DOCUMENTS

| | | |
|---|---|---|
| EP | 1228241 | 1/2001 |
| EP | 1408121 | 4/2008 |
| WO | WO 01/02606 | 1/2001 |
| WO | WO 02/008425 | 1/2002 |
| WO | WO 02/36820 | 5/2002 |
| WO | WO 03/106652 | 12/2003 |
| WO | WO 2008/121788 | 10/2008 |
| WO | WO 2008/121802 | 10/2008 |
| WO | WO 2009/052418 | 4/2009 |
| WO | WO 2009/055596 | 4/2009 |
| WO | WO 2011/116244 | 9/2011 |

OTHER PUBLICATIONS

NCBI SNP FAQs 'Data Changes that Occur Between Builds', from www.ncbi.nlm.nih.gov accessed on Oct. 28, 2008, pritned pp. 1-3.*
Hacker UT et al. Gut (May 1997) vol. 40 No. 5, pp. 623-627.*
Abecasis, GR, et al., "A General Test of Association for Quantitative Traits in Nuclear Families," Am J Hum Genet 66:279-292 (2000).
Abecasis, GR, et al., "Pedigree Tests of Transmission Disequilibrium," Eur J Hum Genet 8:545-551 (2000).
Ahn, YI, et al., "Association of Lipoprotein Lipase Gene Variation With the Physiological Components of the Insulin-Resistance Syndrome in the Population of the San Luis Valley, Colorado," Diabetes Care 16:1502-1506 (1993).
Ahn, YI, et al., "Two DNA Polymorphisms in the Lipoprotein Lipase Gene and Their Associations with Factors Related to Cardiovascular Disease," J Lipid Res 34:421-428 (1993).
Allayee, H, et al., "Genome Scan for Blood Pressure in Dutch Dyslipidemic Families Reveals Linkage to a Locus on Chromosome 4p," Hypertension 38:773-778 (2001).
Allison, DB., "Transmission-Disequilibrium Tests for Quantitative Traits," Am J Hum Genet 60:676-690 (1997).
Anderson, J.L., et al., "Association of Lipoprotein Lipase Gene Polymorphisms With Coronary Artery Disease," J Amer Collge Cardio 33:1013-1020 (1999).
Aoki, T, et al., "Triglyceride Lowering Effect of Pitavastatin in a Guinea Pig Model of Postprandial Lipemia," Arzneim.-Forsch./Drug Res. 53:154-158 (2003).
Babaev, VR, et al., "Macrophage Lipoprotein Lipase Promotes Foam Cell Formation and Atherosclerosis in Low Density Lipoprotein Receptor-Deficient Mice," J Biol Chem 275:26293-26299 (2000).
Barrett, JC, et al., "Haploview: Analysis and Visualization of LD and Haplotype Maps," Bioinformatics 21:263-265 (2005).
Bergman, RN, et al., "Minimal Model-Based Insulin Sensitivity has Greater Heritability and Different Genetic Basis than Homeostasis Model Assessment or Fasting Insulin," Diabetes 52:2168-2174 (2003).

(Continued)

*Primary Examiner* — Stephen Kapushoc
(74) *Attorney, Agent, or Firm* — Sean D. Senn; Davis Wright Tremaine LLP

(57) ABSTRACT

Disclosed is a method for determining haplotypes useful for large-scale genetic analysis, within a genomic reference sequence of interest, for a human subpopulation. The method can applied to statistically evaluating the genotypes of subjects for any statistically significant association with a phenotype of interest, such as insulin resistance or coronary artery disease. Thus, also disclosed are a method of detecting a genetic predisposition in a human subject for certain biological conditions, which may be related to coronary artery disease.

3 Claims, 6 Drawing Sheets

OTHER PUBLICATIONS

Bey, L, et al., "Induction of Lipoprotein Lipase Gene Expression in 3T3-L1 Preadipocytes by Atorvastatin, a Cholesterol- and Triglyceride-Lowering Drug," Pharmacology 66:51-56 (2002).

Boden, G, et al., "Effects of Acute Changes of Plasma Free Fatty Acids on Intramyocellular Fat Content and Insulin Resistance in Healthy Subjects," Diabetes 50:1612-1617 (2001).

Cabezas, MC, et al., "Simvastatin Improves Chylomicron Remnant Removal in Familial Combined Hyperlipidemia Without Changing Chylomicron Conversion," Metabolism 42: 497-503 (1993).

Castellani, LW, et al., "Mechanisms Mediating Insulin Resistance in Transgenic Mice Overexpressing Mouse Apolipoprotein A-II," J Lipid Res 45:2377-2387 (2004).

Castellani, LW, et al., "Overexpression of Apolipoprotein AII in Transgenic Mice Converts High Density Lipoproteins to Proinflammatory Particles," J Clin Invest 100:464-474 (1997).

Chasman, DI, et al., "Pharmacogenetic Study of Statin Therapy and Cholesterol Reduction," JAMA 291:2821-2827 (2004).

Clark, AG, et al., "Haplotype Structure and Population Genetic Inferences from Nucleotide-Sequence Variation in Human Lipoprotein Lipase," Am J Hum. Genet 63:595-612 (1998).

Cole, SA, et al., "Association of a PvuII RFLP at the Lipoprotein Lipase Locus with Fasting Insulin Levels in Hispanic Men," Genet Epidemiol 10:177-188 (1993).

Daly, MJ, et al., "High-Resolution Haplotype Structure in the Human Genome," Nat Genet 29:229-232 (2001).

Defronzo, RA, et al., "Glucose Clamp Technique: a Method for Quantifying Insulin Secretion and Resistance," Am J Physiol 237(3):E214-E223 (1979).

Despres, JP, et al., "Hyperinsulinemia as an Independent Risk Factor for Ischemic Heart Disease," N Engl J Med 334:952-7 (1996).

Eisenberg, S., "High Density Lipoprotein Metabolism," J Lipid Res 25:1017-1058 (1984).

Elston, RC, et al., "Haseman and Elston Revisited," Genet Epidemiol 19:1-17 (2000).

Endo, K, et al., "Atorvastatin and Pravastatin Elevated Pre-Heparin Lipoprotein Lipase Mass of Type 2 Diabetes with Hypercholesterolemia," J Atheroscler Thromb 11:341-347 (2004).

Felsenstein, I., "PHYLIP—Phylogeny Inference Package (version 3.2)," Cladistics 5:164-166 (1989).

Freeman, MS, et al., "Heritability of Features of the Insulin Resistance Syndrome in a Community-Based Study of Healthy Families," Diabet Med 19:994-9 (2002).

Gabriel, SB, et al., "The Structure of Haplotype Blocks in the Human Genome," Science 296:2225-2229 (2002).

Gagne, E, et al., "Analysis of DNA Changes in the LPL Gene in Patients with Familial Combined Hyperlipidemia," Arterioscler Thromb 14:1250-1257 (1994).

Gaziano, JM, et al., "Fasting Triglycerides, High-Density Lipoprotein, and Risk of Myocardial Infarction," Circulation 96:2520-2525 (1997).

Goodarzi, MO, et al., "Lipoprotein Lipase is a Gene for Insulin Resistance in Mexican Americans," Diabetes 53:214-220 (2004).

Goodarzi, MO, et al., "Determination and Use of Haplotypes: Ethnic Comparison and Association of the Lipoprotein Lipase Gene and Coronary Artery Disease in Mexican-Americans," Genet Med 5:322-327 (2003).

Goodarzi, MO, et al., "Haplotypes in the Lipoprotein Gene Influence High-Density Lipoprotein Cholesterol Response to Statin Therapy and Progression of Atherosclerosis in Coronary Artery Bypass Grafts," Pharmacogenomics J Advance Online Publication 1-8 (2006).

Goodarzi, MO, et al., "The 3' Untranslated Region of the Lipoprotein Lipase Gene: Haplotype Structure and Association with Post-Heparin Plasma Lipase Activity," J Clin Endocrinol Metab 90:4816-4823 (2005).

Groenemeijer, BE, et al.. "Genetic Variant Showing a Positive Interaction with β-Blocking Agents with a Beneficial Influence on Lipoprotein Lipase Activity, HDL Cholesterol, and Triglyceride Levels in Coronary Artery Disease Patients. The Ser447-Stop Substitution in the Lipoprotein Lipase Gene," Circulation 95:2628-2635 (1997).

Guerre-Millo, M., "Adipose Tissue Hormones," J Endocrinol Invest 25:855-861 (2002).

Haffner, SM, et al., "Upper Body and Centralized Adiposity in Mexican Americans and Non-Hispanic Whites: Relationship to Body Mass Index and Other Behavioral and Demographic Variables," Int J Obes 10:493-502 (1986).

Hanley, AJ, et al., "Homeostasis Model Assessment of Insulin Resistance in Relation to the Incidence of Cardiovascular Disease: the San Antonio Heart Study," Diabetes Care 25:1177-1184 (2002).

Haseman, JK, et al., "The Investigation of Linkage Between a Quantitative Trait and a Marker Locus," Behav Genet 2:3-19 (1972).

Heizmann, C, et al., "DNA Polymorphism Haplotypes of the Human Lipoprotein Lipase Gene: Possible Association with High Density Lipoprotein Levels," Hum Genet 86:578-584 (1991).

Henkin, L, et al., "Genetic Epidemiology of Insulin Resistance and Visceral Adiposity: The IRAS Family Study Design and Methods," Ann Epidemiol 13:211-217 (2003).

Hensley, LL, et al., "Transgenic Mice Expressing Lipoprotein Lipase in Adipose Tissue. Absence of the Proximal 3'-Untranslated Region Causes Translational Upregulation," J Biol Chem 278:32702-32709 (2003).

Herbert, V, et al., "Coated Charcoal Immunoassay of Insulin," J Clin Endocrinol 25:1375-1384 (1965).

Hirschhorn, JN, et al., "A Comprehensive Review of Genetic Association Studies," Genet Med 4:45-61 (2002).

Hofacker, IL., "Vienna RNA Secondary Structure Server," Nucleic Acids Res 31:3429-3431 (2003).

Hokanson, JE, et al., "Pleiotropy and Heterogeneity in the Expression of Atherogenic Lipoproteins: The IRAS Family Study," Hum Hered 55:46-50 (2003).

Holmer, SR, et al., "Lipoprotein Lipase Gene Polymorphism, Cholesterol Subfractions and Myocardial Infarction in Large Samples of the General Population," Cardiovasc Res 47:806-812 (2000).

Hong, Y, et al., "Genetic and Environmental Architecture of the Features of the Insulin-Resistance Syndrome," Am J Hum Genet 60:143-52 (1997).

Humphries, SE, et al., "Lipoprotein Lipase Gene Variation is Associated with a Paternal History of Premature Coronary Artery Disease and Fasting and Postprandial Plasma Triglycerides: the European Atherosclerosis Research Study (EARS)," Arterioscler Thromb Vasc Biol 18:526-534 (1998).

Jemaa, R, et al., "Lipoprotein Lipase Gene Polymorphisms: Associations with Hypertriglyceridemia and Body Mass Index in Obese People," Int J Obes 19:270-274 (1995).

Jukema, JW, et al., "The Asp9 Asn Mutation in the Lipoprotein Lipase Gene is Associated with Increased Progression of Coronary Atherosclerosis," Circulation 94:1913-1918 (1996).

Kasim, SE, et al., "Mechanisms of Triglyceride-Lowering Effect of an HMG-CoA Reductase Inhibitor in a Hypertriglyceridemic Animal Model, The Zucker Obese Rat," J Lipid Res 33:1-7 (1992).

Kobayashi, J, et al., "Effect of Atorvastatin Treatment on Lipoprotein Lipase Mass in the Pre-Heparin Plasma in Japanese Hyperlipidemic Subjects," Clin Chim Acta 314:261-264 (2001).

Kolterman, OG, et al., "Mechanisms of Insulin Resistance in Human Obesity: Evidence for Receptor and Postreceptor Defects," J Clin Invest 65:1272-1284 (1980).

Kozaki, K, et al., "Mutational Analysis of Human Lipoprotein Lipase by Carboxy-Terminal Truncation," J Lipid Res 34:1765-1772 (1993).

Lee, WJ, et al., "Associations Between Lipoprotein Lipase Gene Polymorphisms and Insulin Resistance in Coronary Heart Disease," Chin Med J (Taipei) 63:563-572 (2000).

Lewontin, RC., "The Interaction of Selection and Linkage. I. General Considerations; Heterotic Models," Genetics 49:49-67 (1964).

Livak, KJ., "Allelic Discrimination Using Fluorogenic Probes and the 5' Nuclease Assay," Genet Anal 14:143-149 (1999).

Malloy, MJ, et al., "A Risk Factor for Atherosclerosis: Triglyceride-Rich Lipoproteins," Adv Intern Med 47:111-136 (2001).

Mamputu, JC, et al., "Lipoprotein Lipase Enhances Human Monocyte Adhesion to Aortic Endothelial Cells," J Lipid Res 38:1722-1729 (1997).

Mamputu, JC, et al., "Proliferative Effect of Lipoprotein Lipase on Human Vascular Smooth Muscle Cells," Arterioscler Thromb Vasc Biol 20:2212-2219 (2000).

Matthews, DR, et al., "Homeostasis Model Assessment: Insulin Resistance and β-Cell Function from Fasting Plasma Glucose and Insulin Concentrations in Man," Diabetologia 28:412-419 (1985).
Mattu, RK, et al., "DNA Variants at the LPL Gene Locus Associate with Angiographically Defined Severity of Atherosclerosis and Serum Lipoprotein Levels in a Welsh Population," Arterioscler Thromb 14:1090-1097 (1994).
Mead, JR, et al., "The Pivotal Role of Lipoprotein Lipase in Atherosclerosis," Cardiovasc Res 55:261-269 (2002).
Mitchell, BD, et al., "Genetic Analysis of the IRS. Pleiotropic Effects of Genes Influencing Insulin Levels on Lipoprotein and Obesity Measures," Arterioscler Thromb Vasc Bio 16:281-288 (1996).
Motulsky, AG, et al., "Genetics of Coronary Atherosclerosis," The Genetic Basis of Common Diseases, 2nd ed. New York, Oxford University Press, Inc., 105-126 (2002).
Murthy, V, et al., "Molecular Pathobiology of the Human Lipoprotein Lipase Gene," Pharmacol Ther 70:101-135 (1996).
Neel, JV, et al., "Type II Diabetes, Essential Hypertension, and Obesity as 'Syndromes of Impaired Genetic Homeostasis': the 'Thrifty Genotype' Hypothesis Enters the 21st Century," Perspect Biol Med 42:44-74 (1998).
Nickerson, DA, et al., "DNA Sequence Diversity in a 9.7-kb Region of the Human Lipoprotein Lipase Gene," Nat Genet 19:233-240 (1998).
Nicklas, BJ, et al., "Lipoprotein Lipase Gene Variation is Associated with Adipose Tissue Lipoprotein Lipase Activity, and Lipoprotein Lipid and Glucose Concentrations in Overweight Postmenopausal Women," Hum Genet 106:420-424 (2000).
Nilsson-Ehle, et al., "A Stable, Radioactive Substrate Emulsion for Assay of Lipoprotein Lipase," J Lipid Res 17:536-541 (1976).
Norris, JM, et al., "Quantitative Trait Loci for Abdominal Fat and BMI in Hispanic-Americans and African-Americans: the IRAS Family Study," Int J Obes (Lond) 29:67-77 (2005).
O'Connell, JR, et al., "PedCheck: A Program for Identification of Genotype Incompatibilities in Linkage Analysis," Am J Hum Genet 63:259-266 (1998).
Okosun, IS, et al., "Abdominal Adiposity and Clustering of Multiple Metabolic Syndrome in White, Black and Hispanic Americans," Ann Epidemiol 10:263-270 (2000).
Pacini, G, et al., "MINMOD: A Computer Program to Calculate Insulin Sensitivity and Pancreatic Responsivity from the Frequently Sampled Intravenous Glucose Tolerance Test," Comput Methods & Programs in Biomed 23:113-122 (1986).
Park, YW, et al., "The Metabolic Syndrome: Prevalence and Associated Risk Factor Findings in the US Population from the Third National Health and Nutrition Examination Survey, 1988-1994," Arch Intern Med 163:427-436 (2003).
Peacock, RE, et al., "Associations Between Lipoprotein Lipase Gene Polymorphisms and Plasma Correlations of Lipids, Lipoproteins and Lipase Activities in Young Myocardial Infarction Survivors and Age-Matched Healthy Individuals from Sweden," Atherosclerosis 97:171-185 (1992).
Pesole, G, et al., "UTRdb and UTRsite: Specialized Databases of Sequences and Functional Elements of 5' and 3' Untranslated Regions of Eukaryotic mRNAs," Nucleic Acids Res 30:335-340 (2000). Update 2002.
Phillips, DIW, et al., "Intramuscular Triglyceride and Muscle Insulin Sensitivity: Evidence for a Relationship in Nondiabetic Subjects," Metabolism 45:947-950 (1996).
Preiss-Landl, K, et al., "Lipoprotein Lipase: The Regulation of Tissue Specific Expression and its Role in Lipid and Energy Metabolism," Curr Opin Lipidol 13:471-481 (2002).
Proenza, AM, et al., "Association of Sets of Alleles of Genes Encoding β3-Adrenoreceptor, Uncoupling Protein 1 and Lipoprotein Lipase with Increased Risk of Metabolic Complications in Obesity," Int J Obes 24:93-100 (2000).
Pulawa, LK, et al., "Overexpression of Muscle Lipoprotein Lipase and Insulin Sensitivity," Curr Opin Clin Nutr Metab Care 5:569-574 (2002).
Pyorala, M, et al., "Hyperinsulinemia Predicts Coronary Heart Disease Risk in Healthy Middle-Aged Men: The 22-Year Follow-Up Results of the Helsinki Policemen Study," Circulation 98:398-404 (1998).

Qin, ZS, et al., "Partition-Ligation-Expectation-Maximization Algorithm for Haplotype Inference with Single-Nucleotide Polymorphisms," Am J Hum Genet 71:1242-1247 (2002).
Quinones, MJ, et al., "Coronary Vasomotor Abnormalities in Insulin-Resistant Individuals," Ann Intern Med 140:700-708 (2004).
Ranganathan, G, et al., "The Translational Regulation of Lipoprotein Lipase in Diabetic Rats Involves the 3'-Untranslated Region of the Lipoprotein Lipase mRNA," J Biol Chem 275:40986-40991 (2000).
Ranganathan, G, et al., "Translational Regulation of Lipoprotein Lipase by Epinephrine Involves a Trans-Acting Binding Protein Interacting with the 3' Untranslated Region," J Biol Chem 272:2515-2519 (1997).
Rioux, JD, et al., "Genetic Variation in the 5q31 Cytokine Gene Cluster Confers Susceptibility to Crohn Disease," Nat Genet 29:223-228 (2001).
Samuels, ME, et al., "Identification of a Common Variant in the Lipoprotein Lipase Gene in a Large Utah Kindred Ascertained for Coronary Heart Disease: The 93G/D9N Variant Predisposes to Low HDL-C/high Triglycerides," Clin Genet 59:88-98 (2001).
Sasaki, J, et al., "Effects of Fluvastatin, a New Inhibitor of HMG-CoA Reductase, and Niceritrol on Serum Lipids, Lipoproteins and Cholesterol Ester Transfer Activity in Primary Hypercholesterolemic Patients," Int J Clin Pharmacol Ther 33:420-426 (1995).
Sato, A, et al., "Effect of Simvastatin (MK-733) on Plasma Triacylglycerol Levels in Rats," Biochem Pharmacol 41:1163-1172 (1991).
Schneider, JG, et al., "Atorvastatin Improves Diabetic Dyslipidemia and Increases Lipoprotein Lipase Activity in Vivo," Atherosclerosis 175:325-331 (2004).
Sobel, E, et al., "Descent Graphs in Pedigree Analysis: Applications to Haplotyping, Location Scores, and Marker-Sharing Statistics," Am J Hum Genet 58:1323-1337 (1996).
Spielman, RS, et al., "Transmission Test for Linkage Disequilibrium: The Insulin Gene Region and Insulin-Dependent Diabetes Mellitus (IDDM)," Am J Hum Genet 52:506-516 (1993).
Taylor, KD, et al., "Lipoprotein Lipase Locus and Progression of Atherosclerosis in Coronary-Artery Bypass Grafts," Genet Med 6:481-486 (2004).
Templeton, AR, et al., "Recombinational and Mutational Hotspots Within the Human Lipoprotein Lipase Gene," Am J Hum Genet 66:69-83 (2000).
Templeton, AR, et al., "A Cladistic Analysis of Phenotype Associations with Haplotypes Inferred From Restriction Endonuclease Mapping. II. The Analysis of Natural Populations," Genetics 120:1145-1154 (1988).
Templeton, AR, et al., "Cladistic Structure Within the Human Lipoprotein Lipase Gene and Its Implications for Phenotypic Association Studies," Genetics 156:1259-1275 (2000).
Templeton, AR., "Cladistic Approaches to Identifying Determinants of Variability in Multifactorial Phenotypes and the Evolutionary Significance of Variation in the Human Genome," CIBA Found Symp 197:259-283 (1996).
The Post Coronary Artery Bypass Graft Trial Investigators, "The Effect of Aggressive Lowering of Low-Density Lipoprotein Cholesterol Levels and Low-Dose Anticoagulation on Obstructive Changes in Saphenous-Vein Coronary-Artery Bypass Grafts," N Engl J Med 336:153-162 (1997).
Ukkola, O, et al., "Genetic Variation at the Lipoprotein Lipase Locus and Plasma Lipoprotein and Insulin Levels in the Quebec Family Study," Atherosclerosis 158:199-206 (2001).
Wagenknecht, LE, et al., "The Insulin Resistance Atherosclerosis Study (IRAS) Objectives, Design, and Recruitment Results," Ann Epidemiol 5:464-472 (1995).
Wallace, TM, et al., "The Assessment of Insulin Resistance in Man," Diabet Med 19:527-534 (2002).
Wang, N, et al., "Distribution of Recombination Crossovers and the Origin of Haplotype Blocks: The Interplay of Population History, Recombination, and Mutation," Am J Hum Genet 71:1227-1234 (2002).
Wu, DA, et al., "Quantitative Trait Locus Mapping of Human Blood Pressure to a Genetic Region at or Near the Lipoprotein Lipase Gene Locus on Chromosome 8p22," J Clin Invest 97:2111-2118 (1996).

Yost, TJ, et al., "Change in Skeletal Muscle Lipoprotein Lipase Activity in Response to Insulin/Glucose in Non-Insulin-Dependent Diabetes Mellitus," Metabolism 44:786-790 (1995).

Zechner, R, et al., "The Structure of the Mouse Lipoprotein Lipase Gene: a B1 Repetitive Element is Inserted into the 3' Untranslated Region of the mRNA," Genomics 11:62-76 (1991).

Zeger, SL, et al., "Longitudinal Data Analysis for Discrete and Continuous Outcomes," Biometrics 42:121-130 (1986).

Zhang, H, et al., "Common Sequence Variants of Lipoprotein Lipase: Standardized Studies of In Vitro Expression and Catalytic Function," Biochim Biophys Acta 1302:159-166 (1996).

AC093684, Homo sapiens BAC clone RP11-681B22 from 2, complete sequence. NCBI Entrez Nucleotide. Sep. 7, 2001.

Alegret et al., Effect of hypolipidemic drugs on key enzyme activities related to lipid metabolism in normolipidemic rabbits, European Journal of Pharmacology, (Apr. 1998); vol. 347, pp. 283-291.

Anguita et al.. Comparison of the effectiveness of lovastatin therapy for hypercholesterolemia after heart transplantation between patients with and without pretransplant atherosclerotic coronary artery diseases, Am. J. Cardiol., (Oct. 15, 1994); vol. 74(8), pp. 776-779. Abstract Only.

Alvan, Gunnar, Editorial, Genetic polymorphisms in drug metabolism, Journal of Internal Medicine, (1992), vol. 231, pp. 571-573.

Ballantyne, C. M., Low-density lipoproteins and risk for coronary artery disease, The American Journal of Cardiology, (Nov. 5, 1998); vol. 82(9A), pp. 3Q-12Q.

Bell, D. S., A comparison of lovastatin, an HMG-CoA reductase inhibitor, with gemfibrozi, a fibrinic acid derivative, in the treatment of patients with diabetic dyslipidemia, Clinical Therapy, (1995); vol. 17(5), 901-910 Abstract Only.

Bellosta et al., HMG-CoA reductase inhibitors reduce MMP-9 secretion by macrophages, Arterioscler Thromb Vasc Biol., (Nov. 1998); vol. 18(11), pp. 1671-1678, Abstract Only.

Butowski et al., Usual care dietary practice, achievement and implications for medication in the management of hypercholesterolaemia. Data from the U.K. Lipid Clinics Programme., Eur. Heart J., (1998), vol. 19(9), pp. 1328-1333 Abstract Only.

Campeau et al.. The relation of risk factors to the development of atherosclerosis in saphenous-vein bypass grafts and the progression of disease in the native circulation, The New England Journal of Medicine, (Nov. 22, 1984); vol. 311, No. 21, pp. 1329-1332.

Campeau et al., The effect of aggressive lowering of low-density lipoprotein cholesterol levels and low-dose anticoagulation on obstructive changes in saphenous-vein coronary-artery bypass grafts, The New England Journal of Medicine, (Jan. 16, 1997), vol. 336, No. 3, pp. 153-162.

Cannon, C. P., Advances in the medical management of acute coronary syndromes, Curr. Opin. Cardiol., (Sep. 1998), vol. 13(5), pp. 327-347, Abstract Only.

Chamberlain et al,, DNA polymorphisms at the lipoprotein lipase gene: associations in normal and hypertriglyceridaemic subjects, Atherosclerosis, (Sep. 1989), vol. 79(1), pp. 85-91.

Chen et al., HindIII, DNA polymorphism in the lipoprotein lipase gene and plasma lipid phenotypes and carotid artery atherosclerosis, Hum. Genet., (Nov. 1996), vol. 98(5), pp. 551-556, Abstract Only.

Chuat et al., The lipoprotein lipase-encoding human gene: sequence from intron-6 to intron-9 and presence in intron-7 of a 40-million-year-old Alu sequence, Gene, (1992); vol. 11(2), pp. 257-261.

Christians et al., Metabolism and drug interactions of 3-hydroxy-3-methylglutaryl coenzyme, a reductase inhibitors in transplant patients: are the statins mechanistically similar?, Pharmacol. Ther., (1980), vol. 80. No. 1, pp. 1-34.

Deeb et al., Structure of the Human Lipoprotein Lipase Gene, Biochemistry, (May 16, 1989); vol. 28, No. 10, pp. 4131-4135.

Deeb et al., Hepatic lipase and dyslipidemia: interactions among genetic variants, obesity, gender and diet, J. Lipid. Res.,(2003); vol. 44, pp. 1279-1286.

Durrington, P. N., Can we afford to treat hyperlipidaemia as we should?, Strategies for rational treatment, Atherosclerosis, (Sep. 1998); 139 Suppl 1:S1-5, Abstract Only.

Farmer et al., Currently available hypolipidaemic drugs and future therapeutic developments, Baillieres Clin. Endocrine Metab., (Oct. 1995); 9(4):825-847, Abstract Only.

Farmer et al., Choosing the right lipid-regulating agent, A guide to selection, Drugs, (Nov. 1996); 52(5):649:661.

Farmer, J. A., Economic implications of lipid-lowering trials: current considerations i selecting a statin, Am. J. Cardiol., (Sep. 24, 1998); 82(6A):26M-31M.

Farmer, J. A., Aggressive lipid therapy in the statin era, Prog. Cardiovasc. Dis., (Sep.-Oct. 1998); 41(2):71-94.

Farnier et al., Current and future treatment of hyperlipidemia: the role of statins, Am. J. Cardiol., (Aug. 27, 1998); 82(4B):3J-10J.

Fisher et al, Common variation in the lipoprotein lipase gene: effects on plasma lipids and risk of atherosclerosis, Atherosclerosis(Dec. 1997); 35(2):145-59, Abstract Only.

Funke et al, The low down on lipoprotein lipase, Nature Genetics, (May 1995); vol. 10, pp. 6-7.

Garg et al., Lovastatin for lowering cholesterol levels in non-insulin-dependent diabetes mellitus, N. Engl. J. Med., (Jan. 1988); 318(2):81-86.

GenBank Accession No. X52978 (Nov. 1992).

GenBank Accession No. AF050163 (Sep. 1998).

GenBank Accession No. M76722 (Jan. 1995).

Gerdes et al., Polymorphisms in the lipoprotein lipase gene and their associations with plasma lipid concentrations in 40-year-old Danish men, Circulation, (Oct. 1995); 92(7):1765-1769, Abstract Only.

Georges et al., Family study of lipoprotein lipase gene polymorphisms and plasma triglyceride levels, Genet. Epidemiol., (1996); 13(2):179-92.

Glock et al., Allelic Ladder Characterization of the Short tandem Repeat Polymorphism in Intron 6 of the Lipoprotein Lipase Gene and Its Application in an Austrian Caucasian Population Study, Journal of Forensic Sciences, (Jul. 1996); JFSCA, vol. 41, No. 4, pp. 579-581.

Goodarzi et al., Lipin-1 genetic variation may influence liver function and inflammation in hispanic americans, The American Society of Human Genetics, 58th Annual Meeting, Nov. 2008.

Goodarzi et al., Haplotypes in the lipoprotein lipase gene influence fasting insulin and discovery of a new risk haplotype, The Journal of Clinical Endocrinology & Metabolism, (Jan. 2007), vol. 92, pp. 293-296.

Goodarzi et al., Haplotypes in the lipoprotein lipase gene influence high-density lipoprotein cholesterol response to statin therapy and progression of atherosclerosis in coronary artery bypass grafts, Pharmacogenics Journal, (2007), vol. 7, pp. 66-73.

Goldberg et al., Comparison of the effects of lovastatin and gemfibrozil on lipids and glucose control in non-insulin-dependent diabetes mellitus, Am. J. Cardiol, (Sep. 18, 1990); 66:16B-21B.

Gotoda et al., Detection of three separate DNA polymorphisms in the human lipoprotein lipase gene by gene amplification and restriction endonuclease digestion, Journal of Lipid Research, (1992); vol. 33, pp. 1067-1072.

Guo et al., Heterogeneity of genetic relationship between c-reactive protein and insulin resistance measures, The American Society of Human Genetics, 58th Annual Meeting, Nov. 2008.

Guo et al., Evidence of linkage and association between the lipoprotein lipase gene (LPL) and insulin resistance in Hispanic hypertension families, 52nd Annual Meeting of the American Society of Human Genetics; Baltimore, MD, USA, (Oct. 15-19, 2002), Abstract Only.

Guo et al., Genetic variants in the lipoprotein lipase gene are confirmed to be associated with liver enzyme levels in hispanic americans, The American Society of Human Genetics, 58th Annual Meeting, Nov. 2008.

Guyton et al., Effectiveness of once-nightly dosing of extended-release niac 1n alone and in combination for hypercholesterolemia, Am. J. Cardiol., (Sep. 15, 1998).

Gylling et al., Treatment of lipid disorders in non-insulin-dependent diabetes mellitus, Curr. Opin. Lipidol., (Dec. 1997); 8:342-7.

Hallman et al., Analysis of lipoprotein lipase haploytypes reveals associations not apparent from analysis of contstituen loci, American Journal of Human Genetics, (1998), vol. 63, pp. 499-510.

Hansson et al., Effects of intensive blood-pressure lowering and low-dose aspirin in patients with hypertension: principal results of the Hypertension Optimal Treatment (hot) randomised trial, HOT Study Group, Lancet, (Jun. 13, 1998); 351:1755-62.

Hayden et al., Molecular genetics of human lipoprotein lipase deficiency, *Mol. Cell. Biochem.*, (Aug. 18, 1992); 113(2):171-176.

Huse et al., Cost-effectiveness of statins, *Am. J. Cardiol.*, (Dec. 1, 1998); 82(11):1357-63, Abstract Only.

Kirchgessner et al., The sequence of cDNA Encoding Lipoprotein Lipase, *The Journal of Biological Chemistry*, (Jun. 25, 1987); vol. 262, No. 18, pp. 8463-8466, Abstract Only.

Kirchgessner et al., Organization of the human lipoprotein lipase gene and evolution of the lipase gene family, *Proc. Natl. Acad. Sci. USA*, (Dec. 1989); vol. 86, No. 24, pp. 9647-9651.

Kleyn et al., Genetic Variation as a Guide to Drug Development, *Science*, (Sep. 18, 1998); vol. 281, pp. 1820-1821.

Kornitzer, M., Primary and secondary prevention of coronary artery disease: a follow-up on clinical controlled trials, *Curr. Opin. Lipidol.*, (Dec. 1998), 9(6):557-64, Abstract Only.

Kuivenhoven et al., The role of a Common Variant of the Cholesteryl Ester Transfer Protein Gene in the Progression of Coronary Atherosclerosis, *The New England Journal of Medicine*, (Jan. 8, 1998); vol. 338. No. 2., pp. 86-93.

Larosa, J. C., The role of diet and excercise in the statin era, *Progressive Cardiovascular Disease*, (Sep.-Oct. 1998); 41(2):137-50.

Levenson et al., Nonisotopically labeled probes and primers, PCR Protocols: A guide to methods and applications, pp. 99-112, 1990.

Lopez-Capape et al., Frequency of the metabolic syndrome in obese spanish pediatric population, *Eur. J. Endocrinol.*, (Aug. 2006), vol. 155, pp. 309-313.

Mahaney et al., A major locus influencing plasma high-density lipoprotein cholesterol levels in the san antonio family heart study, *Arteriosclerosis, Thrombosis and Vascular Biology*, (1995), vol. 15, pp. 1730-1739, Abstract Only.

McKenney, J. M., Lovastatin: a new cholesterol-lowering agent, *Clin. Pharm.*, (Jan. 1988); 7(1):21-36, Abstract Only.

Minnich et al., Lipoprotein lipase gene mutations in coronary artery disease, *Can. J. Cardiol.*, (May 1998); 14(5):711-6, Abstract Only.

Mitchell et al., DNA polymorphisms at the lipoprotein lipase gene and their association with quantitative variation in plasma high-density lipoproteins and triacylgycerides, *Hum. Biol.*, (Jun. 1994); 66(3):383-97, Abstract Only.

Mori et al., Development of a direct DNA sequencing method for detecting heterozygous mutations of the human lipoprotein lipase gene, *Clin. Biochem.*, (Jun. 1997); 30(4):315-324, Abstract Only.

Neitzel et al., Atherosclerosis in Aortocoronary Bypass Grafts, Morphologic Study and Risk Factor Analysis 6 to 12 Years After Surgery, *Arteriosclerosis*, (Nov./Dec. 1986); vol. 6, No. 6, pp. 594-600.

Oka et al., Structure and polymorphic map of human lipoprotein lipase gene, *Biochimica et Biophysica Acta*, (1990); vol. 1049, pp. 21-26.

Okosun et al., Abdominal adiposity and clustering of multiple metabolic syndrome in White, Black and Hispanic Americans. *Ann. Epidemiol.*, (2000); 10.263-70.

Olsson, A. G., Addressing the challenge, *Eur. Heart J.*, (Oct. 1998); 19 Supp M:M29-35.

Onai et al., Effects of simvastatin on glucose metabolism in non-insulin dependent diabetic patients—The influence of LPL gene Hind III polymorphism, *Journal of the Japan Diabetes Society*, (1999); vol. 42, No. 8, pp. 673-678, Abstract Only.

PaulWeber et al., Molecular basis of lipoprotein lipase deficiency in two Austrian families with type 1 hyperlipoproteinemia, *Atherosclerosis*, (1991); vol. 86, pp. 239-250.

Pedersen et al.. Benefits and risks of HMG-CoA reductase inhibitors in the prevention of coronary heart disease: a reappraisal, *Drug Saf.*, (Jan. 1996); 14(1):11-24, Abstract Only.

Pitsavos et al., Effects of pravastatin on thoracic aortic atherosclerosis in patients with heterozygous familial hypercholesterolemia, *Am J Cardiol*, (Dec. 15, 1998); 82(12):1484-8, Abstract Only.

Reymer et al., A lipoprotein lipase mutation (Asn291Ser) is associated with reduced HDL cholesterol levels in premature atherosclerosis, *Nature Genetics*, (May 1995); 10:28-34.

Rifkind, B. M., Clinical trials of reducing low-density lipoprotein concentrations, *Endocrinol. Metab. Clin. North Am.*, (Sep. 1998); 27(3):585-95, viii-ix, Abstract Only.

Rudski et al, Systemic immune reactions to HMG-CoA reductase inhibitors. Report of 4 cases and review of the literature, *Medicine* (Baltimore), (1998); 77(6):378-83, Abstract Only.

Santamarina-Fojo et al., Structure, function and role of lipoprotein lipase in lipoprotein metabolism, *Current Opinion in Lipidology*, (1994); vol. 5, pp. 117-125.

Sass et al., Evidence for a cholesterol-lowering gene in a French-Canadian kindred with familial hypercholesterolemia, *Hum. Genet.*, (Jul. 1995); 96:21-26.

Scheen, A. J., Drug clinics. Drug of the month. Atorvastatin, *Rev Med Liege*, (Jun. 1998); 53(6):374-7, Abstract Only.

Schoonjans et al., 3-Hydroxy-3-methylglutaryl CoA reductase inhibitors reduce serum triglyceride levels through modulation of apolipoprotein CIII and lipoprotein lipase, *FEBS* Letters, vol. 452 (1999); pp. 160-164.

Sing K et al., Lipoprotein lipase gene 1-11 mutations plasma lipid levels, progression/regression of coronary atherosclerosis response to therapy and future clinical events. Lipoproteins and Coronary Atherosclerosis Study, *Atherosclerosis*, (Jun. 1999); 144(2):435-442.

Stratagene Catalog, Gene Characterization Kits, p. 39, (1988).

Stephen et al., Frequency and Allelic Association of Common Variants in the Lipoprotein Lipase Gene in Different Ethnic Groups: the Wandsworth Heart and Stroke Study, *Genetic Epidemiology*, (Mar. 17, 2000); vol. 18, No. 3, pp. 203-216.

Szucs T. D., Pharmaco-economic aspects of lipid-lowering therapy: is it worth the price?, *Eur. Heart J.*, (Oct. 1998); 19 Suppl M:M22-8, Abstract Only.

Takagi et al., Identification of two new alleles at the lipoprotein lipase (LPL) short tandem repeat (STR) locus results in seven polymorphic alleles in the Japanese population: allele frequency data in comparison with Caucasian populations, *Molecular and Cellular Probes*, (1996); vol. 10, pp. 227-228.

Tikkanen et al., Treatment of familial and non-familial hypercholesterolaemia: a review of HMG-CoA reductase inhibitors and probucol, *Eur. Heart J.*, (Aug. 1987); 8 Suppl E: 97-101. Abstract Only.

The Medical Research Council's Practice Research Framework, Thrombosis prevention trial: randomised trial of low-intensity oral anticoagulation with warfarin and low-dose aspirin in the primary prevention of ischaemic heart disease in men at increased risk, *Lancet*, (Jan. 24, 1998), 351:233-41.

Vesell, Elliot S., Therapeutic Lessons from Pharmacogenetics, *Annals of Internal Medicine*, (Apr. 15, 1997); vol. 126, No. 8.

Von Keutz et al., Preclinical safety evaluation of cerivastatin, a novel HMG-CoA reductase inhibitor, *Am. J. Cardiol.*,(Aug. 27, 1998); 82(4B):11J-17J, Abstract Only.

Weinshilboum, Richard, Methyltransferase pharmacogenetics, *Pharmac. Ther.*, (1989); vol. 43, pp. 77-90.

Wheeler, D. C., Are there potential non-lipid-lowering uses of statins?, *Drugs*, (Oct. 1998); 56(4):517-22, Abstract Only.

Wion et al., Human Lipoprotein Lipase complementary DNA Sequence, *Science*, (Mar. 27, 1987); vol. 235, pp. 1638-1641.

Zuliani et al. Tetranucleotide repeat polymorphism in the LPL gene, *Nucleic Acids Research* (Aug. 25, 1990); 18(16), p. 4958.

EP00945124.6 Examination Report dated Jul. 26, 2002.
EP00945124.6 Examination Report dated Sep. 19, 2002.
EP03028652.0 Search Report dated May 7, 2007.
EP03028652.0 Examination Report dated Feb. 18, 2009.
EP03742027.0 Search Report dated Jul. 12, 2006.
PCT/US2000/18308 Search Report dated Apr. 2, 2002.
PCT/US2000/18308 Written Opinion dated Apr. 23, 2002.
PCT/US2000/18308 IPRP dated Jun. 26, 2002.
PCT/US2003/019050 Search Report dated Jan. 15, 2004.
PCT/US2003/019050 Written Opinion Dec. 6, 2004.
PCT/US2003/019050 IPRP dated Apr. 7, 2005.
PCT/US2008/058605 Search Report dated Sep. 12, 2008.
PCT/US2008/058605 IPRP dated Oct. 6, 2009.
PCT/US2008/058623 Search Report dated Sep. 24, 2008.
PCT/US2008/058623 IPRP dated Oct. 8, 2009.
PCT/US2008/080359 Search Report dated Jan. 8, 2009.
PCT/US2008/080359 IPRP dated Apr. 20, 2010.
PCT/US2008/080996 Search Report dated Apr. 20, 2009.
PCT/US2008/080996 IPRP dated Apr. 27, 2010.

PCT/US2009/062835 IPRP dated May 3, 2011.
U.S. Appl. No. 09/347,114 Office Action mailed May 5, 2000.
U.S. Appl. No. 09/347,114 Notice of Allowance mailed Feb. 26, 2001.
U.S. Appl. No. 09/898,779 Office Action mailed Jan. 25, 2002.
U.S. Appl. No. 09/898,779 Office Action dated Jun. 6, 2002.
U.S. Appl. No. 10/463,301 Office Action dated Feb. 23, 2006.
U.S. Appl. No. 10/463,301 Notice of Allowance dated Jul. 28, 2006.
U.S. Appl. No. 12/594,143 Restriction Requirement dated Jul. 26, 2011.

* cited by examiner

3' UTR – haplotype 19-1     3' UTR – haplotype 19-4

METHOD OF HAPLOTYPE-BASED GENETIC ANALYSIS FOR DETERMINING RISK FOR DEVELOPING INSULIN RESISTANCE, CORONARY ARTERY DISEASE AND OTHER PHENOTYPES

This application is a Continuation-in-Part of U.S. patent application Ser. No. 10/463,301, filed Jun. 16, 2003 now U.S. Pat. No. 7,141,373 and which claims the benefit of U.S. provisional application 60/388,726, filed Jun. 14, 2002. Both of these applications are incorporated herein by reference in their entirety.

The present invention was made with government support under NIH grant numbers HL-28481, HL-60030, HL-60894, HL-60919, HL-60944, HL-61019, HL-67974, and HL-69757 and NRSA Training Grant 5 T32 GM08243-16. The U.S. government may have certain rights in this invention.

BACKGROUND OF THE INVENTION

1. Field of the Invention

The present invention relates to the field of medical genetics.

2. Discussion of the Related Art

Currently there is much interest in the use of haplotype data in the genetics of common disease. Investigators are faced with the considerable challenge of how many and which variants to genotype in a given candidate gene for haplotype determination. Gabriel et al. sequenced 13 megabases across the genome in subjects from Africa, Europe, and Asia. They showed that the human genome is organized in haplotype blocks (most of which are longer than 10 kb), with three to five commonly occurring (>5%) haplotypes per block. Only six to eight variants were sufficient to define the most common haplotypes in each block. The challenge is how to select these variants efficiently and affordably. In the protocol described here, the first stage is to genotype a number of variants that span a genomic region of interest. This is performed in a subset of the study population to minimize costs. These data are then used to determine the haplotypes in that region. The most frequently occurring haplotypes are then identified, and only those SNPs that are necessary to define these haplotypes (typically six or fewer such haplotypes) are then genotyped on large scale, yielding the most common haplotypes in a population for association analysis. The availability of family data assists this approach by facilitating unambiguous determination of haplotypes.

The insulin resistance syndrome (also called the metabolic syndrome) is a clustering of factors associated with an increased risk of coronary artery disease (CAD). The syndrome affects over 20% of adults in the United States, with the highest age specific prevalence rates in Mexican-Americans. Insulin resistance, whether or not it is accompanied by other features of the metabolic syndrome, has been associated with an increased risk of cardiovascular events and death.

There is evidence in the Framingham offspring study that three factors or syndrome clusters, underlie the clustering of basic risk variables that form the insulin resistance syndrome: a diabetic predisposing syndrome characterized by impaired glucose tolerance, a cardiovascular metabolic syndrome, and a hypertension syndrome. Numerous lines of evidence from epidemiological studies support the idea that these factors occur many years prior to the onset of overt coronary artery disease.

The clustering of insulin resistance, hypertension, central obesity, and dyslipidemia in the metabolic syndrome is receiving much attention as a risk factor for cardiovascular disease. The central component of this syndrome, insulin resistance, has been found to increase cardiovascular risk. In the San Antonio Heart Study, insulin resistance, estimated by homeostatic model assessment (HOMA), was an independent predictor of incident cardiovascular events over 8 years of follow-up. In the Helsinki Policemen Study, 970 men free of diabetes or CAD at baseline were followed for 22 years; those with the highest levels of insulin resistance as estimated by insulin area under the curve during oral glucose tolerance testing had the highest rates of CAD events and death. High fasting insulin concentrations were an independent predictor of ischemic heart disease events among 2103 non-diabetic Canadian men. A genetic basis for the components of the insulin resistance syndrome has been demonstrated by familial aggregation. For this reason, investigators have asked the question as to whether genetic determinants of insulin resistance also influence the other components of the metabolic syndrome.

As an example, lipoprotein lipase (LPL) plays a major role in lipid metabolism. Located on capillary endothelium, LPL hydrolyzes triglycerides of chylomicrons and very low density lipoproteins, generating free fatty acids and monoacylglycerol. Complete deficiency of LPL results in the familial chylomicronemia syndrome. Because LPL activity affects the concentration of triglycerides, an important cardiovascular risk factor, LPL has been studied as a candidate gene for atherosclerosis. Several studies have identified linkage and association of the LPL gene with hypertension, indirect or surrogate measurements of insulin resistance, dyslipidemia, obesity, and atherosclerosis. LPL is an excellent candidate connecting insulin resistance to atherosclerosis because it controls the delivery of free fatty acids (FFA) to muscle, adipose tissue, and vascular wall macrophages, wherein lipid uptake influences peripheral insulin sensitivity, central obesity, and foam cell formation.

Wu et al. demonstrated linkage of the LPL locus to systolic blood pressure in non diabetic relatives of Taiwanese subjects with type 2 diabetes. The HindIII polymorphism in intron 8 of the LPL gene has been associated with measurements of insulin resistance in normoglycemic Caucasian and Hispanic subjects and Chinese subjects. The Ser447Stop polymorphism has been found to be associated with decreased atherosclerosis risk. Both the HindIII and Ser447Stop polymorphisms are in the 3' end of the LPL gene, downstream of a recombination hotspot.

The LPL gene has emerged as a candidate gene for features of metabolic syndrome, including insulin resistance. LPL hydrolyzes triglycerides carried in chylomicrons and very low density lipoproteins, the rate-limiting step in delivery of free fatty acids (FFA) to muscle and adipose tissue. By controlling the delivery of FFA to muscle, LPL may affect insulin sensitivity by influencing levels of intramyocellular lipid, which correlate with muscle insulin resistance. Also, LPL may influence insulin resistance by affecting FFA delivery to visceral adipose tissue, which is increasingly viewed as an endocrine organ, capable of secreting mediators of insulin resistance. LPL action also regulates the plasma triglyceride concentration, an important atherosclerosis risk factor. LPL activity indirectly raises HDL-cholesterol levels because LPL-mediated hydrolysis of VLDL provides surface components that merge with HDL3 to form HDL2 particles. LPL-mediated delivery of FFA and lipoprotein remnants to vessel wall macrophages plays a role in foam cell formation, an early event in the development of atherosclerotic plaque. Thus, functional variation in LPL may impact both insulin resistance and atherosclerosis.

Most studies that have reported association of the LPL gene with insulin resistance used only surrogate measurements of insulin resistance, including fasting glucose, fasting insulin, and insulin area under the curve (AUC) during oral glucose tolerance testing (OGTT). One study evaluated the steady state plasma glucose during the insulin suppression test. In addition, all except one of these studies only examined association of the intronic restriction fragment length polymorphisms PvuII and HindIII. Thus, current evidence that variation in LPL plays a role in insulin sensitivity has been indirect. Assessment of glucose infusion rate (GINF) during the euglycemic hyperinsulinemic clamp study is widely regarded as the most direct physiologic measurement of insulin sensitivity. An analysis of indices of insulin sensitivity in the Insulin Resistance Atherosclerosis Study showed that direct physiologic measurements of insulin sensitivity have a higher heritability than measures based on fasting values (such as HOMA). Thus, use of physiologic indices rather than simple fasting indices should provide more power to discover genes that contribute to insulin sensitivity.

While various polymorphisms in the 3' end of LPL, such as HindIII, have been associated with surrogate measures of insulin resistance and with atherosclerosis, published reports of positive linkage or association of variation in LPL with indices of insulin sensitivity have typically examined only one or two single nucleotide polymorphisms. However, a haplotype-based analysis recently demonstrated an association of LPL 3' end haplotypes with coronary artery disease in Mexican-Americans.

Published studies reporting association of the LPL gene with insulin resistance used only single variants, usually HindIII or PvuII. In some cases, the results are in conflict; studies have reported the T allele of HindIII associated with insulin resistance, others report the G allele associated with insulin resistance, and others show no association of HindIII with insulin resistance. This demonstrates a limitation of the common approach of examining one or two polymorphisms per candidate gene in an association study.

With the sequencing of the human genome it has become apparent that variation in individuals is quite extensive. There is increasing evidence that this variation is best described by groups of associated polymorphisms referred to as haplotypes.

Recent studies suggest that the extensive variation in human beings is best described by groups of associated polymorphisms referred to as haplotypes. Haplotypes encompass chromosomal blocks that have remained unbroken by recombination during the population evolutionary history of the gene. Haplotypes are more likely to identify disease associations than single polymorphisms because they reflect global gene structure and encompass the majority of common variation in a gene. Identification of a haplotype associated with increased or decreased disease risk should facilitate identification of the actual functional variant that affects disease risk, because this variant should lie on chromosome regions identified by that haplotype.

Thus, haplotypes capture the majority of common variation in a gene; consequently, the use of haplotypes is more likely to identify disease-variation associations than is the use of a random single polymorphism. Identification of a haplotype associated with increased or decreased disease risk should facilitate identification of the actual functional variant that affects disease risk, because this variant should lie on chromosomes identified by that haplotype. Genotyping to determine haplotype structure and frequencies is required for this type of analysis. A major challenge is determination and selection of the polymorphisms that will be used to determine haplotypes in a given population.

Currently there is much interest in the use of haplotype data in the genetics of common diseases, such as coronary artery disease and insulin resistance. Investigators are faced with the considerable challenge of how many and which variants or markers to genotype in a given candidate gene for haplotype determination. Gabriel et al. sequenced 13 megabases across the genome in subjects from Africa, Europe, and Asia; it was shown that the human genome is organized in haplotype blocks (most of which are longer than 10 kilobases), with three to five commonly occurring (>5%) haplotypes per block. Only six to eight variants were sufficient to define the most common haplotypes in each block. There is a need for a way to select these variants, or markers, efficiently and affordably.

Accordingly, the present invention provides such a method of selecting useful haplotypes, as well particular haplotypes useful for predicting predisposition to insulin resistance in humans, including Hispanics. These and other benefits are described hereinbelow.

SUMMARY OF THE INVENTION

The present invention relates to a method for determining haplotypes useful for application to large-scale genetic analysis and screening tests for a human population or subpopulation, such as Mexican-Americans, within a genomic reference sequence of interest. The method involves detecting the presence of a plurality of genetic markers, or variants, at positions of the genomic reference sequence, in the genotypes of a first number of subjects in the human subpopulation. A frequency hierarchy of the detected markers is identified, and from the frequency hierarchy a set of haplotypes is constructed, each haplotype of the set comprising at least one of the most frequently detected markers. A smaller subset of the set of haplotypes is selected, the smaller subset comprising those haplotypes most frequently occurring in the first number of subjects. The markers needed to define the thus selected smaller subset of the set of haplotypes is identified.

In some embodiments of the present invention, useful in determining genetic associations between specific haplotypes and particular phenotypes, a second number of subjects in the human subpopulation are genotyped for the markers previously identified in accordance with the method; the second number of subjects being larger than the first number of subjects. The genotypes of the second number of subjects are evaluated for any statistically significant association of any members of the thus selected smaller subset of the set of haplotypes with a phenotype of interest, which can be a disease or medical disorder, such as insulin resistance or coronary artery disease.

In accordance with the invention, a method of detecting a genetic predisposition in a human subject for developing insulin resistance is provided. The method involves collecting a biological sample from the subject; genotyping the sample at nucleotide positions 7315, 8292, 8393, 8852, 9040, and 9712, with respect to the Nickerson reference sequence of the human lipoprotein lipase gene (SEQ ID NO: 25); and assessing whether a haplotype (designated herein "haplotype 4"; see, e.g., Table 1-4) is present in the sample. The haplotype comprises the following (nucleotide position:variant allele): (i) 7315:G; (ii) 8292:A; (iii) 8393:G; (iv) 8852:G; (v) 9040:G; and (vi) 9712:G. The presence of the haplotype indicates a genetic predisposition for developing insulin resistance in the Mexican-American subject, as demonstrated hereinbelow.

Similarly, in accordance with an inventive method of detecting a lower than normal risk in a human subject for developing insulin resistance, the presence in the genotyped sample, instead, of a haplotype comprising (nucleotide position:variant allele): (i) 7315:G; (ii) 8292:A; (iii) 8393:T; (iv) 8852:T; (v) 9040:C; and (vi) 9712:G (designated herein "haplotype 1"; see, e.g., Table 1-4), indicates a lower than normal risk for developing insulin resistance in the subject, as demonstrated hereinbelow.

Alternatively, in accordance with the invention, a method of detecting a lower than normal risk in a human subject for developing coronary artery disease is provided. The method involves collecting a biological sample from the subject; genotyping the sample at nucleotide positions 7315, 8292, 8393, 8852, 9040, and 9712, with respect to the Nickerson reference sequence of the human lipoprotein lipase gene; and assessing whether the sample is homozygous for a haplotype comprising (nucleotide position:variant allele): (i) 7315:G; (ii) 8292:A; (iii) 8393:T; (iv) 8852:T; (v) 9040:C; and (vi) 9712:G (designated herein "haplotype 1"; see, e.g., Table 1-4). Homozygosity for haplotype 1 indicates a lower than normal risk for developing coronary artery disease in the subject.

If a greater than normal, or lower than normal, risk of developing insulin resistance or coronary artery disease is detected, in accordance with the invention, then suitable treatment or prophylactic modalities can be chosen, as appropriate for the individual with the benefit of this additional clinical information.

Another embodiment of the present invention relates to analyzing genetic predispositions of human subjects for various conditions including insulin sensitivity, insulin resistance, protection from coronary artery diseases, decreased Apo A-1, decreased Apo A-II, reduced graft progression after coronary surgery, reduced graft occlusion after coronary surgery, decreased diastolic blood pressure, decreased fasting insulin, decreased lipoprotein lipase activity, smaller increment in triglycerides to statin, decreased high density lipoprotein cholesterol, increased fasting insulin, increased triglycerides, increased Apo B, insulin resistance, increased body mass index, increased systolic and diastolic blood pressure, increased Apo A-I, increased Apo A-II, increased high density lipoprotein cholesterol, increased lipoprotein lipase activity, increased graft progression and occlusion after coronary surgery, increased fasting insulin and glucose, and increased visceral fat. Method of and kits for detection these predispositions are provided for human subjects. Although the data for the present invention was collected primarily from persons of Hispanic background the methods described herein for determining genetic predisposition to certain conditions is applicable to persons of all ethnic backgrounds. Methods of the present invention comprise collecting a biological sample from the subject, analyzing the genotype of the subject at selected alleles in order to determine if the subject has a given haplotype, and then correlating the haplotype with the genetic predispositions listed above. A confirmatory study of various haplotypes for any ethnic group or combination of groups can be performed using the experimental methods described in detail herein. Kits for analyzing the genetic predispositions include probes and primers directed to the selected alleles, and may include instructions, tubes, and other items for carrying out the inventive methods.

The meanings of abbreviations found herein are the following: LPL, lipoprotein lipase; CAD, coronary artery disease; MACAD, Mexican-American Coronary Artery Disease project; SNP, single nucleotide polymorphism; GINF, glucose infusion rate; $S_f$, insulin sensitivity.

DETAILED DESCRIPTION OF THE PREFERRED EMBODIMENTS

Figure 1:
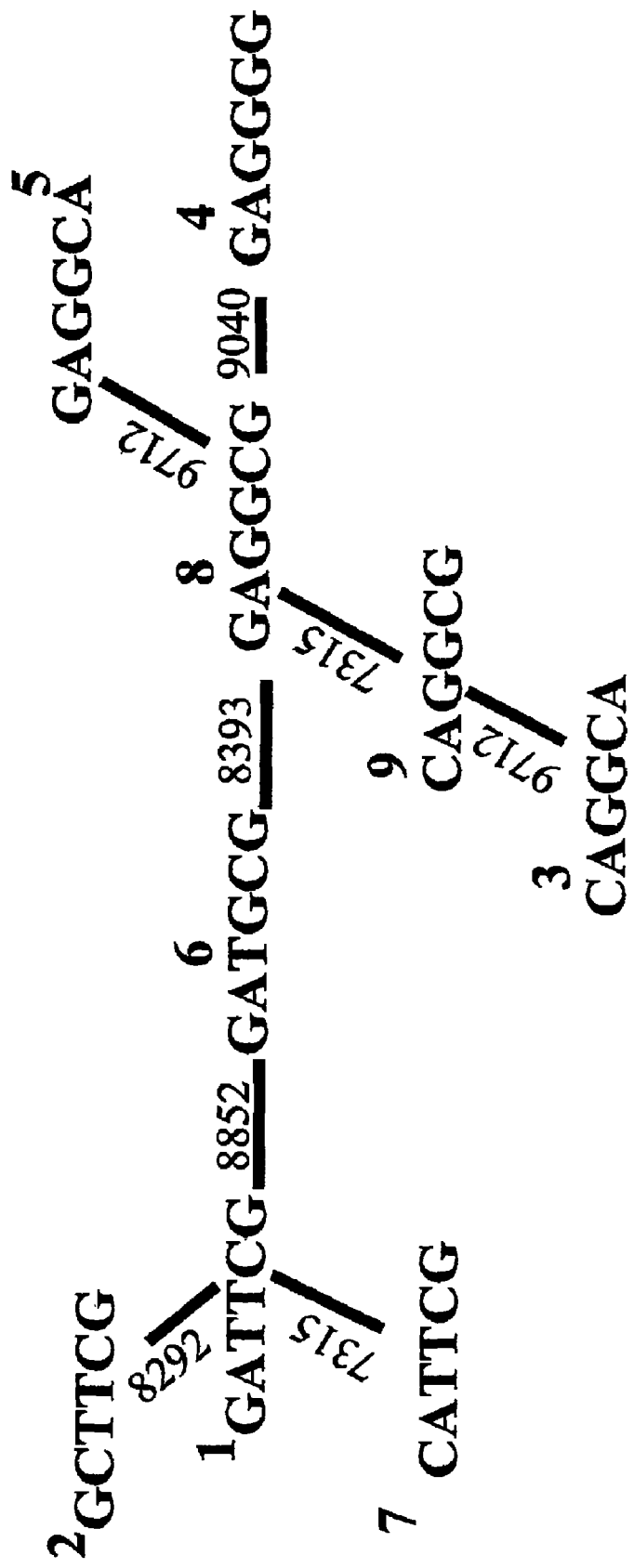
FIG. 1 illustrates the cladistic structure of the LPL 3'-end haplotypes. The lines connecting the haplotypes indicate a single nucleotide difference between the connected haplotypes, with the corresponding variant number above the line. The haplotypes are numbered in order of decreasing frequency. Haplotypes 1, 2, 6, and 7 contain HindIII allele 1; haplotypes 3, 4, 5, 8, and 9 contain HindIII allele 2.

The present invention is directed to a method for determining haplotypes within a genomic reference sequence of interest, which haplotypes are useful for large-scale genetic analysis and genetic screening tests for a human subpopulation. The genomic reference sequence of interest can be any coding or non-coding sequence of interest, for example, the human lipoprotein lipase (LPL) gene.

The LPL gene is located on the short arm of human chromosome 8, at 8p22. (R. S. Sparkes et al., Human genes involved lipolysis of plasma lipoproteins: Mapping of loci for lipoprotein lipase to 8p22 and hepatic lipase to 15q21, Genomics 1:138-44 [1987]). The gene is near microsatellite marker D8S1715 and flanked by micro satellites D8S261 and D8S280. Closer flanking sequences of human LPL are defined by GenBank accession numbers M94221 and M94222 (S. Wood et al., Support for founder effect for two lipoprotein lipase [LPL] gene mutations in French Canadians by analysis of GT microsatellites flanking the LPL gene, unpublished [1992]). The gene spans about 30 kb and contains 10 exons encoding a 475 amino acid protein including a 27 amino acid secretory signal peptide. (S. Deeb and R. Peng, *Structure of the human lipoprotein lipase gene*, Biochemistry 28(10):4131-35 [1989]; T. G. Kirchgessner et al., *Organization of the human lipoprotein lipase gene and evolution of the lipase gene family*, Proc. Natl. Acad. Sci. USA 86:9647-51 [1989]).

The 3' end of the human lipoprotein lipase gene, for purposes of the present invention, includes nucleotide positions 4801 through 9734 of the Nickerson reference sequence extending from intron 6 into intron 9. (GenBank accession No. AF050163). (D. A. Nickerson et al., *DNA sequence diversity in a 9.7-kb region of the human lipoprotein lipase gene*, Nat. Genet. 19:233-40 [1998]).

The human subpopulation can be any subpopulation of interest based on ethnicity, gender, age, or other identifiable feature distinguishing the subpopulation from the general population.

In accordance with one method "a first number of subjects" in the human subpopulation is a finite number of subjects with a minimum of 10 or more, and preferably with a minimum number of about 20 to about 40 subjects. The first number can be any number of subjects in the subpopulation up to the total number of individuals in the subpopulation, minus one. The "second number of subjects" can be any number of subjects in the subpopulation up to the total number of individuals in the subpopulation. The minimum of the second number of subjects in the human subpopulation is an appropriate number known to the skilled artisan, depending on several factors, including the frequency of particular haplotypes in the subpopulation, the frequency of particular phenotypes of interest in the subpopulation, the strength of association between a haplotype and the phenotype of interest, the desired level of statistical significance, and other like factors.

Gabriel et al. showed that the human genome is organized in haplotype blocks (most of which are longer than 10 kilobases), with three to five commonly occurring (>5%) haplotypes per block. Only six to eight variants were sufficient to define the most common haplotypes in each block. Genotyping six to eight variants thus allows determination of the most frequently occurring haplotypes in a population for association analysis. The availability of family data assists this approach by facilitating unambiguous determination of haplotypes in a more efficient and less expensive manner, based on genotyping at single variants. Variants of interest can also be selected from available databases, particularly but not exclusively, with respect to a group of non-related individuals.

A benefit of a haplotype-based analysis is that it captures all of the variation across a region, which should improve the ability to detect an association.

The "genome" of an individual member of a species comprises that individual's complete set of genes. Particular locations within the genome of a species are referred to as "loci" or "sites". "Alleles" are varying forms of the genomic DNA located at a given site. In the case of a site where there are two distinct alleles in a species, referred to as "A" and "B", each individual member of the species can have one of four possible combinations: AA; AB; BA; and BB. The first allele of each pair is inherited from one parent, and the second, on a matching chromosome, is inherited from the other parent.

The "genotype" of an individual at a specific site, or in a combination or group of associated polymorphic sites (i.e., haplotype), in the individual's genome refers to the specific combination of alleles that the individual has inherited.

The "phenotype" of an individual refers to one or more of these observable physical characteristics. An individual's phenotype is driven in large part by constituent proteins in the individual's proteome, the collection of all proteins produced by the cells comprising the individual and coded for in the individual's genome, but genetic regulatory elements can also produce a phenotype.

For the purpose of the present invention, a "genetic marker" is a single nucleotide polymorphism (SNP). "Variant", "marker", and "polymorphism" are used interchangeably herein.

For purposes of the present invention, detecting, evaluating, or assessing the presence or absence of a genetic marker (i.e., an allele) or heterozygosity or homozygosity of the subject with respect to the marker, is detected in a biological sample collected from the individual that contains the individual's genomic DNA (such as, but not limited to, a blood, saliva, or tissue biopsy sample, which biological sample can be freshly collected or suitably stored to preserve the DNA) by employing suitable biochemical genotyping analytical assay means. Analytical hybridization or polynucleotide sequencing means are typically employed, optionally after amplification of DNA in the biological sample, for example, by using PCR-based amplification means. High throughput analyses can optionally be achieved by multiplexing techniques known in the art. The genotyping analytical assay means can optionally be performed with commonly available robotic apparati and/or very dense array detection apparati. Probes, primers, and protocols useful in genotyping of a biological sample with respect to markers and haplotypes of the LPL gene are described, for example, in Table 1 and the Examples herein, and others are known to the skilled artisan (see, e.g., U.S. Pat. No. 6,297,014).

The present invention relates to a method of detecting a genetic predisposition in a human subject for developing insulin resistance. That a genetic "predisposition" is detected means that the subject, who does not currently exhibit insulin resistance, has a greater than normal risk of developing insulin resistance in the future, compared with that subject's ethnic subpopulation as a whole.

Similarly, with respect to the inventive methods of detecting a lower than normal risk in a human subject for developing insulin resistance or coronary artery disease, respectively, "lower than normal" is in comparison with the subpopulation as a whole.

As used herein, a "Mexican-American" is an individual with at least 3 of 4 grandparents native to Mexico. A Mexican-American subpopulation is a human subpopulation (i.e., an ethnic subpopulation of the general human population) consisting of such individuals.

The invention will now be described in greater detail by reference to the following non-limiting examples.

EXAMPLES

Example 1

Lipoprotein Lipase Gene Haplotypes in Mexican-Americans: Structure and Association with Coronary Artery Disease Briefly, six polymorphisms sufficient to distinguish the most common haplotypes in the 3' end of LPL were identified by genotyping ten polymorphisms in a small pilot population. These were used to haplotype LPL in large family samples of Mexican-Americans and non-Hispanic Caucasians. A case-control association study was performed comparing Mexican-Americans with and without coronary artery disease. The two ethnic groups exhibited significant genetic differences.

Among Mexican-Americans, homozygosity for LPL haplotype 1 was protective against coronary artery disease (OR=0.50, 95% CI 0.27-0.91). This study outlines the haplotype structure of the LPL gene, illustrates the utility of haplotype-based analysis in association studies, and demonstrates the importance of defining haplotype frequencies for different ethnic groups.

Materials and Methods

Subjects. The UCLA/Cedars-Sinai Mexican-American Coronary Artery Disease (MACAD) Project enrolls families ascertained through a proband with coronary artery disease, determined by evidence of myocardial infarction on electrocardiogram or hospital record, evidence of atherosclerosis on coronary angiography, or history of coronary artery bypass graft or angioplasty. DNA is obtained from all available family members, and the adult offspring of the proband and the spouses of those offspring are also asked to undergo a series of tests to characterize their metabolic and cardiovascular phenotype, including indices of insulin resistance determined by euglycemic clamp study, lipid parameters, lipase activities, and carotid intima-media thickness.

In a separate study, non-Hispanic Caucasian families were recruited for a genetic linkage study to determine the influence of specific genes on inter-individual variation in the lipoprotein response to a low-fat, high-carbohydrate diet. Siblings were placed on either a high-fat or a low-fat diet and changes in lipids and lipoproteins were monitored. We examined this population in terms of haplotype frequency for comparison to Mexican-Americans.

Genotyping.

An early stage of our haplotyping methodology consists of genotyping a number of single nucleotide polymorphisms (SNPs) spanning a region of a candidate gene in a limited number of subjects. Haplotypes are then constructed using these variants, with subsequent selection of a smaller number of variants that allow discrimination of the most common haplotypes on the majority of chromosomes observed in the population. In the second stage of the haplotyping protocol, the restricted set of SNPs identified in the first stage is genotyped in a large number of individuals using a high-throughput technology and used to determine haplotypes on a population scale.

Twenty-nine subjects from 8 randomly selected families from MACAD were genotyped at 10 single nucleotide polymorphisms (4872, 5168, 5441, 6863, 7315, 8292, 8393, 8852, 9040, 9712) originally delineated in the MDECODE (Molecular Diversity and Epidemiology of Common Disease) project, a study of Finnish, non-Hispanic Caucasian Americans, and African American subjects. The numbering of the SNPs corresponds to that reported by Nickerson, et al. and corresponds to Genbank accession number AF050163.

8393 is the HindIII variant and 9040 is the Ser447Stop variant. 4872, 5168, and 5441 are in intron 6; 6863 and 7315 are in intron 7; 8292 and 8852 are in intron 8; 9712 is in intron 9; these markers were selected because they spanned a region of the LPL gene downstream of a recombination hotspot and had a minor allele frequency of 15% or greater in MDECODE. 12 PCR amplification followed by restriction digest with HindIII was used to genotype the polymorphism at 8393. A single nucleotide primer extension method was used to genotype the remaining nine SNPs (4872, 5168, 5441, 6863, 7315, 8292, 8852, 9040, 9712). Analysis of these initial data showed that a restricted set of six SNPs encompassed all the major 3' end haplotypes.

Large-scale genotyping of these six SNPs in 514 subjects from 85 MACAD families and 629 subjects from 157 non-Hispanic Caucasian families was performed using the 5'-exonuclease (TaqMan™ MGB) assay. PCR primer and oligonucleotide probe sequences are listed in Table 1-1 below.

TABLE 1-1

Primers and probe sequences used in 5'-exonuclease assay.

| Variant | PCR primers | Taqman MGB probes |
|---|---|---|
| 7315 | Forward<br>5'-TCAAGTCATTAAAATCAATCTAGCCTTT-3'//<br>SEQ ID NO: 1;<br>Reverse<br>5'-TTCTCTTTAGATTTTATATTCCATTTTTTACTATG-3'//<br>SEQ ID NO: 2 | 5'-CCTGGGTTTCCTAcAAT-3'//<br>SEQ ID NO: 13;<br>5'-CCTGGGTTTCCTAgAAT-3'//<br>SEQ ID NO: 14 |
| 8292 | Forward<br>5'-CCTGGATAATCAAAGATTCAAACCA-3'//<br>SEQ ID NO: 3;<br>Reverse<br>5'-GGAGACAGGTTGAGATTATCTTGGA-3'//<br>SEQ ID NO: 4 | 5'-CTCACCCTTCTtGAAGA-3'//<br>SEQ ID NO: 15;<br>5'-TCACCCTTCTgGAAGA-3'//<br>SEQ ID NO: 16 |
| 8393 | Forward<br>5'-CATAAAATGAATTACACAGAGATCGCTAT-3'//<br>SEQ ID NO: 5;<br>Reverse<br>5'-TCAATCCTAACTTAGAGTTTTTTTAAATTAACA-3'//<br>SEQ ID NO: 6 | 5'-CACATTTAGTATAAAaGC-3'//<br>SEQ ID NO: 17;<br>5'-CACATTTAGTATAAAcGC-3'//<br>SEQ ID NO: 18 |
| 8852 | Forward<br>5'-GTGGCCTGAGTGTGACAGTTAATT-3'//<br>SEQ ID NO: 7;<br>Reverse<br>5'-ATCAAAAGCACTGTTCACAAAGGTA-3'//<br>SEQ ID NO: 8 | 5'-AGCATGATCATGTAtTAT-3'//<br>SEQ ID NO: 19;<br>5'-CAGCATGATCATGTAgTAT-3'//<br>SEQ ID NO: 20 |

TABLE 1-1-continued

Primers and probe sequences used in 5'-exonuclease assay.

| Variant | PCR primers | Taqman MGB probes |
|---|---|---|
| 9040 | Forward<br>5'-TTGTGAAATGCCATGACAAGTCT-3'//<br>SEQ ID NO: 9;<br>Reverse<br>5'-CCAGTCAGCTTTAGCCCAGAA-3'//<br>SEQ ID NO: 10 | 5'-CCAGCCTgACTTC-3'//<br>SEQ ID NO: 21;<br>5'-ACCAGCCTcACTTC-3'//<br>SEQ ID NO: 22 |
| 9712 | Forward<br>5'-TCCATGTGGCAGCTGTTAGC-3'//<br>SEQ ID NO: 11;<br>Reverse<br>5'-GAGTAGTGAAGGTCACATGCTTAGTGT-3'//<br>SEQ ID NO: 12 | 5'-CCAGAGCgTCAGTAC-3'//<br>SEQ ID NO: 23;<br>5'-CCAGAGCaTCAGTAC-3'//<br>SEQ ID NO: 24 |

In this assay, allele-specific oligonucleotide probes are labeled with different fluorophores (FAM or VIC) at their 5'-ends and with a quencher molecule at the 3'-end. The quencher interacts with the fluorophores by fluorescence resonance energy transfer, quenching their fluorescence. These probes are included in the PCR reaction mixture amplifying a 100-150 base pair segment with the polymorphism at the center. During annealing, the probes hybridize to the PCR products, and during extension, the 5'-3' exonuclease activity of the DNA polymerase degrades perfectly matched annealed probes, separating the fluorophore from the quencher. Imperfectly matched probes are displaced into solution without degradation. Comparison of relative fluorescence from each fluorophore allows determination of genotype.

Data Analysis. Based on pedigree structures and genotype data of all individuals in each pedigree, haplotypes were reconstructed as the most likely set (determined by the maximum likelihood method) of fully-determined parental haplotypes of the marker loci for each individual in the pedigree, using the simulated annealing algorithm implemented in the program Simwalk2. All comparisons between groups of subjects comprised comparisons of unrelated founders, and only founder chromosome data are presented in the tables. Founder haplotypes, i.e. those haplotypes from parents and individuals marrying into the family, were used to calculate haplotype frequencies in 482 chromosomes from 241 Mexican-American founders and in 582 chromosomes from 291 non-Hispanic Caucasian founders.

Six Mexican-American and 21 non-Hispanic Caucasian founders were excluded from analysis because their haplotypes could not be unambiguously determined. The $X^2$ test was used to compare allele and haplotype frequencies between the Mexican-Americans without coronary artery disease and the non-Hispanic Caucasians.

A case-control association study of coronary artery disease was performed by comparing haplotype frequencies between Mexican-American founders with and those without coronary artery disease. The cases were 77 probands (154 chromosomes) with coronary artery disease; the controls (164 individuals, 328 chromosomes) were their spouses plus the spouses marrying into the offspring generation. Because the cases and controls were genetically unrelated, their allele and haplotype frequencies and gender distribution were compared using the $X^2$ test. Student's T test was used to compare the mean age of the cases versus the controls. Odds ratios for coronary artery disease by haplogenotype were calculated, using logistic regression analysis to adjust for any confounding effects of age or sex in the case-control comparison. Analyses were performed using SAS System software.

Results

In a pilot study, the haplotypes of 28 unique chromosomes were derived using Mexican-American family data and are shown in Table 1-2 (below) in order of frequency. These results were used to select the markers genotyped in the large population samples. As seen in Table 1-2, markers 7315, 8292, 8393, 8852, and 9040 are sufficient to distinguish the haplotypes from each other. In addition to these five SNPs, 9712 was also chosen because it is predicted to distinguish two major ancient clades according to the haplotype tree constructed by Templeton, et al. in the Molecular Diversity and Epidemiology of Common Disease (MDECODE) project. The results reported herein are consistent with their study of the haplotype structure of 9.7 kb of the LPL gene that described four ancient cladistic groups. Markers 7315, 8393, and 9712 are useful to distinguish all four of the ancient 3' LPL clades.

TABLE 1-2

Pilot study LPL haplotypes.

| Haplotype | 4872 | 5168 | 5441 | 6863 | 7315 | 8292 | 8393H | 8852 | 9040 | 9712 | Count | Frequency |
|---|---|---|---|---|---|---|---|---|---|---|---|---|
| 1 | A | T | T | C | G | A | T | T | C | G | 13 | 46.4% |
| 2 | G | C | T | C | G | A | G | G | G | G | 4 | 14.3% |
| 3 | A | T | T | C | G | A | G | G | C | A | 3 | 10.7% |
| 4 | A | T | T | C | G | C | T | T | C | G | 3 | 10.7% |
| 5 | G | C | T | T | C | A | G | G | C | A | 3 | 10.7% |
| 6 | G | T | T | C | C | A | T | T | C | G | 1 | 3.6% |
| 7 | A | T | T | C | G | A | T | G | C | G | 1 | 3.6% |

In the second stage, the six selected markers were then genotyped in 514 Mexican-American subjects from 85 families and 629 subjects from 157 non-Hispanic Caucasian families. The allele frequencies are shown in Table 1-3 (below). The markers from Mexican-Americans without coronary artery disease are presented in Table 3 in order to eliminate any disease-based ascertainment bias in delineating the ethnic comparison.

TABLE 1-3

LPL SNP allele frequencies in Mexican-Americans and non-Hispanic Caucasians.

| Position | Variant | Mexican-American without CAD (328 chromosomes) | Non-Hispanic Caucasion (582 chromosomes) | P value |
|---|---|---|---|---|
| 7315 | G → C | 0.89 | 0.85 | 0.08 |
| 8292 | A → C | 0.85 | 0.79 | 0.03 |
| 8393 | T → G | 0.80 | 0.71 | 0.003 |
| 8852 | T → G | 0.78 | 0.70 | 0.01 |

TABLE 1-3-continued

LPL SNP allele frequencies in Mexican-Americans and non-Hispanic Caucasians.

| Position | Variant | Mexican-American without CAD (328 chromosomes) | Non-Hispanic Caucasion (582 chromosomes) | P value |
|---|---|---|---|---|
| 9040 | C → G | 0.93 | 0.90 | 0.10 |
| 9712 | G → A | 0.88 | 0.81 | 0.02 |

Of note, while 9040 (Ser447Stop) was extremely rare in the previous MDECODE study subjects (not detected in African Americans or Finns and found with a frequency of 4% in U.S. non-Hispanic Caucasians), in this study it was found with a frequency of 7% in Mexican Americans and 9% in our non-Hispanic Caucasians. Comparing Mexican-Americans to non-Hispanic Caucasians, the allele frequencies were significantly different for four out of the six variants (Table 1-3).

The founder haplotype frequencies from the Mexican-Americans without coronary artery disease (as determined by EKG or by hospital records of, e.g., angioplasty, coronary artery bypass graft surgery, or angiography) were compared with those of the non-Hispanic Caucasians. The six most common haplotypes, comprising over 99% of the observed haplotypes for each group, are presented in Table 1-4 (below).

Both groups shared haplotype I as the most common haplotype. There were several differences between the two groups in regards to the other haplotypes. Haplotypes 2, 3, 4, and 5 were more common in the non-Hispanic Caucasian population; haplotypes I and 6 were more common in the Mexican-Americans. These differences reached statistical significance for the three most frequent haplotypes.

In the case-control study, Mexican-American probands with coronary artery disease were compared with their spouses and the spouses of their offspring, none of whom had coronary artery disease. Thus, these case and control individuals were all genetically unrelated. The mean age of the cases was 62.2 years; that of the controls was 42.6 years (P<0.0001). This age difference was expected, given that the control group was comprised of individuals from both the parental and offspring generations. The sex distribution was similar between the groups, with males comprising 44% of the cases and 38% of the controls ($X^2=0.9$, P=0.35).

TABLE 1-4

LPL haplotype frequencies in Mexican-Americans compared to non-Hispanic 20 Caucasians.

| Haplotype | 7315 | 8292 | 8393 | 8852 | 9040 | 9712 | Mexican | Freq | Caucasian | Freq | P value |
|---|---|---|---|---|---|---|---|---|---|---|---|
| 1. | G | A | T | T | C | G | 206 | 62.8% | 284 | 48.8% | <0.0001 |
| 2. | G | C | T | T | C | G | 50 | 15.2% | 123 | 21.1% | 0.03 |
| 3. | C | A | G | G | C | A | 33 | 10.1% | 85 | 14.6% | 0.05 |
| 4. | G | A | G | G | G | G | 22 | 6.7% | 58 | 10.0% | 0.10 |
| 5. | G | A | G | G | C | A | 8 | 2.4% | 24 | 4.1% | 0.19 |
| 6. | G | A | T | G | C | G | 6 | 1.8% | 5 | 0.9% | 0.20 |
| | | | | | | | 325 | 99.1% | 579 | 99.5% | |

The genotype frequencies for all six markers were in Hardy-Weinberg equilibrium for both the cases and the controls. Allele frequencies of the six SNPs did not differ significantly among the Mexican-Americans according to coronary artery disease status (Table 1-5). A comparison of genotype frequencies showed no differences between cases and controls, except for a modestly significant difference for the 8393 (HindIII) variant (P=0.05). However, comparison of the common haplotype frequencies between the Mexican-Americans with and without coronary artery disease revealed a significant decrease in the frequency of the most common haplotype in those with disease (Table 1-6 below). This implies an increase in frequency of less common haplotypes among cases, the detection of which was hindered by the available sample size. Haplotype 1 was associated with a significantly decreased risk of coronary artery disease (P=0.03). Of the less common haplotypes, haplotype 4 was most prominently associated with the greatest risk of coronary artery disease (P=0.10), though this result did not attain statistical significance with the given sample size. A comparison of subjects homozygous for haplotype 1 with subjects with all other genotypes is presented in Table 1-7 (below). Homozygosity for haplotype 1 was associated with protection against coronary artery disease with an odds ratio of 0.50 (95% CI 0.27-0.91). Use of the logistic regression model to adjust for age and sex, separately and in combination (Table 1-6), did not alter the significance of this association (odds ratio estimates from 0.39 to 0.51). None of the haplotypes other than haplotype 1 showed a statistically significant association with coronary artery disease (data not shown).

TABLE 1-5

LPL SNP allele and genotype frequencies in
Mexican-Americans with and without CAD.

| SNP | | Frequency of major allele | P value[a] | Major allele[b] homozygote | Heterozygote | Minor allele[b] homozygote | P value[c] |
|---|---|---|---|---|---|---|---|
| 7315 | Cases | 0.89 | 0.46 | 57 | 20 | 0 | 0.31 |
| | Controls | 0.87 | | 131 | 31 | 2 | |
| 8292 | Cases | 0.85 | 0.41 | 52 | 22 | 3 | 0.48 |
| | Controls | 0.82 | | 118 | 42 | 4 | |
| 8393 | Cases | 0.80 | 0.06 | 39 | 33 | 5 | 0.05 |
| | Controls | 0.72 | | 105 | 52 | 7 | |
| 8852 | Cases | 0.78 | 0.08 | 38 | 33 | 6 | 0.09 |
| | Controls | 0.71 | | 100 | 56 | 8 | |
| 9040 | Cases | 0.93 | 0.10 | 61 | 15 | 1 | 0.14 |
| | Controls | 0.89 | | 142 | 22 | 0 | |
| 9712 | Cases | 0.88 | 0.27 | 54 | 21 | 2 | 0.37 |
| | Controls | 0.84 | | 124 | 39 | 1 | |

[a]For the comparison of allele frequency between cases and controls: $\chi^2$ (1 d.f.)
[b]Major and minor alleles are listed in Table 4.
[c]Major allele homozygotes versus heterozygotes plus minor allele homozygotes, comparing cases and controls: $\chi^2$ (1 d.f.)

TABLE 1-6

LPL haplotype frequencies in Mexican-Americans with and without coronary artery disease.

| Haplotype | 7315 | 8292 | 8393 | 8852 | 9040 | 9712 | CAD | Freq | No CAD | Freq | P value |
|---|---|---|---|---|---|---|---|---|---|---|---|
| 1. | G | A | T | T | C | G | 81 | 52.6% | 206 | 62.8% | 0.03 |
| 2. | G | C | T | T | C | G | 28 | 18.2% | 50 | 15.2% | 0.42 |
| 3. | C | A | G | G | C | A | 20 | 13.0% | 33 | 10.1% | 0.34 |
| 4. | G | A | G | G | G | G | 17 | 11.0% | 22 | 6.7% | 0.10 |
| 5. | G | A | G | G | C | A | 5 | 3.3% | 8 | 2.4% | 0.61 |
| 6. | G | A | T | G | C | G | 2 | 1.3% | 6 | 1.8% | 0.67 |
| | | | | | | | 153 | 99.4% | 325 | 99.1% | |

TABLE 1-7

Logistic regression analysis comparing haplotype
1 homozygotes with all other haplogenotypes.

| Adjustment | Odds Ratio | 95% CI | P value |
|---|---|---|---|
| None | 0.50 | 0.27-0.91 | 0.02 |
| Sex | 0.51 | 0.28-0.93 | 0.03 |
| Age | 0.41 | 0.18-0.93 | 0.03 |
| Sex and Age | 0.39 | 0.17-0.89 | 0.03 |

In comparing two different ethnic groups, we found several differences in the allele and haplotype frequencies observed in the 3' LPL markers. Such differences may affect results of association studies conducted in different populations. In particular, different alleles of HindIII occurred at different frequencies, which may account for disparate results of association studies conducted in different populations. For example, a study of postmenopausal Caucasian women found no association of the HindIII variant with glucose or insulin levels, while a study in Chinese men with coronary heart disease found an association of HindIII with steady state plasma glucose levels, a marker of insulin resistance.

The haplotypes described here can be very useful in future studies exploring the association of the LPL gene with components of the cardiovascular dysmetabolic syndrome. This is illustrated here, in that haplotype frequencies were different according to coronary artery disease status. Only one out of six single polymorphic sites was associated with coronary artery disease. This demonstrates that the common approach of examining one or two polymorphisms per candidate gene may fail to detect phenotypic associations. Compared to single-variant analysis, haplotype-based analysis reduces the potential for false negatives in association studies. The benefit of a haplotype-based analysis is that it captures all of the variation across a region, which should, as it did in our study, improve the ability to detect an association. This study thus demonstrates the improved power of haplotyping in elucidating disease gene associations and the importance of ethnic specific haplotype data.

Example 2

Haplotype Analysis of the Association of the Lipoprotein Lipase Gene with Insulin Sensitivity Lipoprotein lipase (LPL) is a candidate gene implicated in features of the cardiovascular dysmetabolic syndrome, atherosclerosis and components of the insulin resistance syndrome, i.e., hypertension, lipid levels, and fasting insulin.

The aim of this study was to evaluate the relationship between the LPL gene and direct measurement of insulin sensitivity in Mexican American families ascertained through patients with CAD, a population and disorder with a high frequency of insulin resistance. Insulin sensitivity was evaluated by assessment of the glucose infusion rate (GINF) during a euglycemic hyperinsulinemic clamp study, which is widely regarded as the most direct physiologic measurement of insulin sensitivity.

Mexican-American nuclear families were ascertained via a parent with documented CAD in the Los Angeles area. A total of 91 adult offspring underwent euglycemic clamp to determine peripheral glucose disposal. Insulin sensitivity ($S_I$) was calculated from the glucose infusion rate (GINF) and increment in plasma insulin over basal for each offspring. Both parents and offspring were genotyped for eight polymorphic markers spanning a distance of 6.9 cM at or near the LPL gene on chromosome 8 (D8S261, LPL3, HindIII, PvuII, LPL5, D8S258, D8S282, D8S136).

Linkage analysis was conducted using linear regression method as implemented in the SIBPAL program of the SAGE package. Association between HindIII polymorphic markers and $S_I$ was evaluated by comparing the maximum likelihood of the two models incorporating familial correlation (with or without the marker) as implemented in the ASSOC program.

Results: Multiple markers at or near the LPL gene showed significant evidence of linkage (0.003p0.05) to $S_I$. Furthermore, a significant association between allele 2 of HindIII polymorphism within the LPL gene itself and insulin sensitivity ($S_I$) was also observed (p=0.008).

This shows a linkage of markers near and within LPL to insulin resistance in a family study of Mexican-Americans ascertained by probands with coronary artery disease, and also shows association of the HindIII polymorphism with a direct measurement of insulin sensitivity ($S_I$, calculated from euglycemic clamp study). HindIII allele 2 is associated with decreased $S_I$. Thus, in Mexican American families ascertained through CAD probands, we have for the first time shown that the LPL gene is both linked and associated with a direct measure of insulin resistance. This observation provides the most direct evidence as to the importance of the LPL gene in the insulin resistance syndrome and provides a pathophysiologic mechanism for its relation to the development of CAD.

In a further study described hereinbelow our goal was to identify specific haplotypes (groups of alleles on the same chromosome) associated with insulin sensitivity in an expanded family sample undergoing glucose clamps.

Example 3

Evidence of Linkage and Between LPL and Insulin Association Sensitivity/Resistance in Mexican-American Hypertension Families We have shown hereinabove that blood pressure (BP) and insulin sensitivity/resistance (IR) cosegregate in Mexican-American families and that there most likely are gene(s) contributing to both BP and IR. Previous studies have shown evidence of linkage and/or association of the HindIII polymorphism in the LPL gene with IR, as well as IR-associated hypertension, dyslipidemia, and atherosclerosis. However, in most cases insulin sensitivity was assessed by indirect methods. To further examine the role of the LPL gene in IR, we genotyped six (7315, 8292, 8393, 8852, 9040, 9712) LPL 3' end single nucleotide polymorphisms (SNPs) in 390 members of 77 Hispanic families ascertained via hypertensive probands. Insulin sensitivity/resistance was directly assessed via hyperinsulinemic euglycemic glucose clamps. Multipoint linkage analyses were performed using SIBPAL2. Association between the six SNPs, LPL haplotypes and IR-related traits were evaluated using the QTDT program.

Materials and Methods.

Subjects. The UCLA/Cedars-Sinai Mexican-American Coronary Artery Disease (MACAD) Project enrolls families ascertained through a proband with coronary artery disease, determined by evidence of myocardial infarction on electrocardiogram or hospital record, evidence of atherosclerosis on coronary angiography, or history of coronary artery bypass graft or angioplasty. DNA was obtained from all available family members, and the adult offspring (age 18 or older) of the proband and the spouses of those offspring were also asked to undergo a series of tests to characterize their metabolic and cardiovascular phenotype.

Genotyping. In a study described hereinabove, we determined a set of six SNPs that are sufficient to identify the most common haplotypes occurring in the 3' end of the LPL gene. These are 7315, 8292, 8393, 8852, 9040, and 9712. The numbering of the SNPs corresponds to Genbank accession number AF050163, which describes a 9.7 kb segment of the LPL gene originally sequenced in the Molecular Diversity and Epidemiology of Common Disease (MDECODE) project, a study of Finns, non-Hispanic Caucasian Americans, and African-American subjects. 8393 is the HindIII variant located in intron 8 and 9040 is the Ser447Stop variant located in exon 9. 7315 is in intron 7; 8292 and 8852 are in intron 8; 9712 is in intron 9.

Large-scale genotyping of the six SNPs in MACAD families was performed using the 5'-exonuclease (TaqMan™ MGB) assay. PCR primer and oligonucleotide probe sequences are listed in Table 3-1 (Goodarzi et al.). In this assay, allele-specific oligonucleotide probes were labeled with different fluorophores (FAM or VIC) at their 5'-ends and with a quencher molecule at the 3'-end. The quencher interacts with the fluorophores by fluorescence resonance energy transfer, quenching their fluorescence.

These probes are included in the PCR reaction mixture amplifying a 100-150 base pair segment with the polymorphism at the center. During annealing, the probes hybridize to the PCR products, and during extension, the 5'-3' exonuclease activity of the DNA polymerase degrades perfectly matched annealed probes, separating the fluorophore from the quencher. Imperfectly matched probes are displaced into solution without degradation.

Comparison of relative fluorescence from each fluorophore allows determination of genotype.

LPL markers were genotyped in 514 individuals from 85 MACAD families. Of these, 29 individual genotypes were discarded because their genotypes were incompatible with their family pedigree, as detected by the program Pedcheck. This left 485 individuals genotyped at LPL. The genotype frequencies for all six markers were in Hardy-Weinberg equilibrium.

Phenotyping. The adult offspring of the proband and the spouses of the offspring underwent a three-day phenotyping protocol, which includes indices of insulin resistance determined by euglycemic clamp study, lipid parameters, and carotid intima-media thickness. Of the 485 subjects genotyped at LPL, 125 were from the parental generation that does not undergo phenotyping, and 69 from the offspring generation were not clamped. Thus, 291 subjects from 74 families were both clamped and genotyped for the LPL markers.

Several indices of insulin sensitivity are obtained in the MACAD study. Fasting insulin and glucose, themselves simple surrogate measures of insulin sensitivity, allow calculation of the homeostasis model assessment index. Using glucose in mmol/L and insulin in µIU/mL, the HOMA index is (glucose×insulin)/22.5. An ideal, normal-weight person aged <35 years has a HOMA of 1.

During the hyperinsulinemic euglycemic clamp, human insulin (Novolin, Clayton, N.C.; 60 mU/m$^2$/min) was infused for 120 minutes at a constant rate to achieve a plasma insulin concentration of 100 µIU/mL or greater. Blood was sampled every 5 minutes, and the rate of 20% dextrose co-infused was adjusted to maintain plasma glucose concentrations at 95 to 100 mg/dL. The glucose infusion rate (GINF, given in mg/min) over the last 30 minutes of steady-state insulin and glucose concentrations reflects glucose uptake by all tissues of the body (primarily insulin-mediated glucose uptake in muscle) and is therefore a direct physiologic measurement of tissue insulin sensitivity. GINF is also often reported divided by body weight, resulting in a trait termed the M value (mg/kg/min).

Data Analysis. Based on the pedigree structures and genotype data of all individuals in each pedigree, haplotypes were reconstructed as the most likely set (determined by the maximum likelihood method) of fully-determined parental haplotypes of the marker loci for each individual in the pedigree, using the simulated annealing algorithm implemented in the program Simwalk2. Using this method we were able to assign haplotypes to 475 of the 485 genotyped subjects, including 285 of the 291 genotyped and clamped subjects. Founder haplotypes, i.e. those haplotypes from parents and individuals marrying into the families, were used to calculate haplotype frequencies in 482 chromosomes from 241 Mexican-American founders (125 parents, 116 spouses of offspring). The frequencies of the most common haplotypes among 328 chromosomes of the 164 founders (48 parents, 116 spouses) without coronary artery disease are displayed in Table 3-1 along with the major allele frequencies of the six SNPs. The markers from Mexican-Americans without coronary artery disease are presented in Table 3-1 in order to eliminate any disease-based ascertainment bias.

Log-transformed (anthropometric measurements, fasting glucose, fasting insulin) or square-root-transformed (HOMA, GINF, M) trait values were used to reduce skewness for all statistical analyses. Unpaired, two-sided T tests were used to compare trait values between men and women.

Linkage was assessed using sib pair analysis. The basic idea of this approach is that if a locus influences the quantitative trait or phenotype under study, then siblings that share more alleles at that locus will be more similar in phenotype than siblings that share fewer alleles. Conceptually, this procedure first plots the square of the difference in the quantitative trait between each sibpair versus the number of alleles shared, and then uses linear regression to estimate how much of the difference in the trait depends on the number of alleles shared. A significant linkage is shown by a negative regression coefficient. If there is no linkage, the regression coefficient is expected to be zero. We used the SIBPAL2 program in SAGE 4.2 to implement a sib pair analysis that uses the mean-corrected cross-product instead of the squared difference of the sibs trait values as the dependent variable; this revised method has more power and accommodates multiple sibs in a family.

Association was evaluated by quantitative transmission disequilibrium testing for both individual polymorphisms and haplotypes using the QTDT program. The transmission disequilibrium test was first developed for dichotomous traits in which alleles transmitted and not transmitted from the parents to affected offspring are compared to determine whether one allele is associated with the disease in question. This was later extended to quantitative traits. Abecasis developed a general approach for scoring allelic transmission that accommodates families of any size and uses all available genotypic information. Family data allows for the construction of an expected genotype for every non-founder, and orthogonal deviates from this expectation are a measure of allelic transmission. The QTDT program implements this general transmission disequilibrium testing using the orthogonal model of Abecasis. Age, gender, and body mass index were specified as covariates. Environmental variance, polygenic variance, and additive major locus were specified in the variance model. In all cases of a positive association result, the population stratification model was also executed to confirm the absence of significant population stratification.

Results

The clinical characteristics of the 291 subjects (112 men, 179 women) who had quantitative assessment of insulin resistance are shown in Table 3-2 below. This is an adult group of Mexican-Americans of mean age 35.3 years. On average, these individuals are overweight. This may account for the degree of insulin resistance observed; however, it is known that Mexican-Americans have a predisposition to visceral adiposity, hyperinsulinemia, and insulin resistance. The mean HOMA level suggests that these people are on average almost four times more insulin resistant than normal. The men had statistically significant higher weight (P<0.0001) and fasting glucose (P=0.0023) levels, while the women had significantly lower GINF (P=0.0001) but not M values.

TABLE 3-1

LPL single marker and haplotype frequencies in Mexican-Americans.

| SNPs and major allele frequencies | 7315 G→C 0.89 | 8292 A→C 0.85 | 8393 T→G 0.80 | 8852 T→G 0.78 | 9040 C→G 0.93 | 9712 G→A 0.88 | Subjects | Freq |
|---|---|---|---|---|---|---|---|---|
| Haplotype 1 | G | A | T | T | C | G | 206 | 62.8% |
| Haplotype 2 | G | C | T | T | C | G | 50 | 15.2% |
| Haplotype 3 | C | A | G | G | C | A | 33 | 10.1% |
| Haplotype 4 | G | A | G | G | G | G | 22 | 6.7% |
| Haplotype 5 | G | A | G | G | C | A | 8 | 2.4% |
| Haplotype 6 | G | A | T | G | C | G | 6 | 1.8% |

TABLE 3-2

Clinical characteristics of 291 genotyped and clamped individuals.

| | Mean | SD | Range |
|---|---|---|---|
| Age (yr) | | | |
| Men (n = 112) | 35 | 9.4 | 19-60 |
| Women (n = 179) | 35.5 | 8.2 | 18-58 |
| Weight (kg)* | | | |
| Men | 84.2 | 15.6 | 52.5-126.6 |
| Women | 72.1 | 14.0 | 38.6-128.5 |
| Body mass index (kg/m$^2$) | | | |
| Men | 28.9 | 4.8 | 17.8-45.4 |
| Women | 29.1 | 5.5 | 18.1-54.8 |

TABLE 3-2-continued

Clinical characteristics of 291 genotyped and clamped individuals.

|  | Mean | SD | Range |
|---|---|---|---|
| Fasting glucose (mg/dL)* | | | |
| Men | 96.1 | 9.8 | 74.0-118.0 |
| Women | 92.5 | 9.4 | 56.0-117.0 |
| Fasting insulin (µIU/mL) | | | |
| Men | 15.4 | 8.9 | 5.0-62.0 |
| Women | 15.5 | 7.5 | 2.0-49.0 |
| HOMA (µIU/mL × mmol/L) | | | |
| Men | 3.7 | 2.4 | 1.2-15.9 |
| Women | 3.6 | 1.9 | 0.5-14.0 |
| GINF (mg/min)* | | | |
| Men | 428.6 | 196.8 | 105.9-1031.5 |
| Women | 343.5 | 147.5 | 20.7-1010.5 |
| M (mg/kg/min) | | | |
| Men | 5.4 | 2.8 | 1.0-13.9 |
| Women | 5.0 | 2.4 | 0.2-14.9 |

*P < 0.005 comparing men versus women

Linkage results are shown in table 3-3. Of the several indices of insulin sensitivity, linkage was demonstrated only for the direct quantification represented by GINF. The M value, a clamp-derived index equal to GINF/body weight, was not significantly linked to LPL haplotypes.

TABLE 3-3

Linkage results for measurements of insulin sensitivity and LPL haplotypes

| Phenotype | P value (from SIBPAL) |
|---|---|
| Fasting glucose | 0.57 |
| Fasting insulin | 0.44 |
| HOMA | 0.34 |
| GINF | 0.034 |
| M | 0.32 |

Association was evaluated by quantitative transmission disequilibrium testing. Positive association results for particular haplotypes are shown in Table 3-4 (below). No haplotype was significantly associated with fasting glucose, fasting insulin, or HOMA, but both haplotypes 1 and 4 were significantly associated with both GINF and the M value. To characterize the nature of the associations of haplotypes 1 and 4 with insulin resistance, we determined the mean levels of insulin sensitivity in carriers of these haplotypes (Table 3-4 and FIG. 2). We observed that haplotype 1 is associated with the most favorable mean insulin sensitivity, while carriers of haplotype 4 had the lowest insulin sensitivity (i.e. the greatest insulin resistance). For fasting insulin, HOMA, GINF, and M, mean insulin sensitivity progressively worsened going from haplotype 1 homozygotes to haplotype 1 heterozygotes to individuals without haplotype 1. Conversely, haplotype 4 heterozygotes were more insulin resistant than those without haplotype 4 (no haplotype 4 homozygotes were observed among the clamped subjects). FIG. 3 further explores these associations by examining the effects of haplotypes 1 and 4 on insulin sensitivity independently. Exclusion of subjects with haplotype 4 from haplotype 1 heterozygotes and those without haplotype 1 did not affect the trend of benefit on insulin sensitivity seen with increasing numbers of haplotype 1. Similarly, excluding haplotype 1 carriers from those with and without haplotype 4 did not affect the trend of lower insulin sensitivity in the latter subjects; in fact, the subjects without haplotype 1 who were carriers of haplotype 4 had the lowest insulin sensitivity (most insulin resistance) compared to the other haplogenotype groups. Similar trends were observed with M value.

TABLE 3-4

LPL haplotype association results for indices of insulin sensitivity.

| Phenotype | Haplotype | P value for association (from QTDT) | Mean trait value for haplotype carriers |
|---|---|---|---|
| GINF | 1 | 0.031 | 383.0 mg/min |
|  | 4 | 0.007 | 344.3 mg/min |
| M | 1 | 0.031 | 5.3 mg/kg/min |
|  | 4 | 0.005 | 4.6 mg/kg/min |

It is believed that the study described hereinabove is the first that has used insulin sensitivity assessed by the euglycemic clamp as the phenotype in an association study with LPL. Two LPL haplotypes were associated with variation in GINF. These haplotypes had opposite effects on insulin sensitivity. Haplotype 1, the most common haplotype, was associated with improved insulin sensitivity. As the number of chromosomes in an individual with haplotype 1 decreased (from two, to one, to none), insulin sensitivity by GINF, as well as HOMA and fasting insulin, decreased progressively. Furthermore, haplotype 4 carriers had the lowest insulin sensitivity, i.e. they were the most insulin resistant. The direction of these associations persisted when the haplotypes were considered separately. With the available data we cannot determine whether there is an insulin-sensitizing functional variant on haplotype 1 chromosomes and/or a variant on haplotype 4-bearing chromosomes that promotes insulin resistance. However, in terms of the relation to cardiovascular risk associated with the metabolic syndrome, our previous work has shown that haplotype 1 is associated with protection against coronary artery disease and haplotype 4 may be associated with increased risk of coronary artery disease (see Example 1 hereinabove).

Example 4

Lipoprotein Lipase is a Gene for Insulin Resistance in Mexican Americans

Research Design and Methods.

The UCLA/Cedars-Sinai Mexican-American Coronary Artery Disease (MACAD) project enrolls families ascertained through a proband with CAD, determined by evidence of myocardial infarction on electrocardiogram or hospital record, evidence of atherosclerosis on coronary angiography, or history of coronary artery bypass graft or angioplasty. Two generations are enrolled in the study: 1) the proband and proband spouses (parental generation); and 2) their adult (aged ≧18 years) offspring and the spouses of those offspring (offspring generation). DNA was obtained for genotyping from members of both generations, and only members of the offspring generation were asked to undergo a series of tests to characterize their metabolic and cardiovascular phenotype.

All studies were approved by Human Subjects Protection Institutional Review Boards at UCLA and Cedars-Sinai Medical Center. All subjects gave informed consent before participation.

Genotyping. In a prior study, we determined a set of six SNPs that are sufficient to identify the most common haplotypes occurring in the 3' end of the LPL gene. These are 7315, 8292, 8393, 8852, 9040, and 9712. The numbering of the SNPs corresponds to Genbank accession no. AF050163, which describes a 9.7-kb segment of the LPL gene originally sequenced in the MDECODE (Molecular Diversity and Epidemiology of Common Disease) project, a study of Finns, non-Hispanic Caucasian Americans, and African-American subjects. SNP 8393 is the HindIII variant located in intron 8, and 9040 is the Ser447Stop variant located in exon 9. SNP 7315 is in intron 7, 8292 and 8852 are in intron 8, and 9712 is in intron 9. Large-scale genotyping of the six SNPs in MACAD families was performed using the 5'-exonuclease (TaqMan™ MGB) assay. A description of this technique and PCR primer and oligonucleotide probe sequences is given in Goodarzi et al.

LPL markers were genotyped in 514 individuals from 85 MACAD families. Of these, 29 genotyped individuals were discarded because their genotypes were incompatible with their family pedigree, as detected by the program PedCheck. This left 485 individuals from 80 families genotyped at LPL. The genotype frequencies for all six markers were in Hardy-Weinberg equilibrium. Linkage disequilibrium among the six markers (D') ranged from 0.46 to 0.87.

Phenotyping. The adult offspring of the proband and the spouses of the offspring undergo a 3-day phenotyping protocol, which includes indexes of insulin resistance determined by euglycemic clamp. Of the 485 subjects genotyped at LPL, 125 were from the parental/proband generation that was not phenotyped, and 69 (from six families) from the offspring generation were not clamped. Thus, 291 subjects from 74 families were both clamped and genotyped for the LPL markers.

Several indexes of insulin sensitivity are obtained in the MACAD study. Fasting insulin and glucose, themselves simple surrogate measures of insulin sensitivity, allow calculation of the homeostasis model assessment (HOMA) index. Using glucose in mmol/l and insulin in μIU/ml, the HOMA index is calculated as (glucose×insulin)/22.5. An ideal, normal-weight person aged less than 35 years has a HOMA of 1. During the hyperinsulinemic-euglycemic clamp, a priming dose of human insulin (Novolin; Novo Nordisk, Clayton, N.C.) was given and followed by infusion for 120 min at a constant rate (60 mU/m$^{-2}$/min$^{-1}$) to achieve a plasma insulin concentration of ≧100 μIU/ml. Blood was sampled every 5 min, and the rate of 20% dextrose coinfused was adjusted to maintain plasma glucose concentrations at 95-100 mg/dl. The GINF (given in mg/min) over the last 30 min of steady-state insulin and glucose concentrations reflects glucose uptake by all tissues of the body (primarily insulin-mediated glucose uptake in muscle) and is therefore a direct physiologic measurement of tissue insulin sensitivity. GINF is also often reported divided by body weight, resulting in a trait termed the M value (mg/kg$^{-1}$/min$^{-1}$). GINF and the M value underestimate the total glucose disposal rate during the euglycemic clamp in conditions where hepatic glucose output is not completely suppressed by the insulin infusion. In nondiabetic insulin-resistant subjects, such as those in our study, M underestimates total glucose disposal only by ≦10%.

Data analysis. Based on the pedigree structures and genotype data of all individuals in each pedigree, haplotypes were constructed as the most likely set (determined by the maximum likelihood method) of fully determined parental haplotypes of the marker loci for each individual in the pedigree, using the simulated annealing algorithm implemented in the program Simwalk2. Using this method, we were able to assign haplotypes to 475 of the 485 genotyped subjects, including 284 of the 291 genotyped and clamped subjects, comprising 199 offspring and 85 offspring spouses. Founder haplotypes, i.e., those haplotypes from parents (48 spouses of probands) and individuals marrying into the families (116 spouses of offspring), were used to calculate haplotype frequencies in 328 chromosomes from 164 Mexican-American founders without CAD. The frequencies of the most common haplotypes are displayed in Table 4-1 along with the major allele frequencies of the six SNPs. The markers from Mexican Americans without CAD were used for haplotype frequency estimation in order to eliminate any disease-based ascertainment bias. Log-transformed (anthropometric measurements, fasting glucose, and fasting insulin) or square root-transformed (HOMA, GINF, and M) trait values were used to reduce skewness for all statistical analyses. Unpaired, two-sided t tests were used to compare trait values between men and women. Linkage was assessed using sibpair analysis. Age, sex, and BMI were specified as covariates in the linkage analysis. Among our subjects who were genotyped and clamped, we had available 252 sibpairs for linkage analysis.

As described above, association was evaluated by quantitative transmission disequilibrium testing for both individual polymorphisms and haplotypes using the QTDT program.

Results.

The clinical characteristics of the 291 subjects (112 men and 179 women) who had quantitative assessment of insulin resistance are shown in Table 4-2. This is an adult group of Mexican Americans of mean age 35.3 years. On average, these individuals are overweight. This may account for the degree of insulin resistance observed; however, it is known that Mexican Americans have a predisposition to visceral adiposity, hyperinsulinemia, and insulin resistance. The mean HOMA level suggests that these people are on average three to four times more insulin resistant than normal. The men had statistically significantly higher weight (P<0.00001) and fasting glucose (P=0.005) levels, while the women had significantly lower GINF (P=0.0001) but not M values. These differences remained significant among the 284 subjects who were clamped and haplotyped.

Of the several indexes of insulin sensitivity, linkage with LPL haplotypes was demonstrated only for the direct quantification represented by GINF (P=0.034). The M value, a clamp-derived index equal to GINF divided by body weight, was not significantly linked to LPL haplotypes (P=0.32). All other measures (fasting glucose, fasting insulin, and HOMA) were not significant (P=0.82, 0.44, and 0.34, respectively).

Association was evaluated by quantitative transmission disequilibrium testing. No haplotype was significantly associated with fasting glucose, fasting insulin, or HOMA, but both haplotypes 1 and 4 were significantly associated with GINF (haplotype 1, P=0.031; haplotype 4, P=0.007) and the M value (haplotype 1, P=0.031; haplotype 4, P=0.005). To characterize the nature of the associations of haplotypes 1 and 4 with insulin resistance, we determined the mean levels of insulin sensitivity in carriers of these haplotypes (Table 4-3 and FIG. 2). We observed that haplotype 1 is associated with the most favorable mean insulin sensitivity, while carriers of haplotype 4 had the lowest insulin sensitivity (i.e., the greatest insulin resistance). For fasting insulin, HOMA, GINF, and M, mean insulin sensitivity progressively deteriorated, going from haplotype 1 homozygotes to haplotype 1 heterozygotes to individuals without haplotype 1. Conversely, haplotype 4 heterozygotes were more insulin resistant than those without haplotype 4 (no haplotype 4 homozygotes were observed among the clamped subjects). FIG. 3 further explores these associations by independently examining the effects of haplotypes 1 and 4 on insulin sensitivity. Exclusion of subjects with haplotype 4 from haplotype 1 heterozygotes and those without haplotype 1 did not affect the trend of benefit on insulin sensitivity seen with increasing numbers of haplotype 1. Similarly, excluding haplotype 1 carriers from those without and with haplotype 4 did not affect the trend of lower insulin sensitivity in the latter subjects; in fact, the subjects without haplotype 1 who were carriers of haplotype 4 had the lowest insulin sensitivity (most insulin resistance) compared with the other haplogenotype groups. Similar trends were observed with M value (data not shown).

LPL haplotypes showed both linkage and association with insulin sensitivity in this study of Mexican Americans ascertained via a parent with CAD. The strength of this investigation is that we examined a population at high risk for the insulin resistance syndrome on clinical genetic epidemiologic grounds, that we directly quantified insulin sensitivity by the euglycemic clamp study, and that we combined this with the power of a haplotype-based analysis. The results suggest the presence of a common LPL haplotype in this population that protects against insulin resistance and a common haplotype that predisposes to insulin resistance. Of interest, our prior work indicated that these same LPL haplotypes appear to protect and predispose, respectively, to clinical CAD.

The clustering of insulin resistance, hypertension, central obesity, and dyslipidemia in the metabolic syndrome is receiving much attention as a risk factor for cardiovascular disease. The central component of this syndrome, insulin resistance, has been found to increase cardiovascular risk. In the San Antonio Heart Study, insulin resistance, estimated by HOMA, was an independent predictor of incident cardiovascular events over 8 years of follow-up. In the Helsinki Policemen Study, 970 men free of diabetes or CHD at baseline were followed for 22 years; those with the highest levels of insulin resistance, as estimated by insulin area under the curve during oral glucose tolerance testing, had the highest rates of CHD events and death.

LPL undergoes complex, tissue-specific regulation; for example, in the fed state, adipose LPL activity is increased and muscle LPL activity depressed, whereas the reverse is true in the fasting state. In insulin resistance/diabetes, macrophage LPL activity is increased and adipose LPL is decreased, with both alterations possibly contributing to atherosclerosis. The LPL haplotypes we have studied may contain variants that alter disease risk by affecting tissue-specific regulation of LPL activity. For example, one possibility is that haplotype 4 is associated with increased activity of LPL in muscle (promoting insulin resistance) and in macrophages (predisposing to atherosclerosis).

Most studies that have reported association of the LPL gene with insulin resistance used only surrogate measurements of insulin resistance, including fasting glucose, fasting insulin, and insulin area under the curve during oral glucose tolerance testing. One study evaluated the steady-state plasma glucose during the insulin suppression test. In addition, all except one of these studies only examined the association of the intronic restriction fragment-length polymorphisms PvuII and HindIII. Thus, current evidence that variation in LPL plays a role in insulin sensitivity has been indirect. Assessment of GINF during the hyperinsulinemic-euglycemic clamp study is widely regarded as the most direct physiologic measurement of insulin sensitivity. An analysis of indexes of insulin sensitivity in the Insulin Resistance Atherosclerosis Family Study showed that direct physiologic measurements of insulin sensitivity have a higher heritability than measures based on fasting values (such as HOMA).

Thus, use of physiologic indexes rather than simple fasting indexes should provide more power to discover genes that contribute to insulin sensitivity. Our study is the first that has used insulin sensitivity assessed by the euglycemic clamp as the phenotype in an association study with LPL. Consistent with the described higher heritability of physiologic indexes over fasting indexes, we showed a statistically significant association of LPL with GINF and M value but not with fasting glucose, fasting insulin, or HOMA. In addition, this study contains one of the largest family cohorts in the literature that have undergone the euglycemic clamp. We thus provide here statistical genetic evidence that LPL is an insulin resistance gene by demonstration of both linkage and association of LPL haplotypes with a direct quantitative measurement of insulin resistance in Mexican-American families ascertained via CAD. Whether these LPL haplotypes have the same relationship with insulin resistance in Mexican Americans without a family history of CAD or in other ethnic groups is unknown.

Two LPL haplotypes were associated with variation in GINF. These haplotypes had opposite effects on insulin sensitivity. Haplotype 1, the most common haplotype, was associated with improved insulin sensitivity. As the number of chromosomes in an individual with haplotype 1 decreased (from two, to one, to none), insulin sensitivity by GINF, as well as HOMA and fasting insulin, decreased progressively. Furthermore, haplotype 4 carriers had the lowest insulin sensitivity, i.e., they were the most insulin resistant. The direction of these associations persisted when the haplotypes were considered separately. The available data indicate that there is an insulin-sensitizing functional variant on haplotype 1 chromosomes and a variant on haplotype 4-bearing chromosomes that promotes insulin resistance. Current data does not allow us to distinguish whether the actual nucleotide locus responsible is the same for both haplotypes or whether such variation is at different locations in the gene. In terms of the relation to cardiovascular risk associated with the metabolic syndrome, our previous work has shown that haplotype 1 is associated with protection against CAD and that haplotype 4 may be associated with increased risk of CAD. By identifying whole chromosomal regions, haplotypes should have improved power and reproducibility in elucidation of disease-gene associations.

Multiple testing is an issue that applies to all genetic studies in which multiple genetic variants are tested for association against multiple traits. In such studies, including ours, adjusting for multiple comparisons by such methods as Bonferroni corrections are typically not utilized because they result in a significance level that is too stringent, particularly for detection of associations of moderate genetic effects. The principal reason we did not adjust for multiple testing is that our goal was to test the prior hypothesis that LPL haplotypes are associated with the most direct measure of insulin sensitivity, that defined by the euglycemic clamp. Upon finding significant association of LPL haplotypes with GINF, we then explored the associations with the other indexes of insulin sensitivity. The consistency of the trends in measures of insulin sensitivity in relation to the LPL haplotypes (FIG. 1) supports our association results.

In the study herein, a haplotype-based approach successfully identified linkage and association of variation in the LPL gene with a direct physiologic measurement of insulin sensitivity in Mexican Americans, providing strong evidence that LPL is an insulin resistance gene. Given prior work demonstrating association of single variants with atherosclerosis, dyslipidemia, obesity, and hypertension, the haplotypes described here should be used in future studies exploring the association of the LPL gene with components of the insulin resistance syndrome, especially in the Mexican-American population.

Tables

TABLE 4-1

LPL single marker and haplotype frequencies in Mexican Americans

| SNPs and major allele frequencies | 7315 G→C 0.89 | 8292 A→C 0.85 | 8393 T→G 0.80 | 8852 T→G 0.78 | 9040 C→G 0.93 | 9712 G→A 0.88 | Chromosomes | Frequency (%) |
|---|---|---|---|---|---|---|---|---|
| Haplotype 1 | G | A | T | T | C | G | 206 | 62.8 |
| Haplotype 2 | G | C | T | T | C | G | 50 | 15.2 |
| Haplotype 3 | C | A | G | G | C | A | 33 | 10.1 |
| Haplotype 4 | G | A | G | G | G | G | 22 | 6.7 |
| Haplotype 5 | G | A | G | G | C | A | 8 | 2.4 |
| Haplotype 6 | G | A | T | G | C | G | 6 | 1.5 |
| Haplotype 7 | C | A | G | G | C | G | 2 | 0.5 |
| Haplotype 8 | G | A | G | G | C | G | 1 | 0.3 |

TABLE 4-2

Clinical characteristics of 291 genotyped and clamped individuals

| | Men | Women |
|---|---|---|
| n | 112 | 179 |
| Age (years) | 35 ± 9.4 (19-60) | 35.5 ± 8.2 (18-58) |
| Weight (kg)* | 84.2 ± 15.6 (52.5-126.6) | 72.1 ± 14.0 (38.6-128.5) |
| Body mass index (kg/m$^2$) | 28.9 ± 4.8 (17.8-45.4) | 29.1 ± 5.5 (18.1-54.8) |
| Fasting glucose (mg/dl)† | 96.1 ± 9.8 (74.0-118.0) | 92.5 ± 9.4 (56.0-117.0) |
| Fasting insulin (μIU/ml) | 15.4 ± 8.9 (5.0-62.0) | 15.5 ± 7.5 (2.0-49.0) |
| HOMA | 3.7 ± 2.4 (1.2-15.9) | 3.6 ± 1.9 (0.5-14.0) |
| GINF (mg/min)‡ | 428.6 ± 196.8 (105.9-1031.5) | 343.5 ± 147.5 (20.7-1010.5) |
| M (mg · kg$^{-1}$ · min$^{-1}$) | 5.4 ± 2.8 (1.0-13.9) | 5.0 ± 2.4 (0.2-14.9) |

Data are mean ± SD (range). Comparing men versus women,
*P < 0.00001,
†P = 0.005,
‡P = 0.0001.

TABLE 4-3

LPL haplotype means for indexes of insulin sensitivity

| Haplotype carriers | Fasting glucose (mg/dl) | Fasting insulin (μIU/ml) | HOMA | GINF (mg/min) | M (mg · kg$^{-1}$ · min$^{-1}$) |
|---|---|---|---|---|---|
| 1 (n = 239) | 93.8 | 14.0 | 3.0 | 365.0* | 5.3* |
| 2 (n = 85) | 95.2 | 14.6 | 3.1 | 365.9 | 4.9 |
| 3 (n = 56) | 94.9 | 14.5 | 3.1 | 345.1 | 4.7 |
| 4 (n = 40) | 98.8 | 15.5 | 3.2 | 344.3* | 4.6* |

*Significant association of phenotype with haplotype (see text).

Example 5

The 3' Untranslated Region of the Lipoprotein Lipase Gene

Haplotype Structure and Association with Post-Heparin Plasma Lipase Activity

Example 5 sequenced LPL exon 10 from insulin-sensitive and insulin-resistant individuals with relevant LPL haplotypes to describe the polymorphism and haplotype structure of the 3' UTR of LPL, and 2) compared the post-heparin plasma LPL activity of subjects with different haplotypes to examine the potential functional significance of this LPL variation. To provide additional confirmation of the physiological relevance of LPL haplotypes, secondary association analyses were conducted with multiple phenotypes related to the metabolic syndrome.

The University of California, Los Angeles/Cedars-Sinai Mexican-American Coronary Artery Disease (MACAD) Project enrolled families ascertained through a proband (parent) with CAD, determined by evidence of myocardial infarction on electrocardiogram or hospital record, evidence of atherosclerosis on coronary angiography, or history of coronary artery bypass graft or angioplasty. Two generations were enrolled into the study: 1) the proband and proband spouses (parental generation) and 2) their adult (age 18 yr or older) offspring and the spouses of those offspring (offspring generation). All subjects were genotyped, and only the offspring generation was phenotyped. By design, the offspring were free of diabetes and clinically manifest cardiovascular disease, thus avoiding secondary changes in phenotype caused by overt disease. In the present study, 891 subjects from 163 families were genotyped; of these, 497 adult offspring and offspring spouses had undergone assessment of post-heparin plasma LPL activity at the time of the analyses reported herein. Insulin sensitivity was determined using the euglycemic-hyperinsulinemic clamp, which yields the M value; higher M values indicate higher sensitivity to insulin, and lower M values indicate insulin resistance.

Subject Selection for Sequencing

We initially planned to sequence exon 10 in a minimum of 12 subjects from the MACAD population, to give us a 99% power to detect at least one polymorphism with an allele frequency of 10%. Ideally, we would have selected four insulin-resistant subjects with haplogenotype 4/4, four insulin-sensitive subjects with haplogenotype 4/4, and four insulin sensitive subjects with haplogenotype 1/1. However, the offspring generation contained no haplotype 4/4 homozygotes. Therefore, we initially sequenced exon 10 in four insulin-sensitive subjects of haplogenotype 1/1 (mean M, 9.17 mg/kg·min), four insulin-resistant subjects of haplogenotype 1/4 (mean M, 2.23 mg/kg·min), and four insulin-sensitive subjects with haplogenotype 1/4 (mean M, 8.46 mg/kg·min); subjects were unrelated. This strategy of sequencing subjects with divergent genotypes and divergent phenotypes was chosen to maximize the chance of identifying variation with a functional impact. Six parents of four individuals were sequenced to facilitate identification of the haplotype phase of identified variants.

To completely characterize the haplotype structure of LPL exon 10, we also sequenced subjects carrying haplotypes 2, 3, and 5 (without consideration of phenotype). Haplotypes 2 and 3 were sufficiently common in the cohort to provide homozygotes for sequencing. Two haplotype 2 homozygotes and three haplotype 3 homozygotes were sequenced. To sequence the rarer haplotype 5 (founder frequency of 2.4%), we selected three subjects of haplogenotype 1/5.

Sequencing Methodology

We sequenced the 1949-bp sequence of exon 10 as well as 65 bp of upstream and 63 bp of downstream genomic sequence. This sequence was divided into four overlapping segments. PCR was used to amplify each fragment; the PCR primer sequences are as follows: forward 5'-CAGGCGG-GAATTGTAAAACA-3' (SEQ ID NO:26) and reverse 5'-TTGACGTCTGGACCACATTC-3'(SEQ ID NO:27); forward 5'-CTGGATCTTTCGGACTGAGG-3' (SEQ ID NO:28)and reverse 5'-CAGGAACCTCTCCACCCTTT-3' (SEQ ID NO:29); forward 5'-TTCCAGT-GCGTCTCTTTTGTT-3' (SEQ ID NO:30)and reverse 5'-AT-TCCAAGCCTGATGATGTT-3' (SEQ ID NO:31); and forward 5'-TTGTTCCTGATGTGCCAGAA-3' (SEQ ID NO:32)and reverse 5'-TGCTGAGTGAATCTGACCTAA-GAA-3' (SEQ ID NO:33). Each amplified segment was sequenced in both directions using BigDye Terminator v3.1 Cycle Sequencing (Applied Biosystems, Foster City, Calif.). Sequence was determined on an ABI 377 automated sequencer. Variation was identified by comparison to the reference sequence from GenBank (NT_030737). At this time, the National Center for Biotechnology Information's dbSNP build 123 lists 21 SNPs in LPL exon 10.

Genotyping and Haplotype Determination

We designed PCR primers and TaqMan™ minor groove binder (MGB) (Applied Biosystems) probes to genotype the following exon variants identified from sequencing exon 10: rs11570891, rs4922115, rs3289, rs11570892, rs1803924, rs1059507, rs3735964, rs3200218, rs13702, rs1059611, rs10645926, rs15285, and rs3866471 (Table 5-1). We were unable to design suitable probes for the SNP rs3208305 because it is immediately adjacent to a polyadenine (polyA) tract. We also could not design probes for the uncharacterized insertion/deletion. Thus, of the 15 variants identified by sequencing exon 10, we genotyped 13.

These 13 exon 10 SNPs identified by sequencing were genotyped in 891 subjects using the 5'-exonuclease assay (TaqMan™ MGB) described previously. The genotypes of 44 subjects were dropped because their genotypes were incompatible with their family pedigree, as detected by Pedcheck. The original six LPL 3'-end SNPs, rs312, rs319, rs320, rs327, rs328, and rs330 (designated 7315, 8292, 8393, 8852, 9040, and 9712, respectively, in previous publications), were also genotyped in these subjects; therefore, 847 subjects from 163 families were genotyped at all 19 LPL variants. PCR primers and TaqMan™ MGB probes for these latter six SNPs were previously reported.

Haploview 3 was used to determine haplotypes as well as delineate haplotype blocks. Haploview constructs haplotypes by using an accelerated expectation maximization algorithm similar to the partition/ligation method, which creates highly accurate population frequency estimates of the phased haplotypes based on the maximum likelihood derived from the unphased input genotypes. Of the 847 subjects genotyped at all 19 LPL variants, 810 were assigned a haplogenotype (i.e. two haplotypes). Haploview was used to calculate linkage disequilibrium (LD, the D' statistic) between each pairwise combination of all 19 SNPs used in haplotype block determination. Haploview was then used to assign haplotype blocks using a variant of the four-gamete rule.

Phenotyping

For post-heparin lipase activity determination, subjects were asked to come to the General Clinical Research Center after fasting for 12 h. Subjects who had evidence of anemia on complete blood count, evidence of hematuria on urinalysis, or a positive pregnancy test were excluded. Eligible subjects received an iv bolus of heparin (60 U/kg), followed by collection of post-heparin blood 10 min later. Administration of heparin to subjects releases both LPL and hepatic lipase (HL) from capillary endothelial cells, allowing their collection in peripheral blood. Blood samples are then assayed for lipase activity by measuring the lipolysis of a radiolabeled triolein substrate, yielding activity resulting from the action of both LPL and HL. Because high-salt conditions inhibit LPL activity but not HL activity, LPL activity is then derived from the difference of total lipase activity and that activity determined in the presence of 1 m NaCl. When this study was performed, 497 subjects from the offspring generation had undergone post-heparin lipase activity determination. Of these, 397 subjects from 112 families had been haplotyped at the 19 LPL markers.

Phenotypes relevant to the metabolic syndrome, including body mass index (BMI), waist and hip measurements, fasting lipid profile, apolipoproteins, fasting insulin, fasting and postprandial glucose measurements, and hyperinsulinemic-euglycemic clamp were performed as previously described.

Association Analysis

Association of lipase activity and metabolic phenotypes with LPL 3'-end variants was evaluated using a robust variance estimation approach, employing the generalized estimating equation (GEE1) (to test hypothesized associations between phenotypes and haplotypes while accounting for familial correlations present in the family data. The PROC GENMOD procedure in SAS (version 8.0; SAS Institute, Cary, N.C.) was used for the analysis using the GEE1 model. Family was taken as the cluster factor; i.e. members from the same family were assumed to be correlated, and those from different families were assumed to be independent. Age, sex, and BMI were included as covariates in all analyses, except when indices of adiposity were being analyzed for association, in which case only age and sex were taken as covariates. Quantitative trait values were log or square root transformed as appropriate to reduce skewness.

Results

Sequencing Haplotypes 1 and 4

Sequencing of 12 individuals (and six parents) with haplotypes 1 and 4 and extremes of insulin sensitivity identified 10 variants, composed of eight SNPs (rs11570891, rs3289, rs3208305, rs1803924, rs3735924, rs13702, rs1059611, and rs15285), one two-nucleotide insertion/deletion (rs10645926), and another insertion/deletion. The latter insertion/deletion could not be characterized because it was not present in the homozygous state in any of the subjects sequenced. One SNP (rs11570891) was 11 bp proximal to exon 10.

Sequencing Common LPL Haplotypes Other than 1 and 4

Sequencing of haplotypes 2, 3, and 5 yielded five additional SNPs that were not identified on haplotypes 1 or 4. Of the LPL exon 10 SNPs listed in dbSNP, seven were not found on chromosomes defined by the most common LPL 3'-end (intron 7 to intron 9) haplotypes 1 through 5 in this population.

Haplotype Structure

Table 5-2 shows the frequency and position information of the 19 LPL variants based on genotyping in the 847 subjects genotyped for all 19 variants. The haplotypes constructed based on these 19 variants [six original LPL SNPs and the 13 exon 10 variants (12 SNPs and the TT insertion)] are listed in Table 5-3, along with their respective frequencies. These haplotypes are labeled 19-1, 19-2, 19-3, etc. to denote that they are based on a total of 19 polymorphisms, and to avoid confusion with the original six-SNP-based haplotypes 1, 2, 3, 4, etc. The haplotypes (19-1 to 19-7) occurring at a frequency of greater than approximately 1% were identical to those predicted from the exon 10 sequencing. These seven haplotypes together comprise 94% of the haplotypes found in this population. The original six-SNP-based haplotypes are also listed in Table 5-3, in rows corresponding to the new 19-SNP-based haplotypes. The latter shows that haplotype 1 was subdivided into three new haplotypes; however, one haplotype (19-1) remained common, whereas the new sub-haplotypes (19-5 and 19-7) occurred with low frequency. The other common haplotypes were extended 3' into exon 10 without generating new haplotypes. Linkage disequilibrium (D') ranged from 0.04-1, and haplotype block determination showed that the 19 SNPs lie in two haplotype blocks (FIG. 1). The exon 10 variants are entirely included in the large 3'-end block.

Association of LPL Haplotypes with LPL Enzyme Activity

Figure 6:
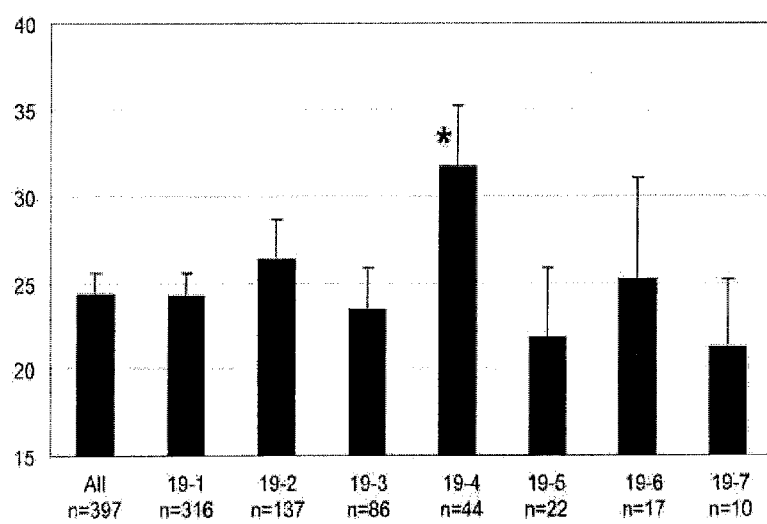
FIG. 6 is a graph showing LPL activity means according to haplotype carrier status. *, Significant association of LPL activity with haplotype by GENMOD. Error bars represent SE. LPL activity is expressed in mU/ml, where I U of LPL activity represents one μmol of FFA released per minute.
Figure 7:
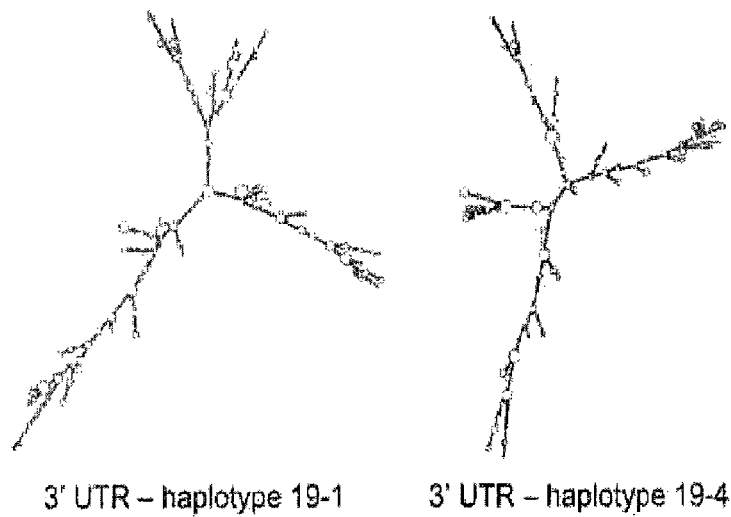
FIG. 7 shows RNA secondary structure prediction of 3' UTR sequences. The 3' UTR regions of haploytpes 19-1 and 19-4 are shown. RNA secondary structure prediction of 3' UTR sequences. The 3' UTR regions of haplotypes 19-1 and 19-4 are shown. RNA secondary structure prediction was made through energy minimization.

Of the common haplotypes, haplotype 19-4 showed association with LPL activity (P=0.025). FIG. 6 shows the mean LPL activity level for carriers of each of the most common haplotypes. Haplotype 19-4 is associated with elevated LPL activity. The mean LPL activity level in the whole haplotyped population was 24.4 mU/ml (1 U=1 µmol of FFA released per minute). Carriers of haplotype 19-4 had a mean post-heparin LPL activity level of 31.8 mU/ml, whereas subjects without haplotype 19-4 had a mean LPL activity of 23.4 mU/ml.

Haplotype 19-6, which appears to have arisen by recombination between haplotypes 19-3 and 19-4, is composed of the 5' end of haplotype 19-4 and the 3' end of haplotype 19-3. The fact that the mean lipase activities of 19-3 and 19-6 were similarly lower than the lipase activity of 19-4 (FIG. 2) suggests that the variant(s) that increase lipase activity lie on the distal haplotype of 19-4.

Association of LPL Haplotypes with Metabolic Traits

Given the association of haplotype 19-4 with LPL activity, we next evaluated the physiological relevance of this finding by assessing the association of haplotype 19-4 with multiple lipid, apolipoprotein, adiposity, insulin resistance, and blood pressure traits. Haplotype 19-4 was associated with increased BMI, high-density lipoprotein cholesterol (HDL-C), apolipoprotein A-I, apolipoprotein A-II, and systolic blood pressure and with decreased insulin sensitivity (M value) (Table 5-4).

Discussion

We determined in detail the haplotype structure of exon 10 of LPL and demonstrated the potential functional significance of these haplotypes in terms of whole-body postheparin LPL enzyme activity and metabolic phenotypes. These haplotypes will be an important tool for future genetic analyses involving LPL. Because LPL is a highly polymorphic gene, an understanding of the haplotype structure of LPL is critical to meaningful use of these variants in genotype phenotype association analyses.

The LPL gene is approximately 30 kb in genomic length and is composed of 10 exons (nine introns). The 10th exon is large (1949 bp) and codes for an approximately 2-kb (1948-bp) 3' UTR, which makes up over half of the mature LPL mRNA. The LPL enzyme hydrolyzes triglycerides in circulating very low-density lipoprotein (VLDL) cholesterol and chylomicrons, providing FFAs and monoacylglycerol for use by the surrounding target tissues. LPL is located in capillary endothelium and is most abundant in adipose tissue and cardiac and skeletal muscle but is also found in other tissue types of relevance, such as vascular wall monocytes.

Our efforts were focused on the 3' end of the LPL gene because polymorphisms in the 3' end, such as HindIII, have been associated with insulin resistance and with atherosclerosis. We previously took advantage of the well characterized catalog of SNPs in the 3' end of the LPL gene (intron 6 to intron 9), to construct haplotypes to use in association analysis against insulin resistance and atherosclerosis. Once associated haplotypes were found, we searched for functional variants by sequencing exon 10 in subjects with these haplotypes. When our study began, exon 10 had not been as rigorously sequenced as the region from exon 4 to exon 9. Our hypothesis is that functional variation in the 3' UTR (encoded by exon 10) may influence these phenotypes by altering translation of LPL. The high degree of sequence homology (75%) between human and mouse 3' UTR suggests that the LPL 3' UTR has functional significance.

Experimental evidence that the 3' UTR plays a role in regulating translation of LPL comes from studies in rodents. Kern and colleagues implicated a role for the 3' UTR in LPL translation regulation in the setting of diabetes. Induction of diabetes by streptozocin treatment in rats led to a 75% decrease in LPL activity and synthesis with no change in the mRNA level and no change in the amount of mRNA associated with polysomes (no inhibition of translation initiation). Cytoplasmic extracts from diabetic rat adipose tissue inhibited in vitro translation if 1818-2000 of the LPL 3' UTR was present. Gel shift studies suggested a protein in diabetic adipose extract binds there and inhibits LPL translation. Insulin-treated rats had increased LPL toward normal.

Indirect evidence that the 3' UTR may affect LPL translation in humans comes from studies in transgenic mice expressing human LPL specifically in adipose tissue. Two transgenic constructs were used, one containing the entire coding sequence of human LPL and the 3' UTR, and another containing the coding sequence of human LPL with only the distal approximately 750 nucleotides of the 3' UTR. The proximal 3' UTR was deleted in light of the above experimental evidence on the importance of this region in LPL translation regulation. Both sets of transgenic mice overexpressed human LPL 2-fold, but the 3' UTR deletion mice did so with a much lower level of human LPL mRNA, suggesting that deletion of the 3' UTR resulted in a translationally unrepressed LPL. Whether the 3' UTR truly plays a role in humans remains to be determined. We investigated this question with a population genetic, haplotype based approach.

We found that haplotype 19-4 was associated with postheparin LPL activity. The minor alleles of six variants (rs328, rs11570891, rs1803924, rs3735964, rs1059611, and rs10645926), the latter five of which were identified by sequencing exon 10, are found uniquely on haplotype 19-4. These 3' UTR variants are candidates for variants that alter the expression of LPL and thus influence LPL activity. Some investigators but not others have successfully identified association of LPL polymorphisms with post-heparin LPL activity. Our data do not allow us to distinguish whether one of these SNPs has a functional impact on LPL expression or whether several or all the SNPs acting together affect LPL expression. Ser447Stop (rs328 or 9040), the rare allele of which is found only on haplotype 19-4 (Table 5-3), has in many but not all studies been associated with increased LPL activity both in population genetic studies and in in vitro experimentation that has suggested either increased specific activity or increased secretion of catalytically normal LPL. At this time, researchers do not agree on the exact molecular consequences of the 447Stop variant, which truncates only the last two amino acids from the enzyme. We suggest that effects of this SNP on LPL activity may be a manifestation of the linkage disequilibrium with functional variants in the 3' UTR. The finding of normal enzyme activity with increased production is consistent with increased translation mediated by 3' UTR variation that is linked to 447Stop (in a model where 447Stop is nonfunctional).

Additional evidence of the physiological relevance of haplotype 19-4 came from secondary analyses demonstrating association with multiple metabolic traits. As would be predicted on the basis of increased LPL activity, haplotype 19-4 was associated with increased HDL-C and a trend to decreased triglycerides. Apolipoproteins A-I and A-II, the major lipoproteins of HDL particles, were both increased by haplotype 19-4, with a decreased A-I/A-II ratio (Table 5-4). The relative increase in apolipoprotein A-II may explain the association of haplotype 19-4 with insulin resistance and atherosclerosis, despite the higher HDL-C levels. Transgenic mice overexpressing apolipoprotein A-II have skeletal muscle insulin resistance and accelerated atherosclerosis; HDL particles from these mice exhibit proinflammatory and prooxidant properties.

Post-heparin plasma LPL activity measures whole-body LPL activity and therefore does not provide information on tissue-specific effects of haplotype 19-4. LPL is known to have complex, tissue-specific regulation; for example, in the fed state, adipose LPL activity is increased and muscle LPL activity is decreased. We hypothesize that haplotype 19-4 promotes insulin resistance by increasing LPL activity and FFA uptake in skeletal muscle, promotes atherosclerosis and hypertension by increasing LPL activity in vessel wall macrophages, and increases adipose tissue LPL activity promoting fat storage and obesity; however, specific study of LPL activity in such tissues isolated from carriers of haplotype 19-4 will be needed to confirm these hypotheses.

Figure 2:
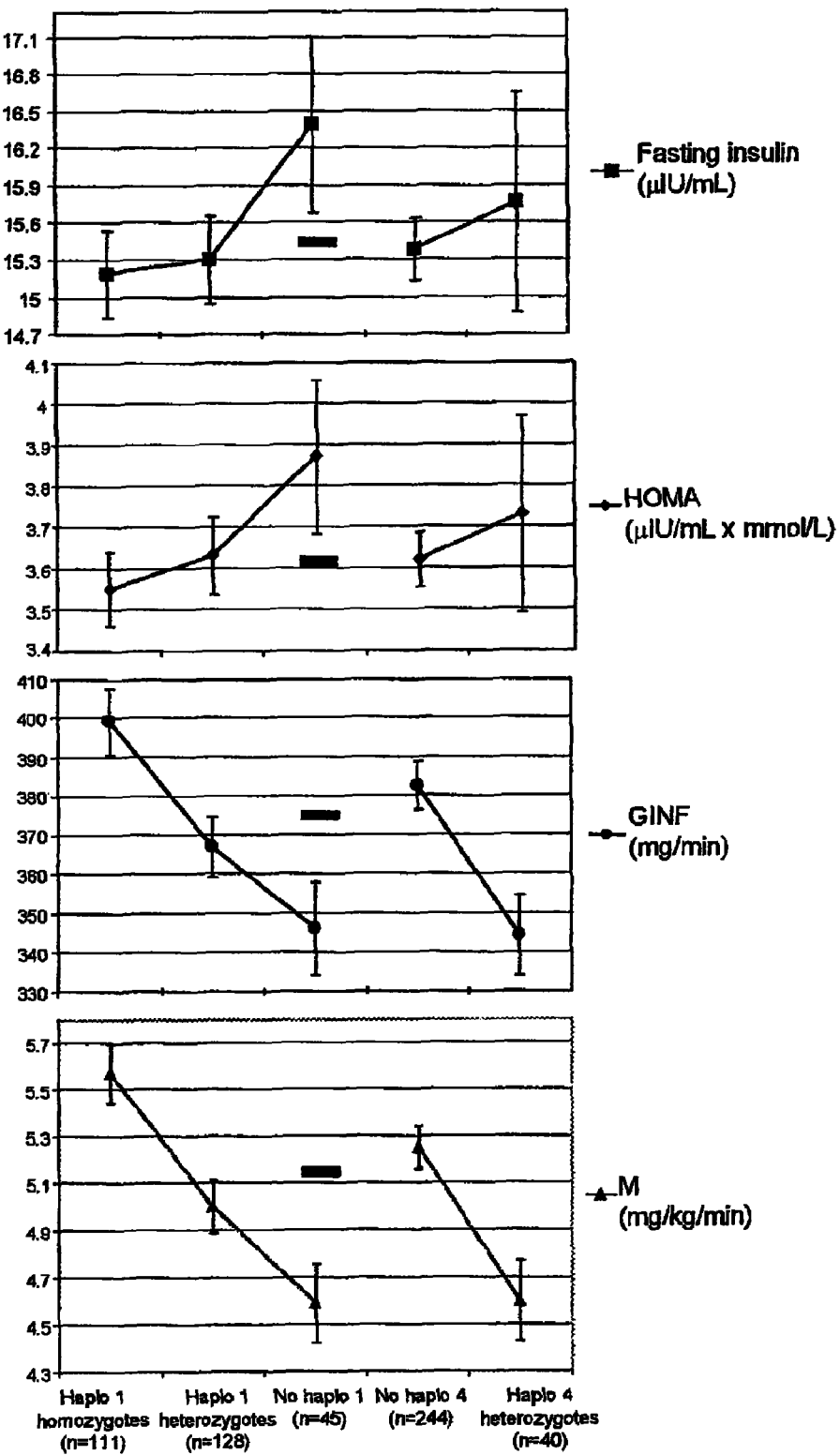
FIG. 2 shows the effect of LPL 3'-end haplotypes on indices of insulin sensitivity. The thick line in the center of each graph represents the mean for the entire haplotyped and clamped population.
Figure 3:
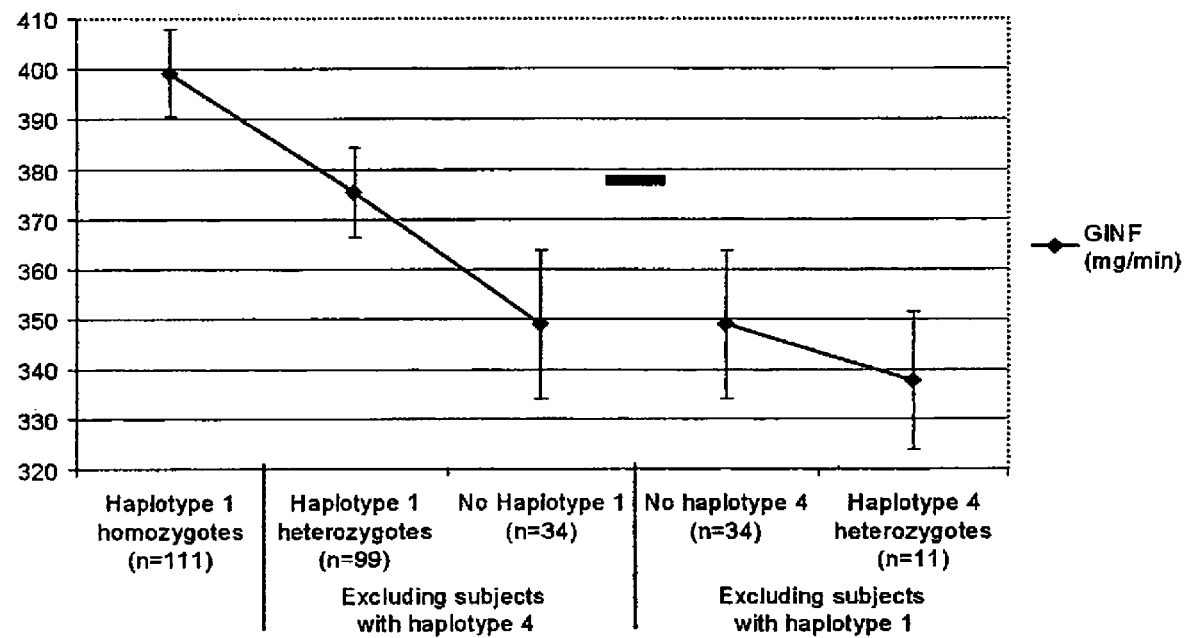
FIG. 3 shows independent effects of haplotype 1 and haplotype 4 on insulin sensitivity. On the left are haplotype 1 genotypes with haplotype 4 carriers removed. On the right are haplotype 4 genotypes with haplotype 1 carriers removed. The thick line in between represents the mean GINF level for the entire haplotyped and clamped population.
Figure 4:
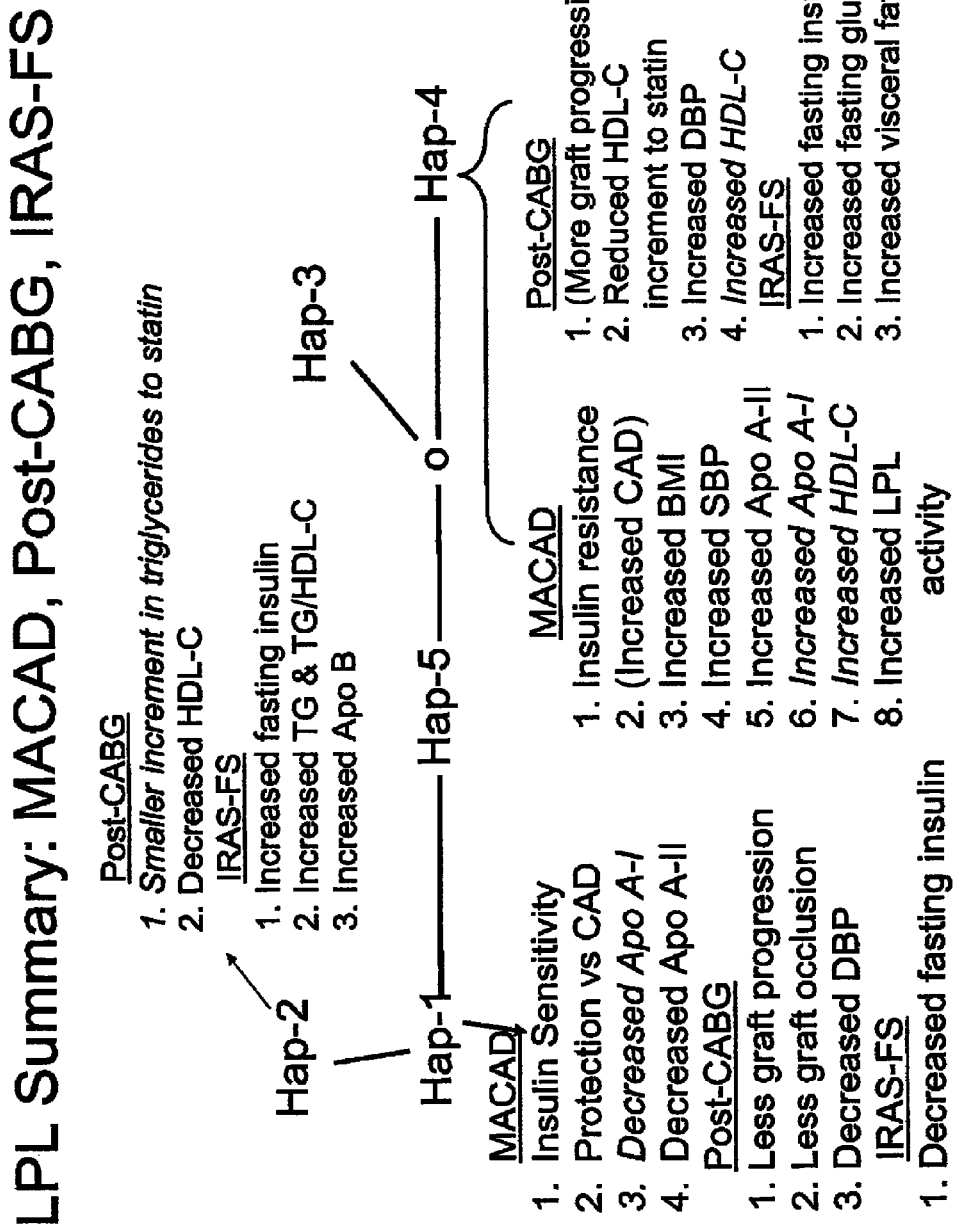
FIG. 4 is a summary of selected characteristics of haplotypes.
Figure 5:
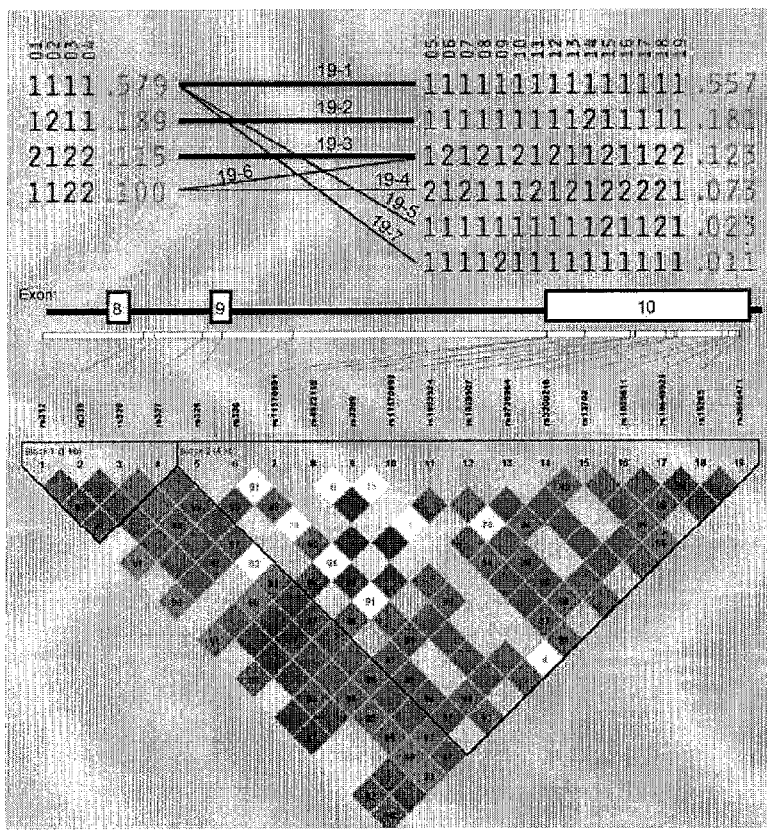
FIG. 5 shows a haplotype block structure defined by 19 LPL variants spanning intron 7 to exon 10. Top, Common (>1% frequency) haplotypes found in each of two haplotype blocks based on 19 LPL variants spanning intron 7 to exon 10. Haplotype frequencies are displayed as well as how the haplotypes map between the two blocks. The number 1 indicates the major allele at each SNP, 2 the minor allele. Bottom, Linkage disequilibrium plot. D' values are indicated (percent). The dark solid blocks indicates D'=1 for the corresponding pair of variants. The lighter solid boxes also indicate D'=1, but with a low confidence score.

Although not allowing us to determine which exon 10 variant or combination thereof on haplotype 19-4 affects LPL expression, our data do exclude the first four (introns 7 to 8) variants of the 5'-end haplotype block because subjects who differed only at this haplotype segment (those with 19-3 and 19-6) had similar post-heparin lipase activities (FIG. 2). The 3'-end haplotype segment of 19-4 appeared uniquely associated with elevated lipase activity. Ser447Stop and the five exon 10 variants unique to haplotype 19-4 lie on this distal segment.

In an additional effort to assess the potential functional relevance of the five exon 10 variants unique to haplotype 19-4, we determined whether these polymorphisms lie in regions that display conservation with exon 10 across species, because conserved sequences are likely to be functionally important. We used the VISTA Browser, accessed from the Berkeley Programs for Genomic Applications (PGA) website (http://pipeline.lbl.gov/cgi-bin/gateway2), to identify conserved regions between the human LPL 3' UTR and that of the mouse, rat, and chicken. SNPs rs3735964 and rs1059611 and the dinucleotide insertion rs10645926 were conserved across species.

The sequence context of the SNPs found by sequencing was examined for known functional motifs from other genes whose expression is regulated by the 3' UTR, using the database of functional UTR motifs available at UTRdb (http://bighost.area.ba.cnr.it/BIG/UTRHome/). None of the SNPs we identified by sequencing exon 10 was found in a known functional motif. We also did not find the occurrence of these exon 10 variants in the polyadenylation signals (the hexanucleotide AAUAAA) or polyadenylation sites in exon 10.

A final indication that variation in the LPL 3' UTR may have a functional impact comes from RNA secondary structure prediction. We compared the secondary structure of the reference sequence (major allele at all SNP sites) with that of haplotype 19-4 using the Vienna RNA Package and found a clear difference in secondary structure between the two (FIG. 3). This raises the possibility that an entire collection of variants may influence LPL translation by altering access of RNA binding proteins to the 3' UTR.

The database approaches above suggest but in no way prove that a particular SNP or group of SNPs has an actual functional impact on LPL expression. However, this information will be useful in prioritizing which variants to pursue in in vitro functional studies. Of up to 21 SNPs in exon 10 (14 found on sequencing, seven others found only in dbSNP), our association results have narrowed to five the number of exon 10 variants that need to be tested in in vitro systems for their effect on LPL expression. Combined with the information from conserved regions in other species, the variants rs3735964, rs1059611, and rs10645926 have the highest priority for functional testing.

Tables

TABLE 5-1

Table 1. Primers and probe sequences used in the 5'-exonuclease assay

| Variant | | PCR primers |
|---|---|---|
| rs11570891 | Forward | 5'-CAGGCGGGAATTGTAAAACAC-3'//SEQ ID NO: 34; |
| | Reverse | 5'-TTGTTCTGTAGATTCGCCCAGTT-3'//SEQ ID NO: 35 |
| rs4922115 | Forward | 5'-CACTCAGAAGATAATAAATTGCCCTTT-3'//SEQ ID NO: 36; |
| | Reverse | 5'-CACATGCCGTTCTTTGTTCTGT-3'//SEQ ID NO: 37 |
| rs3289 | Forward | 5'-GGCGTATTGGGCCATAGC-3'//SEQ ID NO: 38; |
| | Reverse | 5'-AAGGCCTCAGTCCGAAAGATC-3'//SEQ ID NO: 39 |
| rs11570892 | Forward | 5'-TTGAAAATGAGCCTGTAATCC-3'//SEQ ID NO: 40; |
| | Reverse | 5'-TTTTTTCTGCACCATTCAAA-3'//SEQ ID NO: 41 |
| rs1803924 | Forward | 5'-ACACATAATTTGAATGGTGCAGAAA-3'//SEQ ID NO: 42; |
| | Reverse | 5'-TCAGATATTGAATGATTTTAAATTGATGAA-3'//SEQ ID NO: 43 |
| rs1059507 | Forward | 5'-CAATGAGCCAGATGGAGTACCA-3'//SEQ ID NO: 44; |
| | Reverse | 5'-GTTCACTCACTCTTGATTAGTTGTTAAAAC-3'//SEQ ID NO: 45 |

TABLE 5-1-continued

Table 1. Primers and probe sequences used in the 5'-exonuclease assay

| | | |
|---|---|---|
| rs3735964 | Forward | 5'-CAACTAATCAAGAGTGAGTGAACAACTATTT-3'//SEQ ID NO: 46; |
| | Reverse | 5'-GAGATATTTGACATCTTTATCATTTCATATTTATAC-3'//SEQ ID NO: 47 |
| rs3200218 | Forward | 5'-CCTATTTTTCAGAATGCTCTTCTACGTA-3'//SEQ ID NO: 48; |
| | Reverse | 5'-AGTCGGGTTCCCAGCTATAGC-3'//SEQ ID NO: 49 |
| rs13702 | Forward | 5'-CAGCACATAGCACTGGGAACTC-3'//SEQ ID NO: 50; |
| | Reverse | 5'-AGCTCCATTTACACATCCACACA-3'//SEQ ID NO: 51 |
| rs1059611 | Forward | 5'-ATGTTCTGGCTTTACATTTTATTTATTAGC-3'//SEQ ID NO: 52; |
| | Reverse | 5'-GCCACAATGACCTTTCCAATATG-3'//SEQ ID NO: 53 |
| rs10645926 | Forward | 5'-GGTCATTGTGGCTATCTGCATTT-3'//SEQ ID NO: 54; |
| | Reverse | 5'-GCTCTGTGAGACCATCACTGATAAA-3'//SEQ ID NO: 55 |
| rs15285/ | Forward | 5'-GTGTCTTTATCAGTGATGGTCTCACA-3'//SEQ ID NO: 56; |
| rs3866471 | Reverse | 5'-TTCTGTTTTGTTAAAGCCCATTTC-3'//SEQ ID NO: 57 |
| rs15285/ | Forward | 5'-GTGTCTTTATCAGTGATGGTCTCACA-3'//SEQ ID NO: 58; |
| rs3866471 | Reverse | 5'-CTTTCTTGTTTTGTTAAAGCCCATT-3'//SEQ ID NO: 59 |
| Variant | TaqMan MGB probes | |
| rs11570891 | Forward | 5'-CTGAGAAAAAgCACAGGA-3'//SEQ ID NO: 60; |
| | Reverse | 5'-TGAGAAAAAaCACAGGAA-3'//SEQ ID NO: 61 |
| rs4922115 | Forward | 5'-AAACTGGGCgAATC-3'//SEQ ID NO: 62; |
| | Reverse | 5'-AAACTGGGCaAATC-3'//SEQ ID NO: 63 |
| rs3289 | Forward | 5'-CAGAATTCCAaTTAA-3'//SEQ ID NO: 64; |
| | Reverse | 5'-CCATGAATTCCAgTTAA-3'//SEQ ID NO: 65 |
| rs11570892 | Forward | 5'-TCAGCTGACACaTA-3'//SEQ ID NO: 66; |
| | Reverse | 5'-TCAGCTGACACgTA-3'//SEQ ID NO: 67 |
| rs1803924 | Forward | 5'-TAGATTCTCcAAATGAT-3'//SEQ ID NO: 68; |
| | Reverse | 5'-ATTAGATTCTCtAAATGATT-3'//SEQ ID NO: 69 |
| rs1059507 | Forward | 5'-AACAAATAgCAACCCT-3'//SEQ ID NO: 70; |
| | Reverse | 5'-AACAAATAaCAACCCTC-3'//SEQ ID NO: 71 |
| rs3735964 | Forward | 5'-AGAATGCTCTTcTACG-3'//SEQ ID NO: 72; |
| | Reverse | 5'-CAGAATGCTCTTaTACG-3'//SEQ ID NO: 73 |
| rs3200218 | Forward | 5'-TGATAAAGaTGTCAAATAT-3'//SEQ ID NO: 74; |
| | Reverse | 5'-ATAAAGgTGTCAAATAT-3'//SEQ ID NO: 75 |
| rs13702 | Forward | 5'-CTCCGAAAAACTTTGtTATA-3'//SEQ ID NO: 76; |
| | Reverse | 5'-TCCGAAAAACTTTGcTATA-3'//SEQ ID NO: 77 |
| rs1059611 | Forward | 5'-CAAGCTCCaTTTACAC-3'// SEQ ID NO: 78; |
| | Reverse | 5'-CAAGCTCCgTTTACA-3'//SEQ ID NO: 79 |
| rs10645926 | Forward | 5'-ACACATACaGTTAGCACC-3'//SEQ ID NO: 80; |
| | Reverse | 5'-ACACATACaaaGTTAGCA-3'//SEQ ID NO: 81 |
| rs15285/ | Forward | 5'-CCAACTcAcTCTTATG-3'//SEQ ID NO: 82; |
| rs3866471 | Reverse | 5'-AGCCAACTtAcTCTTAT-3'//SEQ ID NO: 83 |
| rs15285/ | Forward | 5'-CCAACTcAaTCTTATG-3'//SEQ ID NO: 84; |
| rs3866471 | Reverse | 5'-AGCCAACTtAaTCTTAT-3'//SEQ ID NO: 85 |

A MGB and nonfluorescent quencher is present at the 3' end of all probes. In the probe sequences, variant nucleotides are indicated in lowercase and bold. Note two variants (rs15285 and rs3866471) are bold in the last two probe pairs; consideration of the results from both reactions allows genotyping of the two neighboring SNPs.

TABLE 5-2

Frequency and position information on 19 LPL variants.

| Variant designation | Variation | Location | Position | MAF |
|---|---|---|---|---|
| rs312 (7315) | G/C | Intron 7 | −4822 | 0.12 |
| rs319 (8292) | A/C | Intron 8 | −3845 | 0.19 |
| rs320 (8393)$^\alpha$ | T/G | Intron 8 | −3744 | 0.21 |
| rs327 (8852) | T/G | Intron 8 | −3285 | 0.23 |
| rs328 (9040)$^\alpha$ | C/G | Exon 9 | −3097 | 0.073 |
| rs330 (9712) | G/A | Intron 9 | −2425 | 0.13 |

TABLE 5-2-continued

Frequency and position information on 19 LPL variants.

| Variant designation | Variation | Location | Position | MAF |
|---|---|---|---|---|
| rs11570891 | C/T | Intron 9 | −11 | 0.073 |
| rs4922115 | G/A | Exon 10-3' UTR | 10 | 0.12 |
| rs3289 | T/C | Exon 10-3' UTR | 372 | 0.012 |
| rs11570892 | A/G | Exon 10-3' UTR | 797 | 0.14 |
| rs1803924 | C/T | Exon 10-3' UTR | 854 | 0.075 |
| rs1059507 | C/T | Exon 10-3' UTR | 1143 | 0.12 |
| rs3735964 | C/A | Exon 10-3' UTR | 1225 | 0.073 |
| rs3200218 | A/G | Exon 10-3' UTR | 1251 | 0.19 |
| rs13702 | T/C | Exon 10-3' UTR | 1672 | 0.24 |
| rs1059611 | T/C | Exon 10-3' UTR | 1743 | 0.081 |
| rs10645926 | —/TT | Exon 10-3' UTR | 1807 | 0.081 |
| rs15285 | C/T | Exon 10-3' UTR | 1847 | 0.24 |
| rs3866471 | C/A | Exon 10-3' UTR | 1849 | 0.13 |

Allele frequency data are from genotyping of 847 subjects. Position is given to show relative distance of SNPs from one another; this numbering corresponds to the position relative to the first nucleotide of exon 10. Numbers in parentheses correspond to the naming of SNPs in previous studies (5, 11, 20).
MAF, minor allele frequency.
$^{\alpha}$rs320 is the HindIII variant; rs328 is the Ser447 stop variant.

TABLE 5-3

Haplotypes defined by genotyping 19 polymorphisms in a large population sample

| Haplotypes based on 19 variants | Original six SNP haplotypes |
|---|---|
| Haplo 19-1  1111111111111111111 (0.54) | Haplotype 1 (0.628) |
| Haplo 19-2  1211111111111211111 (0.18) | Haplotype 2 (0.152) |
| Haplo 19-3  2122121212121121122 (0.11) | Haplotype 3 (0.101) |
| Haplo 19-4  1122212111212122221 (0.072) | Haplotype 4 (0.067) |
| Haplo 19-5  1111111111111121121 (0.023) | Haplotype 1 |
| Haplo 19-6  1122121212121121122 (0.017) | Haplotype 5 (0.024) |
| Haplo 19-7  1111111121111111111 (0.009) | Haplotype 1 |

Haplotype frequencies are shown in parentheses after each haplotype. The 19 variant-based haplotypes were derived from 847 genotyped subjects. The frequencies of the original six SNP haplotypes are those from the original cohort from which they were derived, 475 haplotyped subjects (5). The number 1 indicates the major allele at each SNP, 2 the minor allele.

TABLE 5-4

Subject characteristics and metabolic phenotypes by haplotype carrier status

| | Whole cohort | Noncarriers of 19-4 | Carriers of 19-4 |
|---|---|---|---|
| Age (yr) | 34.7 ± 8.7 | 35.0 ± 8.7 | 32.8 ± 8.4 |
| % Female | 58 | 60 | 53 |
| BMI (kg/m$^2$) | 28.9 ± 5.3 | 28.8 ± 5.2 | 29.8 ± 6.0$^{\alpha}$ |
| Waist circumference (cm) | 92.5 ± 12.6 | 92.2 ± 12.4 | 94.3 ± 13.5 |
| Waist-to-hip ratio | 0.89 ± 0.08 | 0.89 ± 0.08 | 0.89 ± 0.08 |
| Total cholesterol [mg/dl (mmol/liter)] | 184.8 ± 39.9 (4.78 ± 1.03) | 184.8 ± 39.9 (4.78 ± 1.03) | 185.0 ± 40.6 (4.78 ± 1.05) |
| Triglycerides [mg/dl (mmol/liter)] | 138.6 ± 105.8 (1.57 ± 1.19) | 141.0 ± 107.6 (1.59 ± 1.22) | 124.6 ± 93.6 (1.41 ± 1.06) |
| HDL-C [mg/dl (mmol/liter)] | 47.4 ± 13.5 (1.23 ± 0.35) | 47.2 ± 14.0 (1.22 ± 0.36) | 48.5 ± 10.2 (1.25 ± 0.26)$^{\alpha}$ |
| LDL-C [mg/dl (mmol/liter)] | 111.1 ± 33.5 (2.87 ± 0.87) | 110.9 ± 33.9 (2.87 ± 0.88) | 112.0 ± 31.3 (2.90 ± 0.81) |
| Apolipoprotein A-I [mg/dl (g/liter)] | 113.3 ± 19.5 (1.13 ± 0.19) | 112.4 ± 19.7 (1.12 ± 0.20) | 118.7 ± 16.9 (1.19 ± 0.17)$^{\alpha}$ |
| Apolipoprotein A-II [mg/dl (g/liter)] | 31.6 ± 6.8 (0.32 ± 0.07) | 31.2 ± 6.7 (0.31 ± 0.07) | 34.3 ± 6.4 (0.34 ± 0.06)$^{\alpha}$ |
| Apo A-I/A-II ratio | 3.69 ± 0.79 | 3.72 ± 0.81 | 3.55 ± 0.64 |
| Apolipoprotein B [mg/dl (g/liter)] | 88.2 ± 24.5 (0.88 ± 0.24) | 88.3 ± 24.2 (0.88 ± 0.24) | 87.5 ± 26.1 (0.88 ± 0.26) |
| FFA (mmol/liter) | 0.70 ± 0.26 | 0.72 ± 0.26 | 0.62 ± 0.23 |
| SBP (mm Hg) | 115.3 ± 14.9 | 114.5 ± 14.9 | 119.8 ± 14.2$^{\alpha}$ |
| DBP (mm Hg) | 67.8 ± 10.3 | 67.5 ± 10.2 | 69.6 ± 10.4 |
| Fasting glucose [mg/dl (mmol/liter)] | 94.5 ± 10.4 (5.24 ± 0.58) | 94.5 ± 10.6 (5.25 ± 0.59) | 94.1 ± 8.8 (5.22 ± 0.49) |
| 2-h glucose [mg/dl (mmol/liter)] | 121.1 ± 35.6 (6.72 ± 1.98) | 120.9 ± 36.3 (6.71 ± 2.02) | 122.3 ± 31.2 (6.79 ± 1.73) |
| Fasting insulin [μU/ml (pmol/liter)] | 14.1 ± 8.1 (101.4 ± 57.8) | 14.0 ± 8.1 (100.5 ± 58.1) | 14.9 ± 7.8 (107.2 ± 56.0) |
| M value (mg/kg · min) | 5.54 ± 2.78 | 5.57 ± 2.80 | 5.35 ± 2.68$^{\alpha}$ |

Values expressed with a plus/minus sign are means ± SD.
LDL, Low-density lipoprotein;
SBP, systolic blood pressure;
DBP, diastolic blood pressure.
$^{\alpha}$Significant ($P < 0.05$) haplotype-phenotype association by nonparametric genetic analysis.

Example 6

Haplotypes in the Lipoprotein Lipase Gene Influence High-Density Lipoprotein Cholesterol Response to Statin Therapy and Progression of Atherosclerosis in Coronary Artery Bypass Grafts Example 6 examined whether these LPL haplotypes influence response to lipid-lowering therapy among 829 subjects from the Post-Coronary Artery Bypass Graft trial. Lipid profiles were obtained at baseline and 4-5 years after treatment with lovastatin. Haplotypes were based on 12 SNPs. The fourth most frequent haplotype, 12-4, was associated with a decreased increment in high-density lipoprotein-cholesterol (HDL-C) following treatment. Haplotypes 12-6, 12-7 and 12-8 were each associated with increased HDL-C response to therapy, and haplotype 12-2 with decreased TG response. The most common haplotype, 12-1, was protective against graft worsening or occlusion. Haplotype 12-4 reduced HDL-C response to lovastatin, possibly consistent with our prior observations of this haplotype as predisposing to coronary artery disease. LPL may influence atherosclerosis risk through pleiotropic effects on each aspect of the metabolic syndrome.

The REGRESS study found that the D9N variant in LPL attenuated the total cholesterol (TC) and low-density lipoprotein cholesterol (LDL-C) response to pravastatin, but had no significant effect on angiographic progression of coronary artery lesions. In our initial studies in the Post-Coronary Artery Bypass Graft Trial (Post-CABG Trial) cohort, we observed no effect of D9N, whereas the HindIII variant in LPL was associated with increased coronary graft narrowing over time, independent of the degree of lipid lowering (moderate versus aggressive) with lovastatin. In this study, we expand on the latter result, examining the association of LPL haplotypes with the atherosclerosis and lipid response to lovastatin therapy. Our findings indicate that LPL haplotypes are associated with graft worsening and occlusion, and high-density lipoprotein-cholesterol (HDL-C) and TG response to statin (3-hydroxy-3-methylglutaryl-coenzyme A (HMG-CoA) reductase inhibitor) treatment. Notably, the haplotype associated with impaired HDL-C response to statin treatment in the Post-CABG cohort is the same haplotype associated with insulin resistance, atherosclerosis and increased LPL activity in a Mexican-American cohort at risk for coronary artery disease. Also, a different haplotype, associated with protection against atherosclerosis in the Mexican Americans, was associated with protection against graft narrowing or occlusion in the Post-CABG subjects.

Results

The clinical characteristics of 891 fully phenotyped subjects are shown in Table 6-1. In the Post-CABG trial, an overall 15% reduction in TC and a 26% reduction in LDL-C was observed. The aggressive treatment group had significantly greater reductions in these parameters than the moderate treatment group (TC: 23 versus 7%; LDL-C: 37 versus 14%, both P<0.0001). Response in HDL-C and TGs did not differ between the two treatment groups. A wide range of lipid responses was observed. Gender or race did not influence lipid response.

We genotyped 12 single nucleotide polymorphisms (SNPs) in the LPL gene. Table 6-2 shows the frequency and position information of the 12 LPL variants based on genotyping in all 903 subjects. We were able to successfully genotype and assign a common haplotype to 829 of the phenotyped and genotyped subjects. Linkage disequilibrium (D0) among the 12 SNPs (the HindIII variant plus 11 additional SNPs) ranged from 0.55 to 1 (average D0 of 0.92). The haplotypes constructed based on these 12 variants are listed in Table 6-3, along with their respective frequencies. These haplotypes are labeled 12-1, 12-2, 12-3, etc. to denote that they are based on a total of 12 polymorphisms, and to avoid confusion with the previously reported 19-SNP-based haplotypes. The eight most frequent haplotypes together comprise 96% of the haplotypes found in this population. The original 19-SNP-based haplotypes are also listed in Table 6-3, in rows corresponding to the new 12-SNP-based haplotypes. The latter shows that the common haplotypes are shared between the largely Caucasian Post-CABG population and the Mexican-American cohort, albeit with modest differences in frequency.

Haplotype 12-1, the most common haplotype, was associated with protection against progression of atherosclerosis (covariate-adjusted odds ratio (OR) 0.69, 95% confidence interval (CI) 0.49-0.97, P¼0.03); 41.4% of carriers of this haplotype experienced graft worsening compared with 48.9% of non-carriers. Furthermore, the mean proportion of grafts per subject showing progression of atherosclerosis was also significantly decreased for those carrying haplotype 12-1: 27% for haplotype 12-1 carriers compared with 32% for non-carriers of this haplotype (P¼0.048). Haplotype 12-1 carriers were also protected against the presence of graft occlusion (adjusted OR 0.57, 95% CI 0.36-0.91, P¼0.017); 10.7% of carriers of this haplotype experienced graft occlusion compared with 16.5% of non-carriers. None of the other haplotypes were significantly associated with progression or occlusion, although haplotype 12-4 showed a trend towards more frequent graft progression (OR 1.35, 95% CI 0.84-2.17, P¼0.22); 48.9% of carriers of this haplotype experienced graft worsening compared with 43.1% of non-carriers.

The fourth most frequent haplotype (12-4) was associated with a decreased increment in HDL-C (12-4 carriers: þ 6.8% HDL-C response versus non-carriers: þ 14.3% HDL-C response, P¼0.005) (Table 6-4). Conversely, three rare haplotypes, 12-6, 12-7 and 12-8, were each associated with increased HDL-C response to therapy compared to respective non-carriers (Table 6-4). Haplotype 12-2 was associated with a smaller increment in TGs (12-2 carriers: þ 2.6% versus non-carriers: þ 11.8% change in TGs, P¼0.02). The effects of LPL haplotypes on HDL-C and TG response were independent of whether subjects were in the intensive or moderate treatment group. LPL haplotypes were not associated with TC or LDL-C response to lipid-lowering therapy.

Secondary analyses detected association of haplotype 12-1 with decreased diastolic blood pressure (DBP) at baseline (79.278.9 in carriers versus 80.578.8 mm Hg in noncarriers, P¼0.045), haplotype 12-4 with increased DBP (81.478.8 in carriers versus 79.478.9 mm Hg in noncarriers, P¼0.026) and haplotype 12-3 with increased systolic blood pressure (SBP) (136.1716.7 in carriers versus 133.1717.5 mm Hg in non-carriers, P¼0.037). Haplotype 12-2 was associated with slightly decreased baseline HDL-C, 1.070.25 mmol/l (38.579.6 mg/dl) in carriers, versus 1.0370.25 mmol/l (39.879.8 mg/dl) in non-carriers (P¼0.035); haplotype 12-4 with increased HDL-C, 1.0870.27 mmol/l (41.7710.6 mg/dl) in carriers, versus 1.0170.25 (39.179.6 mg/dl) in non-carriers (P¼0.013); and haplotype 12-6 with increased HDL-C, 1.0970.29 mmol/(42.0711.4 mg/dl) in carriers, versus 1.0170.25 mmol/l (39.279.6 mg/dl) in non-carriers (P¼0.032). No LPL haplotype was associated with baseline levels of TC, LDL-C or TG.

Given the associations of haplotypes 12-1 and 12-4 with DBP, we re-analyzed the associations of these haplotypes with the primary phenotypes of atherosclerosis progression and lipid response by including DBP as a covariate in the analyses. The associations between haplotype 12-1 and atherosclerosis progression and graft occlusion were only slightly attenuated (P¼0.053 and P¼0.023, respectively). Inclusion of DBP as a covariate in the association analysis of haplotype 12-4 with HDL-C response did not alter the significance of that result (P¼0.009).

Discussion

In the Post-CABG cohort, we observed that haplotypes in the 30-end of LPL were associated with progression/occlusion of atherosclerosis in coronary grafts as well as lipid response in patients receiving lovastatin therapy. LPL hydrolyzes TGs present in very low-density lipoprotein (VLDL) and chylomicron particles, releasing free fatty acids and monoacylglycerol. LPL activity also indirectly raises HDL-C levels because LPL-mediated hydrolysis of VLDL-TG provides surface components that merge with HDL3 to form HDL2 particles. Therefore, it is not surprising that TG and HDL-C response, but not LDL-C response, to statin therapy appears to be influenced by genetic variation in LPL. Of note, we adjusted for lovastatin treatment group (moderate or aggressive lipid lowering) in our association analyses, and thus can conclude that the effect of LPL haplotypes on lipid response was independent of the statin dose. Effects of haplotypes 12-1 and 12-4 on atherosclerosis progression and HDL-C response, respectively, were also independent of haplotype effects on DBP.

Although genetic variation in LPL may influence lipid response to statin therapy simply by modulating lipid metabolism, another possible mechanism is that statins affect LPL expression and/or activity. In the latter model, genetic variation in LPL could alter the effect of statins on LPL expression. A number of investigators have hypothesized that the effect of statins on TG and HDL-C may be mediated via an effect on LPL. Rodent studies have produced conflicting results, showing either increased post-heparin LPL activity in rats treated with simvastatin, or no effects on LPL activity in rats treated with lovastatin or guinea-pigs treated with pitavastatin. An in vitro cellular study utilizing 3T3L1 adipocytes showed a dose- and time dependent increase in LPL mRNA levels in response to administration of atorvastatin. Administration of the potent statins simvastatin or atorvastatin to humans with hyperlipidemia and/or diabetes led to increases in preheparin LPL mass or post-heparin LPL activity in three out of four studies. The weaker statin fluvastatin did not alter LPL activity in dyslipidemic subjects. Given this evidence of statin modulation of LPL activity, the LPL haplotypes we analyzed may affect lipid response to statin by altering the responsiveness of LPL expression or activity to statins.

The LPL haplotype association results in this study are concordant with our prior studies of LPL haplotypes in Mexican Americans at risk for coronary artery disease, the Mexican-American Coronary Artery Disease (MACAD) study. In this study, haplotype 12-1 was associated with protection against graft worsening or occlusion. Haplotype 12-1 is equivalent to haplotype 19-1, which was associated with a lower prevalence of coronary artery disease in Mexican Americans. That this haplotype was not associated with lipids at baseline or in response to statin therapy suggests that the effect on atherosclerosis may be independent of LPL's effect in modulating lipid levels. Indeed, LPL may affect atherosclerosis risk by mechanisms independent of circulating cholesterol and TG levels. LPL has been shown to stimulate vascular smooth muscle cell proliferation in vitro. Yet another atherogenic effect of LPL is its ability to promote monocyte adhesion to bovine aortic endothelial cells. Perhaps these effects are less prominent in those individuals with haplotype 12-1.

On the other hand, our prior work suggested that haplotype 12-4 may be deleterious in terms of metabolic and cardiovascular risk. Possibly consistent with haplotype 12-4 as a risk haplotype, the current study demonstrated an association of haplotype 12-4 with a reduced HDL-C increase in response to statin therapy. In our MACAD study, this haplotype was associated with a trend to increased coronary artery disease prevalence as well as insulin resistance, elevated body mass index, elevated SBP, elevated HDL-C and elevated post-heparin LPL activity. The findings of increased baseline HDL-C and elevated DBP with haplotype 12-4 in this study are concordant with our prior findings of elevated HDL-C and SBP in Mexican Americans. Elevated HDL-C in carriers of this haplotype is consistent with increased LPL activity. The harmful effects in terms of insulin sensitivity, body mass index and blood pressure are likely related to local effects of LPL in mediating lipid uptake in muscle, adipose and the vascular wall, respectively. In terms of the attenuation of HDL-C increase in response to statin observed in this study, a plausible hypothesis is that carriers of haplotype 12-4 have relatively elevated LPL activity at baseline such that, when taking a statin, these subjects experience a lesser increase in LPL activity and thus experience a lower HDL-C increment. Perhaps the elevated baseline HDL-C explains why haplotype 12-4 was not significantly associated with graft worsening, despite the lower HDL-C increment on statin therapy. Alternatively, the low frequency of this haplotype may have reduced our ability to detect its association with graft progression. In any case, the clinical relevance to atherosclerosis of the haplotype 12-4 effect on HDL-C is uncertain, given that this haplotype was not significantly associated with graft worsening. Also, the modest effect of statins on HDL-C is not considered to be a major mechanism whereby these agents lower cardiovascular risk.

In the Post-CABG trial, on average TG levels increased by 7.5%, likely a reflection of the weak effect of lovastatin on TGs. Haplotype 12-2 carriers experienced a smaller increase in TG level. Whether this is a true pharmacogenetic effect could be tested in a trial utilizing a statin expected to lower TGs (e.g. atorvastatin) or a trial of an agent specifically targeting TGs (e.g. a fibrate).

Because the enzymatic action of LPL is most directly on TGs, it was unexpected that the most dramatic pharmacogenetic effects were on HDL-C response. The Post-CABG trial is atypical compared to other statin trials in the relatively large mean HDL-C response (Table 6-1). Perhaps this large response allowed us to detect the modulating effects of the LPL haplotypes. Although the pharmacogenetic effects of LPL on HDL-C and TG response are of unknown clinical significance, this study does provide mechanistic insight into the possible role of LPL in lipid response to statin therapy. This study supports the concept that common genetic variation in the LPL locus influences the HDL/TG axis in dynamic states (e.g. during treatment).

There have been very few studies examining the pharmacogenetic effects of LPL variation on the response to statin treatment. The REGRESS trial, a study of 819 subjects treated with pravastatin or placebo for 2 years, found that the D9N variant was associated with increased risk of coronary artery disease progression and clinical events in the placebo group. Atherosclerosis was not affected by the presence of this variant in the pravastatin group, suggesting that pravastatin overcame the harmful effects of the D9N variant. On the other hand, D9N carriers experienced an attenuated TC and LDL-C response to pravastatin treatment in the REGRESS trial. D9N was not considered in the current study because of our previous demonstration of its lack of effect on graft progression in the Post-CABG cohort14 and its location upstream of a recombination hotspot in intron 6 of LPL which separates it from the 30-end haplotypes we have been studying.

Our initial pharmacogenetic study in the Post-CABG cohort showed that the HindIII variant (and a closely linked tetranucleotide repeat) was associated with increased risk of graft progression; homozygotes for the minor allele of HindIII had increased risk. Haplotype 12-4 carries the minor (risk) allele of HindIII. Haplotype 12-1, herein associated with protection against graft progression, carries the major allele at HindIII. HindIII was not associated with HDL-C response to statin therapy. The present results explain why this was the case. The rare allele of HindIII is present on both haplotype 12-4 (associated with decreased HDL-C response) and haplotype 12-6 (associated with increased HDL-C response). When considering only the HindIII variant, subjects with these haplotypes are indistinguishable and the lipid responses averaged together, resulting in no effect of HindIII on HDL-C response to statin therapy.

Cladistic analysis of the LPL gene has shown that the haplotype structure of the 30-end of the gene is ancient and should be reflected in similar haplotypes across different population groups. Consistent with this prediction, our studies of the haplotype structure of the 30-end of LPL in Mexican Americans and now two independent Caucasian samples have found the same common haplotypes in each of the populations studied. As haplotype 12-4 (equivalent to the prior 19-4) appears to be associated with adverse atherosclerotic or metabolic risk in different populations, it is likely that an ancient variant arose on this common haplotype background that was then dispersed across different populations. Most likely this variant was beneficial in the era of scarce food and high physical activity, consistent with the thrifty genotype hypothesis, but is harmful in the modern era of excess food and low physical activity.

We note that HDL-C response to statin therapy was quite variable, as evidenced by the large standard deviation in HDL-C response. Similar high standard deviations were observed when examining the moderate and aggressive treatment groups separately. We hypothesize that genetic factors, such as variation in the LPL gene and likely additional genes, are responsible in part for this wide variability in HDL-C response. To our knowledge, no study has examined the heritability of lipid response to statin treatment. Such would require study in families. The alternative approach, successfully applied here, is to study specific candidate genes, such as the recent report of the influence of HMG-CoA reductase gene variation on LDL-C response to statin therapy.

Multiple testing is an issue that applies to all genetic studies in which multiple genetic variants are tested for association against multiple traits. In such studies, including ours, adjusting for multiple comparisons by such methods as Bonferroni corrections that assume all the tests are independent are often not utilized because they result in a significance level that is too stringent owing to the fact that the SNPs in the same gene are correlated, as are the phenotypes. In an effort to minimize multiple testing, we restricted our analyses to haplotype associations rather than associations of the 12 individual SNPs. Moreover, in this study, we were specifically interested in extending the haplotype association results of the LPL haplotypes (19-1 and 19-4) found associated with insulin resistance and atherosclerosis in our prior studies. That we found associations of the equivalent haplotypes 12-1 and 12-4 with graft progression and HDL-C response adds confidence to the association results reported herein.

In conclusion, this study demonstrates that haplotypes in the 3'end of LPL, previously shown to modulate atherosclerosis, insulin resistance, blood pressure, obesity and static lipid levels, also influence atherosclerosis progression and HDL-C and TG response to statin treatment. The most common haplotype appears to be protective, whereas the fourth most common haplotype appears to confer increased risk. By influencing each of the factors of the metabolic syndrome, the LPL gene and its product emerge as important factors in the development and progression of atherosclerosis.

Materials and Methods

Subjects

Figure 8:
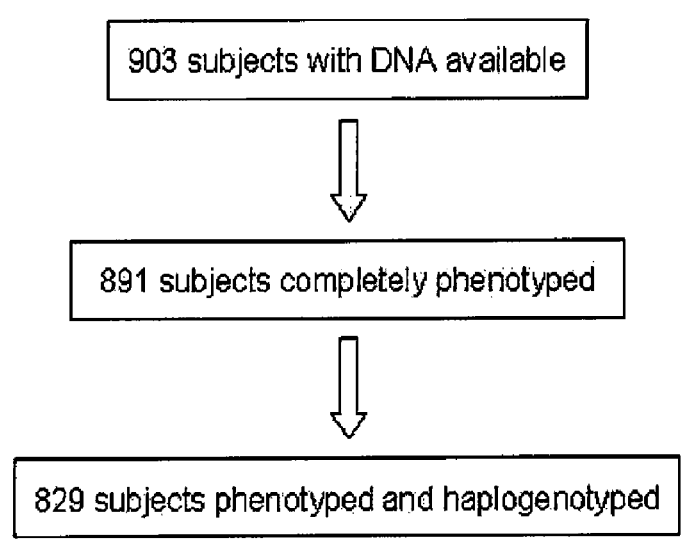
FIG. 8 is a flowchart of Post-CABG subjects studied.

This genetic association study is ancillary to the Post-Coronary Artery Bypass Graft Trial (Post-CABG Trial). A total of 1351 subjects from seven clinical centers throughout North America were included in the clinical trial and all were eligible as participants in this genetic ancillary study. Inclusion and exclusion criteria have been described previously. Subjects were randomly assigned for treatment to lower LDL-C levels with lovastatin, aggressively (target LDL 1.55-2.20 mmol/l (60-85 mg/dl)), cholestyramine added to lovastatin if necessary to reach target) or moderately (target LDL 3.36-3.62 mmol/l (130-140 mg/dl)). For the genetic study, DNA was isolated from 903 subjects following standard protocols. Follow-up complete angiographic data, lipid values and DNA were available from 891 of these individuals. See FIG. 8 for a flowchart of subjects. Subjects in this genetic study were collected in the latter years of the larger Post-CABG trial. Our previous comparison of the genetic study subjects with the subjects not included in the genetic study found fewer cardiovascular events, greater aspirin use and more favorable lipid levels in the former, suggesting that subjects with lesser risk for atherosclerosis progression were disproportionately included in the genetic study.

Genotyping and Haplotype Determination

In this study, 12 SNPs were genotyped for haplotype reconstruction. In this Post-CABG cohort, we previously genotyped the HindIII polymorphism located in intron 8 (rs320, also known as 83938) using conventional agarose gel techniques as described previously. Subsequently, we designed PCR primers and TaqMan™ MGB (Applied Biosystems, Foster City, Calif., USA) probes to genotype 11 additional LPL SNPs. These were selected based on our prior work demonstrating that haplotypes spanning exon 9 to exon 10 were associated with variation in postheparin plasma LPL activity and multiple phenotypes related to the metabolic syndrome in the Mexican-American Coronary Artery Disease (MACAD) cohort. In our study of LPL in the MACAD cohort, we genotyped 19 SNPs; herein, we genotyped HindIII plus a subset of 11 essential SNPs. These 11 SNPs (rs328 (Ser447Stop, also known as 9040), rs11570891, rs3289, rs1803924, rs1059507, rs3735964, rs3200218, rs1059611, rs10645926, rs15285, rs3866471) either tag the common haplotypes in this region or are unique to a particular haplotype (termed 19-4) that was associated with increased LPL activity. These 11 LPL SNPs were genotyped in 903 subjects using the 50-exonuclease assay (TaqMan™ MGB) described previously. PCR primers and TaqMan™ MGB probes for these 11 SNPs were reported previously.

Haploview 3 was used to determine the haplotypes present in the study population. Haploview constructs haplotypes by using an accelerated expectation maximization algorithm similar to the partition/ligation method, which creates highly accurate population frequency estimates of the phased haplotypes based on the maximum likelihood derived from the unphased input genotypes. Haploview also identified six SNPs (rs328, rs3289, rs3735964, rs3200218, rs15285, rs3866471) that tag the haplotypes with frequency 40.01.

Of the 891 subjects genotyped at all 12 LPL variants, 829 with complete follow-up phenotypic data were assigned a haplogenotype using an in-house algorithm. This algorithm examined the genotype at all six haplotype tagging SNPs for each predicted possible combination of two haplotypes (i.e. haplogenotype); the genotypes at each tag SNP (1¼ homozygous for major allele; B¼ heterozygous; 2¼ homozygous for minor allele) were considered together as a genotype pattern that is specific to a particular haplogenotype. In these data, each possible pair of haplotypes was reflected in a unique genotype pattern, with the exception of haplogenotype 12-1/12-4 and haplogenotype 12-6/12-8, both of which had the same genotype pattern (B1B1B1). The frequencies of these haplotypes (12-1: 0.431; 12-4: 0.057; 12-6: 0.035; 12-8: 0.022; Table 6-3) allowed a determination of the relative frequency of haplogenotype 12-1/12-4 versus 12-6/12-8 ((0.431_0.057)/(0.035'0.022) ¼32). Thus, haplogenotype 12-1/12-4 should be 32 times more common in the data than 12-6/12-8. In our population, 45 subjects had the ambiguous genotype pattern; assigning all of them a haplogenotype of 12-1/12-4 may have resulted in an error in B1 subject. This gives an overall error rate of ⅟₈₂₉ (0.12%).

Phenotyping

All demographic, family history, medical history and clinical data were collected as part of the Post-CABG Trial. The progression of atherosclerosis was quantitatively determined by comparison of an initial angiogram at enrollment with a follow-up angiogram repeated an average of 4.3 years later. Baseline and follow-up angiography were obtained with catheterization techniques that permitted computer assisted quantitative measurement. An initially patent graft was defined as having progression of atherosclerosis if there was a decrease of 0.6 mm or more in lumen diameter at the site of greatest change at follow-up. Subjects with 'progression of atherosclerosis' were defined as those subjects with one or more grafts showing progression. Graft occlusion was also assessed. Baseline and post-treatment lipid levels (TC, LDL-C, HDL-C and TGs) were obtained.

All procedures were approved by the institutional review boards of Cedars-Sinai Medical Center and the other centers participating in the Post-CABG Trial. Informed consent for the clinical trial was obtained before enrollment and consent for this genetic study was obtained during follow up.

Association Analysis

The primary phenotypes analyzed for association with LPL haplotypes were (a) the progression of atherosclerosis and (b) lipid response to lovastatin therapy. Secondary analyses included association of the LPL haplotypes with baseline lipid and SBP and DBP measurements.

Association of LPL haplotypes with presence/absence of atherosclerosis progression and with presence/absence of graft occlusion was evaluated using logistic regression. Association with TC, LDL-C, HDL-C and TG response to lovastatin therapy, baseline lipid and baseline blood pressure measurements was evaluated using analysis of covariance (ANCOVA). All analyses were adjusted for age, gender, current smoking status, time between CABG and enrollment, race and lovastatin group (moderate or aggressive) by inclusion of these parameters as independent variables in the logistic regression or ANCOVA analyses. Quantitative trait values were log-transformed as appropriate to reduce non-normality. For each haplotype analysis, haplogenotype was coded as an independent variable as 'carrier' or 'noncarrier.' Single SNP association analyses were not carried out, both to reduce the number of statistical tests and because our interest is in association of LPL haplotypes with atherosclerotic and metabolic phenotypes.

Tables

TABLE 6-1

Clinical characteristics of the 891 post-CABG subjects

| Phenotype | Mean ± s.d. (range) |
|---|---|
| Age (years) | 61.7 ± 7.5 (35.2-76.1) |
| Male gender (%) | 91.9 |
| Caucasian (%) | 93.7 |
| Current smoking (%) | 9.3 |
| Time between CABG and enrollment (years) | 4.7 ± 2.5 (0.3-11.3) |
| Baseline SBP (mm Hg) | 134.0 ± 17.4 (82.0-200.0) |
| Baseline DBP (mm Hg) | 79.6 ± 8.8 (55.0-108.0) |
| Baseline LDL-C (mmol/l) | 4.02 ± 0.52 (2.46-6.05) |
| Baseline HDL-C (mmol/l) | 1.02 ± 0.25 (0.49-2.56) |
| Baseline total cholesterol (mmol/l) | 5.87 ± 0.66 (3.75-8.15) |
| Baseline TGs (mmol/l) | 1.82 ± 0.79 (0.51-5.46) |
| LDL-C response (%) | −25.7 ± 20.6 (−78.8-45.9) |
| HDL-C response (%) | 13.8 ± 24.4 (−61.9-153.1) |
| Total cholesterol response (%) | −15.3 ± 16.3 (−58.4-43.5) |
| TG response (%) | 7.3 ± 53.0 (−83.6-330.2) |

Abbreviations: CABG, coronary artery bypass graft; DBP, diastolic blood pressure; HDL-C, high density lipoprotein-cholesterol; LDL-C, low-density lipoprotein-cholesterol; SBP, systolic blood pressure; TG, triglyceride.

TABLE 6-2

Frequency and position information on 12 LPL variants

| Variant designation | Variation | Location | Position | MAF |
|---|---|---|---|---|
| rs320 (8393)[a] | T/G | Intron 8 | −3744 | 0.28 |
| rs328 (9040)[a] | C/C | Exon 9 | −3097 | 0.095 |
| rs11570891 | C/T | Intron 9 | −11 | 0.10 |
| rs3289 | T/C | Exon 10/3'-UTR | 372 | 0.037 |
| rs18032924 | C/T | Exon 10/3'-UTR | 854 | 0.099 |
| rs1059507 | C/T | Exon 10/3'-UTR | 1143 | 0.18 |
| rs3735964 | C/A | Exon 10/3'-UTR | 1225 | 0.096 |
| rs3200218 | A/C | Exon 10/3'-UTR | 1251 | 0.20 |
| rs1059611 | T/C | Exon 10/3'-UTR | 1743 | 0.11 |
| rs10645926 | —/TT | Exon 10/3'-UTR | 1807 | 0.11 |

TABLE 6-2-continued

Frequency and position information on 12 LPL variants

| Variant designation | Variation | Location | Position | MAF |
|---|---|---|---|---|
| rs15285 | C/T | Exon 10/3'-UTR | 1847 | 0.31 |
| rs3866471 | C/A | Exon 10/3'-UTR | 1849 | 0.37 |

Abbreviations: MAF, minor allele frequency; LPL, lipoprotein lipase; SNP, single nucleotide polymorphism.
Allele frequency data are genotyping of 903 subjects. Position is given to show the relative distance of SNPs from one another; the numbering corresponds to the position relative to the first nucleotide of exon 10. Numbers in parentheses correspond to the naming of SNPs in prior studies.[8,11,35]
[a]rs320 is the HindIII variant; rs328 is the Ser447stop variant.

TABLE 6-3

LPL haplotypes defined by genotyping 12 polymorphisms

| Haplotypes based on 12 variants in the Post-CABG cohort | | | Corresponding haplotypes from the MACAD study[a] | |
|---|---|---|---|---|
| Designation | Haplotype | Frequency | Designation | Frequency |
| 12-1 | 111111111111 | 0.431 | 19-1 | 0.536 |
| 12-2 | 111111121111 | 0.187 | 19-2 | 0.177 |
| 12-3 | 211112111122 | 0.168 | 19-3 | 0.107 |
| 12-4 | 222121212221 | 0.057 | 19-4 | 0.072 |
| 12-5 | 111211111111 | 0.037 | 19-6 | 0.017 |
| 12-6 | 222121112221 | 0.035 | | |
| 12-7 | 111111111121 | 0.027 | 19-5 | 0.023 |
| 12-8 | 111111211111 | 0.022 | | |

Abbreviations: CABG, coronary artery bypass graft; LPL, lipoprotein lipase.
The 12-variant-based haplotypes were derived from 903 genotyped subjects. 1 indicates the major allele at each SNP, 2 the minor allele.
[a]The Mexican-American Coronary Artery Disease (MACAD) study, a study of adult offspring of Mexican-American probands with coronary artery disease.[8,11,12]

TABLE 6-4

Percent change in HDL-C according to LPL haplotype carrier status

| Haplotype | Carriers[a] | Non-carriers[a] | P-value for association[b] |
|---|---|---|---|
| 12-1 | 12.6 ± 24.3 (568) | 15.2 ± 24.2 (261) | 0.16 |
| 12-2 | 12.4 ± 24.5 (295) | 14.0 ± 24.2 (534) | 0.44 |
| 12-3 | 14.2 ± 23.5 (262) | 13.1 ± 24.2 (567) | 0.51 |
| 12-4 | 6.8 ± 20.0 (93) | 14.3 ± 24.7 (736) | 0.0053 |
| 12-5 | 11.4 ± 25.6 (61) | 13.6 ± 24.2 (768) | 0.89 |
| 12-6 | 24.8 ± 19.8 (52) | 12.7 ± 24.4 (777) | 0.0024 |
| 12-7 | 21.9 ± 24.1 (44) | 13.0 ± 24.3 (785) | 0.012 |
| 12-8 | 23.0 ± 26.0 (43) | 12.8 ± 24.4 (786) | 0.0015 |

Abbreviations: CABG, coronary artery bypass graft; HDL-C, high-density lipoprotein-cholesterol; LPL, lipoprotein lipase.
[a]Data are mean ± s.d. (number of subjects).
[b]P-value for association adjusted for age, gender, current smoking status, time between CABG and enrollment, race and lovastatin group (moderate or aggressive).

Example 7

Haplotypes in the Lipoprotein Lipase Gene Influence Fasting Insulin and the Discovery of a New Risk Haplotype: The IRAS Family Study Prior studies of Mexican Americans described association of lipoprotein lipase (LPL) gene haplotypes with insulin sensitivity/resistance and atherosclerosis. The most common haplotype (haplotype 1) was protective while the fourth most common haplotype (haplotype 4) conferred risk for insulin resistance and atherosclerosis. In this study of Hispanics in the IRAS Family Study, we sought to replicate LPL haplotype association with insulin sensitivity/resistance. LPL haplotypes based on 12 single nucleotide polymorphisms were analyzed for association with indexes of insulin sensitivity and other metabolic and adiposity measures. 978 members of 86 Hispanic families participated and LPL haplogenotype, metabolic phenotypes, and adiposity was measured. The haplotype structure was identical to that observed in prior studies. Among 978 phenotyped subjects, haplotype 1 was associated with decreased fasting insulin (P=0.01); haplotype 4 was associated with increased fasting insulin (P=0.02) and increased visceral fat mass (P=0.002). Insulin sensitivity, derived from intravenous glucose tolerance testing, tended (P>0.1) to be higher with haplotype 1 ($S_I$=1.72) and lower with haplotype 4 ($S_I$=1.38). Haplotype 2 was associated with increases in fasting insulin, triglycerides, triglyceride/HDL-C ratio, and apolipoprotein B (P=0.01-0.04).

In conclusion, this study independently replicates our prior results of LPL haplotypes 1 and 4 as associated with measures of insulin sensitivity and resistance, respectively. Haplotype 4 may confer insulin resistance by increasing visceral fat. Haplotype 2 was identified as a new risk haplotype, suggesting a complex nature of LPL's effect on features of the insulin resistance syndrome.

In the current experiment, we turned to Hispanics in the Insulin Resistance Atherosclerosis Study (IRAS) Family Study. Our goal was to replicate our principal result, that LPL 3' end haplotypes are associated with insulin sensitivity/resistance. We also evaluated haplotype association with other phenotypes. We found that the same two LPL haplotypes (haplotypes 1 and 4) associated with insulin sensitivity/resistance in MACAD were also associated with indexes of insulin sensitivity/resistance in the IRAS Hispanics. Furthermore, the insulin resistance haplotype 4 was associated with visceral adiposity. We also discovered in IRAS that haplotype 2 was associated with increased fasting insulin and adverse effects on lipid parameters, representing a new risk haplotype.

Subjects and Methods

Subjects. Participants are members of Hispanic families recruited for the IRAS Family Study from 2 clinical sites, San Antonio, Tex.; and the San Luis Valley, Colo. For the study design and recruitment strategies see Henkin et al. All subjects gave informed consent.

Genotyping and Haplotype Determination

Twelve single SNPs were genotyped in LPL, including the original six 3' end SNPs, rs312, rs319, rs320, rs327, rs328, rs330 (previously designated 7315, 8292, 8393, 8852, 9040, 9712). We also genotyped the following exon 10 variants identified from prior sequencing: rs4922115, rs3289, rs3200218, rs1059611, rs15285, rs3866471. These six variants were predicted to tag the common haplotypes in exon 10.

The 12 SNPs were genotyped in 1424 subjects from 90 families using the 5'-exonuclease assay (TaqMan™ MGB) and primers and probes described previously.

The program Haploview was used to determine haplotype frequencies as well as delineate haplotype blocks. Haploview constructs haplotypes using an accelerated expectation maximization algorithm. Haploview was used to calculate linkage disequilibrium (LD, D' and $r^2$) between each pairwise combination of SNPs.

Haplotypes were constructed as the most likely set (determined by maximum likelihood) of fully determined parental haplotypes of the marker loci for each individual, using the simulated annealing algorithm implemented in Simwalk2. This allowed us to assign a haplogenotype to 1262 of the 1424 genotyped subjects.

Phenotyping

Indexes of glucose homeostasis were assessed by the frequently sampled intravenous glucose tolerance test (IVGTT), with minimal model (MINMOD) analyses. The IVGTT protocol was modified as previously described. Insulin sensitivity index ($S_I$) and glucose effectiveness ($S_G$) were calculated using MINMOD. The acute insulin response to glucose ($AIR_G$) was the mean insulin increment in the plasma insulin concentration above the basal in the first 8 min after the administration of glucose. Disposition index was calculated as $DI=AIR \times S_I$. Plasma glucose was obtained using standard methods, and insulin was measured by a single-antibody radioimmunoassay. Glucose and insulin values were used to derive the HOMA index of insulin resistance. Of the genotyped subjects, 978 subjects from 86 families were haplotyped and had measures of insulin sensitivity.

Lipid parameters, blood pressure, and anthropometry were measured as previously described. Computed tomographic evaluation of visceral and subcutaneous fat at the L4-L5 level was performed.

Data Analysis

Association was evaluated by quantitative transmission disequilibrium testing using the QTDT program. Age, gender, and body mass index (BMI) were specified as covariates. The within family component of association was evaluated, to eliminate any effects of population stratification. Log-transformed or square-root transformed trait values were used as appropriate to reduce skewness. For illustrative purposes, trait values by haplotype are presented as the median values in carriers of a particular haplotype versus non-carriers.

The primary phenotypes for association were indexes of insulin sensitivity (fasting insulin, HOMA, and $S_I$), given our main goal of replicating association of LPL haplotypes with insulin sensitivity/resistance. Overall P values and haplotype-specific P values were calculated for the primary traits. Secondary phenotypes included $AIR_G$, DI, $S_G$, lipid traits, measures of adiposity (BMI, waist-to-hip ratio, subcutaneous and visceral adipose tissue) and blood pressure. Only haplotypes showing association with primary traits were analyzed for association with secondary traits.

Results

SNP frequencies and LD are shown in Supplementary Tables 7-1 and 7-2. All markers were in Hardy-Weinberg equilibrium. One haplotype block was identified, spanning all 12 SNPs from intron 7 through exon 10. The common haplotypes are displayed in Table 7-1. The haplotypes observed in this Hispanic population were also observed in our prior studies of Hispanics in the MACAD study, with modest differences in frequency (Table 7-1).

No LPL haplotype was significantly associated with $S_I$ from the IVGTT (overall P value for haplotypic association >0.1). However, LPL haplotypes were significantly associated with fasting insulin and HOMA (overall P values for haplotypic association 0.0011 and 0.0008, respectively). Significant individual haplotype associations were observed. Haplotype 1 was associated with increased insulin sensitivity, as seen by the lower fasting insulin (P=0.010) in haplotype 1 carriers versus non-carriers (Table 7-2). Haplotype 2 (P=0.0096) and haplotype 4 (P=0.022) were associated with insulin resistance, i.e. higher fasting insulin. Association results for HOMA values tracked exactly as the fasting insulin results. $S_I$ was not statistically significantly associated with these haplotypes; however, median values agreed, with haplotype 1 associated with insulin sensitivity (higher $S_I$) and haplotypes 2 and 4 with insulin resistance (lower $S_I$) (Table 7-2).

Secondary analyses investigating association of haplotypes 1, 2, and 4 with lipid, adiposity, and blood pressure traits were next carried out. We found no further associations with haplotype 1. Haplotype 4 was associated only with increased visceral fat mass (P=0.0019). Haplotype 2 was associated with increases in triglycerides (P=0.021), triglyceride/HDL ratio (P=0.041), and apolipoprotein B (P=0.023).

Discussion

In this study of Hispanic families of the IRAS Family Study, we demonstrated association of LPL haplotype 1 with decreased fasting insulin and haplotype 4 with increased fasting insulin and with increased visceral fat mass. We also identified haplotype 2 as predisposing to both insulin resistance and dyslipidemic features.

Our prior work demonstrated association of haplotype 1 with insulin sensitivity and haplotype 4 with insulin resistance in the MACAD study. In this study of Hispanic families we demonstrated association of haplotype 1 with decreased fasting insulin and haplotype 4 with increased fasting insulin. This represents confirmation of our initial findings in a separate population of similar ethnicity. In the genetic epidemiology of common disorders, independent replication of linkage or association results, achieved in only a fraction of all studies, provides convincing support for the effect of a gene on a phenotype. Variation in the 3' end of LPL appears to influence insulin sensitivity/resistance in Hispanics; whether it does so in other populations remains to be shown.

Overactivity of LPL may lead to excessive adipose accumulation. Excess adiposity, particularly in the visceral depot, may contribute to insulin resistance via altered secretion of adipocytokines such as adiponectin and leptin. Our prior work identified haplotype 4 as predisposing to insulin resistance and increased LPL activity. The present study suggests a possible mechanism unifying these findings, that the increased LPL activity with haplotype 4 is mainly expressed in visceral adipose tissue, leading to increased visceral fat mass and consequently insulin resistance.

Herein, Haplotype 2 was associated with adverse effects on fasting insulin and lipid parameters, multiple facets of the metabolic syndrome. That Hispanic Americans have the highest age-specific prevalence of the metabolic syndrome may in part be explained by their high frequency (~18%) of haplotype 2. Haplotype 2 was not associated with insulin resistance in MACAD, perhaps because of the smaller sample size of MACAD. This is the first detection of phenotypic effects of haplotype 2. Given the non-disease specific ascertainment of IRAS families, haplotype 2 is likely to be important to Hispanics in general and warrants further investigation. Because haplotype 2 has very few sequence differences from haplotype 1, and no minor alleles in common with haplotype 4, the functional variants on haplotype 2 may lie in coding or regulatory regions outside the 3' UTR (exon 10) that we previously sequenced. This may explain the different phenotypic associations displayed by haplotypes 2 and 4. That haplotype 2 influenced lipid traits is not surprising, given LPL's role in the metabolism of triglycerides in chylomicrons and VLDL particles. After interacting with LPL, these particles form remnants that then contribute to formation of HDL particles and apolipoprotein B-containing particles.

This work provides independent confirmation in two independent Hispanic populations of LPL as influencing insulin sensitivity/resistance, with the exact same haplotypes (haplotypes 1 and 4) displaying the previously identified opposing effects. We also have preliminary evidence for a mechanism connecting haplotype 4 to insulin resistance, that of increased visceral adiposity. In addition, a new risk haplotype (haplotype 2) in LPL was identified, which will lead to additional investigation and likely further elucidation of the complex role played by LPL in the insulin resistance syndrome and its multiple phenotypes.

Tables

TABLE 7-1

LPL Haplotypes Defined
by Genotyping 12 Polymorphisms

| Designation | Haplotype based on 12 variants in the Hispanic American IRAS cohort | Corresponding haplotype from the MACAD study* |
|---|---|---|
| 1 | 111111111111 (0.488) | 19-1 (0.536) |
| 2 | 121111112111 (0.176) | 19-2 (0.177) |
| 3 | 212212211122 (0.122) | 19-3 (0.107) |
| 4 | 112221111221 (0.096) | 19-4 (0.072) |
| 5 | 112212211122 (0.027) | 19-5 (0.017) |
| 6 | 111111111121 (0.025) | 19-6 (0.023) |
| 7 | 111111121111 (0.025) | 19-7 (0.009) |

Haplotype founder frequencies are shown in parentheses after each haplotype. The 12-variant based haplotypes were derived from 1262 haplogenotyped subjects. 1 indicates the major allele at each SNP, 2 the minor allele.
*The Mexican-American Coronary Artery Disease (MACAD) study, a study of adult offspring of Mexican-American probands with coronary artery disease (3, 4, 6).

TABLE 7-2

Median phenotype levels by haplotype carrier status

| Trait | Haplotype 1 | | Haplotype 2 | | Haplotype 3 | | Haplotype 4 | |
|---|---|---|---|---|---|---|---|---|
| | Carrier (n = 732) | Non-carrier (n = 241) | Carrier (n = 738) | Non-carrier (n = 600) | Carrier (n = 224) | Non-carrier (n = 754) | Carrier (n = 132) | Non-carrier (n = 846) |
| Primary phenotypes | | | | | | | | |
| Fasting glucose (mg/dL) | 91.5 (11.5) | 92.5 (11.0) | 92.5 (12.3) | 91.5 (11.5) | 91.0 (10.5) | 92.0 (12.0) | 93.5 (12.5)§ | 91.5 (11.0) |
| Fasting insulin μIU/ml | 12.0 (11.0)† | 13.0 (13.0) | 13.0 (11.0)† | 12.0 (11.0) | 13.0 (13.0) | 12.0 (11.0) | 13.0 (14.0)‡ | 12.0 (11.0) |
| HOMA | 49.3 (47.6)† | 54.3 (55.7) | 54.8 (51.9)† | 47.9 (48.2) | 53.4 (57.3) | 49.7 (47.3) | 53.7 (65.7)† | 49.5 (48.3) |
| $S_I$ | 1.72 (2.09) | 1.61 (1.92) | 1.50 (1.83) | 1.82 (2.15) | 1.78 (2.18) | 1.67 (2.03) | 1.38 (1.96) | 1.72 (2.07) |
| Secondary phenotypes | | | | | | | | |
| BMI (kg/m$^2$) | 27.7 (8.1) | 28.9 (8.4) | 28.4 (7.9) | 27.9 (8.0) | 28.6 (9.6) | 28.0 (7.6) | 28.8 (8.3) | 27.9 (7.9) |

TABLE 7-2-continued

Median phenotype levels by haplotype carrier status

| Trait | Haplotype 1 Carrier (n = 732) | Haplotype 1 Non-carrier (n = 241) | Haplotype 2 Carrier (n = 738) | Haplotype 2 Non-carrier (n = 600) | Haplotype 3 Carrier (n = 224) | Haplotype 3 Non-carrier (n = 754) | Haplotype 4 Carrier (n = 132) | Haplotype 4 Non-carrier (n = 846) |
|---|---|---|---|---|---|---|---|---|
| VAT (cm$^2$) | 101.8 (82.9) | 106.6 (76.3) | 104.3 (81.1) | 105.5 (80.4) | 110.5 (77.9) | 101.4 (81.7) | 106.9 (76.0)* | 102.9 (81.1) |
| TG (mg/dL) | 99.0 (85.0) | 106.0 (86.0) | 104.9 (91.0)‡ | 99.0 (86.0) | 101.0 (84.0) | 101.0 (87.0) | 89.5 (80.0) | 102.5 (87.0) |
| TG/HDL | 2.32 (2.69) | 2.42 (3.03) | 2.48 (2.92)2 | 2.22 (2.68) | 2.21 (2.36) | 2.40 (2.83) | 2.02 (2.55) | 2.39 (2.81) |
| Apo B (mg/dL) | 87.0 (28.0) | 87.0 (30.0) | 88.0 (29.0)‡ | 85.0 (29.0) | 87.5 (33.0) | 87.0 (28.0) | 86.5 (28.0) | 87.0 (29.0) |

Data are median (interquartile range). See Supplementary Table 3 for detailed trait values by haplogenotype.
$S_I$ = insulin sensitivity index;
VAT = visceral adipose tissue; TG = triglycerides;
HDL = HDL cholesterol;
Apo B = apolipoprotein B. To convert glucose from mg/dL to mmol/L,
multiply by 0.05551; to convert insulin from µIU/mL to pmol/L, multiply by 7.175; to convert triglycerides from mg/dL to mmol/L, multiply by 0.01129.
*Significant association of phenotype with haplotype,
P = 0.002;
†P = 0.01;
‡P = 0.02;
§P = 0.03;
2P = 0.04

SUPPLEMENTARY TABLE 7-1

Frequency and Position Information on 12 LPL Variants

| Variant Designation | Variation | Location | Position | MAF |
|---|---|---|---|---|
| rs312 (7315) | G/C | Intron 7 | −4822 | 0.14 |
| rs319 (8292) | A/C | Intron 8 | −3845 | 0.19 |
| rs320 (8393)* | T/G | Intron 8 | −3744 | 0.29 |
| rs327 (8852) | T/G | Intron 8 | −3285 | 0.30 |
| rs328 (9040)† | C/G | Exon 9 | −3097 | 0.088 |
| rs330 (9712) | G/A | Intron 9 | −2425 | 0.19 |
| rs4922115 | G/A | Exon 10-3' UTR | 10 | 0.17 |
| rs3289 | T/C | Exon 10-3' UTR | 372 | 0.025 |
| rs3200218 | A/G | Exon 10-3' UTR | 1251 | 0.18 |
| rs1059611 | T/C | Exon 10-3' UTR | 1743 | 0.11 |
| rs15285 | C/T | Exon 10-3' UTR | 1847 | 0.30 |
| rs3866471 | C/A | Exon 10-3' UTR | 1849 | 0.17 |

MAF = minor allele frequency. Allele frequency data is from genotyping of 1424 subjects.
Position is given to show relative distance of SNPs from one another; the numbering corresponds to the position relative to the first nucleotide of exon 10. Numbers in parentheses correspond to the naming of SNPs in prior studies (3, 4, 8).
*rs320 is the HindIII variant;
†rs328 is the Ser447stop variant.

SUPPLEMENTARY TABLE 7-2

Linkage disequilibrium among the 12 SNPs

| Marker 1 | Marker 2 | D$^1$ | r$^2$ |
|---|---|---|---|
| rs312 | rs139 | 1 | 0.031 |
| rs312 | rw220 | 1 | 0.377 |
| rs312 | rs327 | 1 | 0.365 |
| rs312 | rs328 | 1 | 0.015 |
| rs312 | rs350 | 1 | 0.699 |
| rs312 | rs4922115 | 0.979 | 0.778 |
| rs312 | rs3289 | 1 | 0.004 |
| rs312 | rs3200218 | 1 | 0.031 |
| rs312 | rs1059611 | 1 | 0.118 |
| rs312 | rs15285 | 1 | 0.338 |
| rs312 | rs3866471 | 1 | 0.759 |
| rs319 | rs320 | 1 | 0.084 |
| rs319 | rs327 | 1 | 0.083 |
| rs319 | rs328 | 1 | 0.029 |
| rs319 | rs330 | 1 | 0.045 |
| rs319 | rs4922115 | 1 | 0.038 |
| rs319 | rs3289 | 1 | 0.006 |
| rs319 | rs9200218 | 1 | 0.08 |
| rs319 | rs1059611 | 1 | 0.028 |
| rs319 | rs15385 | 1 | 0.093 |
| rs319 | rs3866471 | 1 | 0.041 |
| rs320 | rs327 | 0.989 | 0.956 |
| rs320 | rs328 | 1 | 0.273 |
| rs320 | rs330 | 1 | 0.54 |
| rs320 | rs4922115 | 1 | 0.465 |
| rs320 | rs3289 | 1 | 0.01 |
| rs320 | rs3200218 | 1 | 0.082 |
| rs320 | rs059611 | 1 | 0.328 |
| rs320 | rs15285 | 0.94 | 0.792 |
| rs320 | rs3856471 | 0.937 | 0.437 |
| rs327 | rs328 | 1 | 0.272 |
| rs327 | rs330 | 1 | 0.527 |
| rs327 | rs4922115 | 1 | 0.45 |
| rs327 | rs3289 | 1 | 0.01 |
| rs327 | rs3200128 | 1 | 0.084 |
| rs327 | rs1059611 | 1 | 0.325 |
| rs327 | rs15285 | 0.954 | 0.834 |
| rs327 | rs3866471 | 1 | 0.482 |
| rs328 | rs330 | 1 | 0.021 |
| rs328 | rs4922115 | 1 | 0.018 |
| rs328 | rs3289 | 1 | 0.003 |
| rs328 | rs3200218 | 1 | 0.023 |
| rs328 | rs1059611 | 1 | 0.823 |
| rs328 | rs15285 | 1 | 0.251 |
| rs328 | rs3866471 | 1 | 0.02 |
| rs330 | rs4922115 | 1 | 0.861 |
| rs330 | rs3289 | 1 | 0.005 |
| rs330 | rs3200218 | 1 | 0.044 |
| rs330 | rs1059611 | 0.147 | 0.001 |
| rs330 | rs15285 | 1 | 0.476 |
| rs330 | rs3866471 | 0.949 | 0.83 |
| rs4922115 | rs3289 | 1 | 0.005 |
| rs4922115 | rs3200218 | 1 | 0.039 |
| rs4922115 | rs1059611 | 1 | 0.02 |
| rs4922115 | rs15285 | 1 | 0.434 |
| rs4922115 | rs3866471 | 1 | 0.941 |
| rs3289 | rs3200218 | 1 | 0.006 |

SUPPLEMENTARY TABLE 7-2-continued

Linkage disequilibrium among the 12 SNPs

| Marker 1 | Marker 2 | D¹ | r² |
|---|---|---|---|
| rs3289 | rs1059611 | 1 | 0.003 |
| rs3289 | rs15285 | 1 | 0.011 |
| rs3289 | rs3866471 | 1 | 0.005 |
| rs3200218 | rs1059611 | 1 | 0.026 |
| rs3200218 | rs15285 | 1 | 0.087 |
| rs3200218 | rs3866471 | 1 | 0.041 |
| rs1059611 | rs15285 | 1 | 0.293 |
| rs1059611 | rs3866471 | 1 | 0.021 |
| rs15285 | rs3866471 | 1 | 0.462 |

SUPPLEMENTARY TABLE 7-3

Median trait values by LPL haplogenotype

| | | Fasting Insulin | | HOMA | |
|---|---|---|---|---|---|
| | N | Median | IQR | Median | IQR |
| Homozygous for haplotype 1 | 230 | 12 | 9 | 47.82 | 39.43 |
| Heterozygous for haplotype 1 | 507 | 12 | 11 | 49.73 | 50.55 |
| No haplotype 1 | 241 | 13 | 13 | 54.27 | 55.27 |
| Homozygous for haplotype 2 | 51 | 11 | 8 | 42.67 | 37.83 |
| Heterozygous for haplotype 2 | 327 | 14 | 11.5 | 56.18 | 53.98 |
| No haplotype 2 | 600 | 12 | 10 | 47.91 | 48.10 |
| Homozygous for haplotype 4 | 9 | 17 | 11 | 71.6 | 65.47 |
| Heterozygous for haplotype 4 | 123 | 13 | 14 | 50.40 | 65.07 |
| No haplotype 4 | 846 | 12 | 11 | 49.51 | 48.22 |
| Homozygous for haplotype 3 | 13 | 12 | 12 | 56.53 | 41.47 |
| Heterozygous for haplotype 3 | 211 | 13 | 13 | 51.33 | 57.09 |
| No haplotype 3 | 754 | 12 | 11 | 49.73 | 47.10 |
| Haplogenotype 1/2 | 206 | 13 | 10.75 | 54.31 | 47.73 |
| Haplogenotype 1/3 | 68 | 13 | 13.25 | 51.33 | 64.42 |
| Haplogenotype 1/4 | 129 | 12 | 12 | 45.87 | 51.80 |
| Haplogenotype 1/X | 104 | 10 | 10 | 44.71 | 42.79 |
| Haplogenotype 2/3 | 34 | 15.5 | 12 | 63.87 | 55.97 |
| Haplogenotype 2/4 | 48 | 17 | 11.25 | 76.87 | 55.74 |
| Haplogenotype 2/X | 39 | 13 | 11.5 | 54.89 | 49.22 |
| Haplogenotype 3/4 | 15 | 9 | 21 | 34.80 | 85.37 |
| Haplogenotype 3/X | 6 | 11 | 14.25 | 43.93 | 70.71 |
| Haplogenotype 4/X | 19 | 14 | 9 | 53.51 | 38.53 |
| Haplogenotype X/X | 7 | 9 | 3.5 | 35.40 | 13.70 |

X indicates a rare haplotype (for example, haplotypes 5, 6, or 7).
IQR = interquartile range.

References Cited

1. Abecasis G R, Cardon L R, Cookson W O. A general test of association for quantitative traits in nuclear families. *Am J Hum Genet.* 66:279-292 (2000).
2. Abecasis G R, Cookson W O, Cardon L R: Pedigree tests of transmission disequilibrium. *Eur J Hum Genet.* 8:545-551 (2000).
3. Ahn Y I, Ferrell R E, Hamman R F, Kamboh M I. Association of lipoprotein lipase gene variation with the physiological components of the insulin-resistance syndrome in the population of the San Luis Valley, Colo. *Diabetes Care* 16:1502-1506 (1993).
4. Ahn Y I, Kamboh M I, Hamman R F, Cole S A, Ferrell R E. Two DNA polymorphisms in the lipoprotein lipase gene and their associations with factors related to cardiovascular disease. *J Lipid Res* 34:421-428 (1993).
5. Allayee H, de Bruin T W, Michelle Dominguez K, Cheng L S, Ipp E, Cantor R M, Krass K L, Keulen E T, Aouizerat B E, Lusis A J, Rotter J I: Genome scan for blood pressure in Dutch dyslipidemic families reveals linkage to a locus on chromosome 4p. *Hypertension* 38:773-778 (2001).
6. Allison D B: Transmission-disequilibrium tests for quantitative traits. *Am J Hum Genet.* 60:676-690 (1997).
7. Aoki T, Yamazaki H, Tamaki T, Sato F, Kitahara M, Saito Y. Triglyceride lowering effect of pitavastatin in a guinea pig model of postprandial lipemia. *Arzneimittelforschung* 53:154-158 (2003).
8. Babaev V R, Patel M B, Semenkovich C F, Fazio S, Linton M F: Macrophage lipoprotein lipase promotes foam cell formation and atherosclerosis in low density lipoprotein receptor-deficient mice. *J Biol Chem* 275:26293-26299, 2000
9. Barrett J C, Fry B, Maller J, Daly M J. Haploview: analysis and visualization of LD and haplotype maps. *Bioinformatics* 21:263-265 (2005).
10. Bergman R N, Zaccaro D J, Watanabe R M, Haffner S M, Saad M F, Norris J M, Wagenknecht L E, Hokanson J E, Rotter J I, Rich S S. Minimal model-based insulin sensitivity has greater heritability and distinct genetic basis than homeostasis model assessment or fasting insulin. *Diabetes* 52:2168-2174, (2003).
11. Bey L, Maigret P, Laouenan H, Hamilton Mont. Induction of lipoprotein lipase gene expression in 3T3-L1 preadipocytes by atorvastatin, a cholesterol- and triglyceride-lowering drug. *Pharmacology* 2002; 66:51-56.
12. Boden G, Lebed B, Schatz M, Homko C, Lemieux S. Effects of acute changes of plasma free fatty acids on intramyocellular fat content and insulin resistance in healthy subjects. *Diabetes* 50:1612-1617 (2001).
13. Cabezas M C, de Bruin T W, Kock L A, Kortlandt W, Van Linde-Sibenius Trip M, Jansen H et al. Simvastatin improves chylomicron remnant removal in familial combined hyperlipidemia without changing chylomicron conversion. *Metabolism* 1993; 42:497-503.
14. Castellani L W, Gargalovic P, Febbraio M, Charugundla S, Jien M L, Lusis A J. Mechanisms mediating insulin resistance in transgenic mice overexpressing mouse apolipoprotein A-II. *J Lipid Res* 45:2377-2387 (2004).
15. Castellani L W, Navab M, Van Lenten B J, Hedrick C C, Hama S Y, Goto A M, Fogelman A M, Lusis A J. Overexpression of apolipoprotein AII in transgenic mice converts high density lipoproteins to proinflammatory particles. *J Clin Invest* 100:464-474 (1997).
16. Chasman D I, Posada D, Subrahmanyan L, Cook N R, Stanton Jr V P, Ridker P M. Pharmacogenetic study of statin therapy and cholesterol reduction. *JAMA* 291:2821-2827 (2004).
17. Clark A G, Weiss K M, Nickerson D A, Taylor S L, Buchanan A, Stengard J, Salomaa V, Vartiainen E, Perola M, Boerwinkle E, et al. Haplotype structure and population genetic inferences from nucleotide-sequence variation in human lipoprotein lipase Am 1. *Hum. Genet.* 63:595-612 (1998).
18. Cole S A, Aston C E, Hamman R F, Ferrell R E. Association of a PvuII RFLP at the lipoprotein lipase locus with fasting insulin levels in Hispanic men. *Genet Epidemiol* 10:177-188 (1993).
19. Daly M J, Rioux J D, Schaffner S F, Hudson T J, Lander E S: High-resolution haplotype structure in the human genome. *Nat Genet.* 29:229-232 (2001).
20. DeFronzo R A, Tobin J D, Andres R: Glucose clamp technique: a method for quantifying insulin secretion and resistance. *Am J Physiol* 237:E214-E223 (1979).
21. Despres J P, Lamarche B, Mauriege P, et al. Hyperinsulinemia as an independent risk factor for ischemic heart disease. *N Engl J Med* 334:952-7 (1996).
22. Eisenberg S. High density lipoprotein metabolism. *J Lipid Res* 25:1017-1058 (1984).
23. Elston R C, Buxbaum S, Jacobs K B, Olson J M. Haseman and Elston revisited. *Genet Epidemiol* 19:1-17 (2000).

24. Endo K, Miyashita Y, Saiki A, Oyama T, Koide N, Ozaki H et al. Atorvastatin and pravastatin elevated pre-heparin lipoprotein lipase mass of type 2 diabetes with hypercholesterolemia. *J Atheroscler Thromb* 11:341-347 (2004).
25. Felsenstein I. PHYLIP—phylogeny inference package (version 3.2). Cladistics, 5:164-166 (1989).
26. Freeman M S, Mansfield M W, Barrett J H, Grant P I Heritability of features of the insulin resistance syndrome in a community-based study of healthy families. *Diabet Med* 19:994-9 (2002).
27. Gabriel S B, Schaffner S F, Nguyen H, Moore J M, Roy J, Blumenstiel B, Higgins J, DeFelice M, Lochner A, Faggart M, Liu-Cordero S N, Rotimi C, Adeyemo A, Cooper R, Ward R, Lander E S, Daly M J, Altshuler D. The structure of haplotype blocks in the human genome. *Science* 296: 2225-2229 (2002).
28. Gagne E, Genest Jr J, Zhang H, Clarke L A, Hayden M R. Analysis of DNA changes in the LPL gene in patients with familial combined hyperlipidemia. Arterioscler Thromb 14:1250-1257 (1994).
29. Gaziano J M, Hennekens C H, O'Donnell C J, Breslow J L, Buring J E. Fasting triglycerides, high-density lipoprotein, and risk of myocardial infarction. *Circulation* 96:2520-5 (1997).
30. Goodarzi M O, Guo X, Taylor K D, Quinones M J, Saad M F, Yang H, Hsueh W A, Rotter J I. Lipoprotein lipase is a gene for insulin resistance in Mexican Americans. *Diabetes* 53:214-220 (2004).
31. Goodarzi M O, Guo X, Taylor K D, Quinones M J, Samayoa C, Yang H, Saad M F, Palotie A, Krauss R M, Hsueh W A, Rotter J I. Determination and use of haplotypes: Ethnic comparison and association of the lipoprotein lipase gene and coronary artery disease in Mexican-Americans. *Genet Med* 5:322-327 (2003).
32. Goodarzi M O, Taylor K D, Scheuner M T, Antoine H J, Guo X, Shah P K, Rotter J I. Haplotypes in the Lipoprotein Gene Influence High-Density Lipoprotein Cholesterol Response to Statin Therapy and progression of Atherosclerosis in Coronary Artery Bypass Grafts. *Pharmacogenomics J* Advance Online Publication 1-8 (2006).
33. Goodarzi M O, Wong H, Quinones M J, Taylor K D, Guo X, Castellani L W, Antoine H J, Yang H, Hsueh W A, Rotter J I. The 3' untranslated region of the lipoprotein lipase gene: Haplotype structure and association with post-heparin plasma lipase activity. *J Clin Endocrinol Metab* 90:4816-4823 (2005).
34. Groenemeijer B E, Hallman M D, Reymer P W, Gagne E, Kuivenhoven J A, Bruin T, Jansen H, Lie K I, Bruschke A V, Boerwinkle E, Hayden M R, Kastelein J J. Genetic variant showing a positive interaction with blocking agents with a beneficial influence on lipoprotein lipase activity, HDL cholesterol, and triglyceride levels in coronary artery disease patients. The Ser447-stop substitution in the lipoprotein lipase gene. REGRESS Study Group. *Circulation* 95:2628-2635 (1997).
35. Guerre-Millo M. Adipose tissue hormones. *J Endocrinol Invest* 25:855-861 (2002).
36. Haffner S M, Stern M P, Hazuda H P, Pugh J, Patterson J K, Malina R. Upper body and centralized adiposity in Mexican Americans and non-Hispanic whites: relationship to body mass index and other behavioral and demographic variables. *Int J Obes* 10:493-502 (1986).
37. Hanley A J, Williams K, Stern M P, Haffner S M. Homeostasis model assessment of insulin resistance in relation to the incidence of cardiovascular disease: the San Antonio Heart Study. *Diabetes Care* 25:1177-1184 (2002).
38. Haseman J K, Elston R C. The investigation of linkage between a quantitative trait and a marker locus. *Behav Genet.* 2:3-19 (1972).
39. Heizmann C, Kirchgessner T, Kwiterovich P O, Ladias J A, Derby C, Antonarakis S E, Lusis A J. DNA polymorphism haplotypes of the human lipoprotein lipase gene: possible association with high density lipoprotein levels. *Hum Genet.* 86:578-584 (1991).
40. Henkin L, Bergman R H, Bowden D W, Ellsworth D L, Haffner S M, Langefeld C D, Mitchell B D, Norris J M, Rewers M, Saad M F, Stamm E, Wagenknecht L E, Rich S S. Genetic epidemiology of insulin resistance and visceral adiposity. The IRAS Family Study design and methods. *Ann Epidemiol* 13:211-217 (2003).
41. Hensley L L, Ranganathan G, Wagner E M, Wells B D, Daniel J C, Vu D, Semenkovich C F, Zechner R, Kern P A. Transgenic mice expressing lipoprotein lipase in adipose tissue. Absence of the proximal 3'-untranslated region causes translational upregulation. *J Biol Chem* 278:32702-32709 (2003).
42. Herbert V, Lau K S, Gottlieb C W, Bleicher S J. Coated charcoal immunoassay of insulin. *J Clin Endocrinol Metab* 25:1375-1384 (1965).
43. Hirschhorn J N, Lohmueller K, Byrne E, Hirschhorn K. A comprehensive review of genetic association studies. *Genet Med* 4:45-61 (2002).
44. Hofacker I L. Vienna RNA secondary structure server. *Nucleic Acids Res* 31:3429-3431 (2003).
45. Hokanson J E, Langefeld C D, Mitchell B D, Lange L A, Goff D C, Jr., Haffner S M, Saad M F, Rotter J I. Pleiotropy and heterogeneity in the expression of atherogenic lipoproteins: the IRAS Family Study. *Hum Hered* 55:46-50 (2003).
46. Holmer S R, Hengstenberg C, Mayer B, Döring A, Löwel H, Engel S, Hense H W, Wolf M, Klein G, Riegger G A, Schunkert H. Lipoprotein lipase gene polymorphism, cholesterol subfractions and myocardial infarction in large samples of the general population. *Cardiovasc Res* 47:806-812 (2000).
47. Hong Y, Pedersen N L, Brismar K, de Faire U. Genetic and environmental architecture of the features of the insulin-resistance syndrome. *Am J Hum Genet.* 60:143-52 (1997).
48. Humphries S E, Nicaud V, Margalef J, Tiret L, Talmud P J. Lipoprotein lipase gene variation is associated with a paternal history of premature coronary artery disease and fasting and postprandial plasma triglycerides: the European Atherosclerosis Research Study (EARS). *Arterioscler Thromb Vasc Biol* 18:526-534 (1998).
49. Jemaa R, Tuzet S, Portos C, Betoulle D, Apfelbaum M, Fumeron F. Lipoprotein lipase gene polymorphisms: Associations with hypertriglyceridemia and body mass index in obese people. *Int J Obes Relat Metab Disord* 19:270-274 (1995).
50. Jukema J W, van Boven A J, Groenemeijer B, Zwinderman A H, Reiber J H, Bruschke A V et al. The Asp9 Asn mutation in the lipoprotein lipase gene is associated with increased progression of coronary atherosclerosis. REGRESS Study Group, Interuniversity Cardiology Institute, Utrecht, The Netherlands. Regression Growth Evaluation Statin Study. *Circulation* 94:1913-1918 (1996).
51. Kasim S E, LeBoeuf R C, Khilnani S, Tallapaka L, Dayananda D, Jen K L. Mechanisms of triglyceride-lowering effect of an HMG-CoA reductase inhibitor in a hypertriglyceridemic animal model, the Zucker obese rat. *J Lipid Res* 33:1-7 (1992).
52. Kobayashi J, Maruyama T, Masuda M, Shinomiya M. Effect of atorvastatin treatment on lipoprotein lipase mass in the pre-heparin plasma in Japanese hyperlipidemic subjects. *Clin Chim Acta* 314:261-264 (2001).
53. Kolterman O G, Insel J, Saekow M, Olefsky J M. Mechanisms of insulin resistance in human obesity: evidence for receptor and postreceptor defects. *J Clin Invest* 65:1272-1284 (1980).
54. Kozaki K, Gotoda T, Kawamura M, Shimano H, Yazaki Y, Ouchi Y, Orimo H, Yamada N. Mutational analysis of human lipoprotein lipase by carboxy-terminal truncation. *J Lipid Res* 34:1765-1772 (1993).
55. Lee W J, Sheu W H, Jeng C Y, Young M S, Chen Y T. Associations between lipoprotein lipase gene polymorphisms and insulin resistance in coronary heart disease. *Chung-Hua I Hsuch Tsa Chih* (*Chinese Medical Journal*) 63:563-572 (2000).
56. Lewontin R C. The interaction of selection and linkage. I. General considerations; heterotic models. *Genetics* 49:49-67 (1964).
57. Livak K J. Allelic discrimination using fluorogenic probes and the 5' nuclease assay. *Genet Anal* 14:143-149 (1999).
58. Malloy M J, Kane J P. A risk factor for atherosclerosis: triglyceride-rich lipoproteins. *Adv Intern Med* 47:111-136 (2001).
59. Mamputu J C, Desfaits A C, Renier G. Lipoprotein lipase enhances human monocyte adhesion to aortic endothelial cells. *J Lipid Res* 38:1722-1729 (1997).
60. Mamputu J C, Levesque L, Renier G. Proliferative effect of lipoprotein lipase on human vascular smooth muscle cells. *Arterioscler Thromb Vasc Biol* 20:2212-2219 (2000).
61. Matthews D R, Hosker J P, Rudenski A S, Naylor B A, Treacher D F, Turner R C. Homeostasis model assessment: insulin resistance and beta-cell function from fasting plasma glucose and insulin concentrations in man. *Diabetologia* 28:412-419 (1985).
62. Mattu R K, Needham E W, Morgan R, Rees A, Hackshaw A K, Stocks J, Elwood P C, Galton D J. DNA variants at the LPL gene locus associate with angiographically defined severity of atherosclerosis and serum lipoprotein levels in a Welsh population. *Arterioscler Thromb Vasc Biol* 14:1090-1097 (1994).
63. Mead J R, Ramji D P. The pivotal role of lipoprotein lipase in atherosclerosis. *Cardiovasc Res* 55:261-269 (2002).
64. Mitchell B D, Kammerer C M, Mahaney M C, et al. Genetic analysis of the IRS. Pleiotropic effects of genes influencing insulin levels on lipoprotein and obesity measures. *Arterioscler Thromb Vasc Bio* 16:281-8 (1996).
65. Motulsky A G, Brunzell J D: Genetics of coronary atherosclerosis. In *The Genetic Basis of Common Diseases*, 2nd ed. King R A, Rotter J I, Motulsky A G, Eds. New York, Oxford University Press, Inc., 105-126 (2002).
66. Murthy V, Julien P, Gagne C. Molecular pathobiology of the human lipoprotein lipase gene. *Pharmacol Ther* 70:101-135 (1996).
67. Neel J V, Weder A B, Julius S. Type II diabetes, essential hypertension, and obesity as 'syndromes of impaired genetic homeostasis': the 'thrifty genotype' hypothesis enters the 21st century. *Perspect Biol Med* 42:44-74 (1998).
68. Nickerson D A, Taylor S L, Weiss K M, Clark A G, Hutchinson R G, Stengard J, Salomaa V, Vartiainen E, Boerwinkle E, Sing C F. DNA sequence diversity in a 9.7-kb region of the human lipoprotein lipase gene. *Nat Genet.* 19:233-240, (1998).
69. Nicklas B J, Ferrell R E, Rogus E M, Berman D M, Ryan A S, Dennis K E, Goldberg A P. Lipoprotein lipase gene variation is associated with adipose tissue lipoprotein lipase activity, and lipoprotein lipid and glucose concentrations in overweight postmenopausal women. *Hum Genet.* 106:420-424 (2000).
70. Nilsson-Ehle P, Schotz M C. A stable, radioactive substrate emulsion for assay of lipoprotein lipase. *J Lipid Res* 17:536-541 (1976).
71. Norris J M, Langefeld C D, Scherzinger A L, Rich S S, Bookman E, Beck S R, Saad M F, Haffner S M, Bergman R H, Bowden D W, Wagenknecht L E. Quantitative trait loci for abdominal fat and BMI in Hispanic-Americans and African-Americans: the IRAS Family study. *Int J Obes* (*Lond*) 29:67-77 (2005).
72. O'Connell J R, Weeks D E: PedCheck: a program for identification of genotype incompatibilities in linkage analysis. *Am J Hum Genet.* 63:259-266 (1998).
73. Okosun I S, Liao Y, Rotimi C N, Prewitt T E, Cooper R S. Abdominal adiposity and clustering of multiple metabolic syndrome in white, black and Hispanic Americans. *Ann Epidemiol* 10:263-270 (2000).
74. Pacini G, Bergman R H. MINMOD: A computer program to calculate insulin sensitivity and pancreatic responsivity from the frequently sampled intravenous glucose tolerance test. *Comput Methods Programs Biomed* 23:113-122 (1986).
75. Park Y W, Zhu S, Palaniappan L, Heshka S, Carnethon M R, Heymsfield S B. The metabolic syndrome: prevalence and associated risk factor findings in the US population from the Third National Health and Nutrition Examination Survey, 1988-1994. *Arch Intern Med* 163:427-436 (2003).
76. Peacock R E, Hamsten A, Nilsson-Ehle P, Humphries S E. Associations between lipoprotein lipase gene polymorphisms and plasma correlations of lipids, lipoproteins and lipase activities in young myocardial infarction survivors and age-matched healthy individuals from Sweden. *Atherosclerosis* 97:171-185 (1992).
77. Pesole G, Liuni S, Grillo G, Licciulli F, Mignone F, Gissi C, Saccone C. UTRdb and UTRsite: Specialized databases of sequences and functional elements of 5' and 3' untranslated regions of eukaryotic mRNAs. *Nucleic Acids Res* 30:335-340 (2000). Update 2002.
78. Phillips D I, Caddy S, Hic V, et al. Intramuscular triglyceride and muscle insulin sensitivity: evidence for a relationship in nondiabetic subjects. *Metabolism* 45:947-950 (1996).
79. Preiss-Landl K, Zimmermann R, Hammerle G, Zechner R. Lipoprotein lipase: The regulation of tissue specific expression and its role in lipid and energy metabolism. *Curr Opin Lipidol* 13:471-481 (2002).
80. Proenza A M, Poissonnet C M, Ozata M, Ozen S, Guran S, Palou A, Strosberg A D: Association of sets of alleles of genes encoding beta3-adrenoreceptor, uncoupling protein 1 and lipoprotein lipase with increased risk of metabolic complications in obesity. *Int J Obes Relat Metab Disord* 24:93-100 (2000).
81. Pulawa L K, Eckel R H: Overexpression of muscle lipoprotein lipase and insulin sensitivity. *Curr Opin Clin Nutr Metab Care* 5:569-574 (2002).
82. Pyorala M, Miettinen H, Laakso M, Pyorala K: Hyperinsulinemia predicts coronary heart disease risk in healthy middle-aged men: the 22-year follow-up results of the Helsinki Policemen Study. *Circulation* 98:398-404 (1998).
83. Qin Z S, Niu T, Liu J S. Partition-ligation-expectation-maximization algorithm for haplotype inference with single-nucleotide polymorphisms. *Am J Hum Genet.* 71:1242-1247 (2002).
84. Quinones M J, Hernandez-Pampaloni M, Schelbert H, Bulnes-Enriquez I, Jimenez X, Hernandez G, De La Rosa R, Chon Y, Yang H, Nicholas S B, Modilevsky T, Yu K, Van Herle K, Castellani L W, Elashoff R, Hsuch W A. Coronary vasomotor abnormalities in insulin-resistant individuals. *Ann Intern Med* 140:700-708 (2004).
85. Ranganathan G, Li C, Kern P A. The translational regulation of lipoprotein lipase in diabetic rats involves the 3'-untranslated region of the lipoprotein lipase mRNA. *J Biol Chem* 275:40986-40991 (2000).
86. Ranganathan G, Vu D, Kern P A 1997 Translational regulation of lipoprotein lipase by epinephrine involves a trans-acting binding protein interacting with the 3' untranslated region. *J Biol Chem* 272:2515-2519 (1997).
87. Rioux J D, Daly M J, Silverberg M S, Lindblad K, Steinhart H, Cohen Z et al. Genetic variation in the 5q31 cytokine gene cluster confers susceptibility to Crohn disease. *Nat Genet.* 29:223-228 (2001).
88. S.A.G.E.: Statistical Analysis for Genetic Epidemiology [computer program]. Cork, Ireland: Statistical Solutions, Ltd., (2002).
89. Sambrook J, Fritsch E, Maniatis T. Molecular Cloning. Cold Spring Harbor Laboratory: New York, (1989).
90. Samuels M E, Forbey K C, Reid J E, Abkevich V, Bulka K, Wardell B R, Bowen B R, Hopkins P N, Hunt S C, Ballinger D G, Skolnick M H, Wagner S. Identification of a common variant in the lipoprotein lipase gene in a large Utah kindred ascertained for coronary heart disease: the 93G/D9N variant predisposes to low HDL-C/high triglycerides. *Clin Genet.* 59:88-98 (2001).
91. SAS [computer program]. Release 8.0. Cary, N.C.: SAS Institute, 1999.
92. Sasaki J, Yamamoto K, Kobori S, Setoguchi Y, Sato Y, Matsunaga A et al. Effects of fluvastatin, a new inhibitor of HMG-CoA reductase, and niceritrol on serum lipids, lipoproteins and cholesterol ester transfer activity in primary hypercholesterolemic patients. *Int J Clin Pharmacol Ther* 33:420-426 (1995).
93. Sato A, Watanabe K, Fukuzumi H, Hase K, Ishida F, Kamei T. Effect of simvastatin (MK-733) on plasma triacylglycerol levels in rats. Biochem Pharmacol 41:1163-1172 (1991).
94. Schneider J G, von Eynatten M, Parhofer K G, Volkmer J E, Schiekofer S, Hamann A et al. Atorvastatin improves diabetic dyslipidemia and increases lipoprotein lipase activity in vivo. *Atherosclerosis* 175:325-331 (2004).
95. Sobel E, Lange K. Descent graphs in pedigree analysis: applications to haplotyping, location scores, and marker-sharing statistics. *Am J Hum Genet.* 58:1323-1337 (1996).
96. Spielman R S, McGinnis R E, Ewens W J. Transmission test for linkage disequilibrium: the insulin gene region and insulin-dependent diabetes mellitus (IDDM). *Am J Hum Genet.* 52:506-516 (1993).
97. Taylor K D, Scheuner M T, Yang H, Wang Y, Haritunians T, Fischel-Ghodsian N et al. Lipoprotein lipase locus and progression of atherosclerosis in coronary-artery bypass grafts. Genet Med 6:481-486 (2004).
98. Templeton A R, Clark A G, Weiss K M, Nickerson D A, Boerwinkle E, Sing C F. Recombinational and mutational hotspots within the human lipoprotein lipase gene. *Am J Hum Genet.* 66:69-83 (2000).
99. Templeton A R, Sing C F, Kessling A, Humphries S. A cladistic analysis of phenotype associations with haplotypes inferred from restriction endonuclease mapping. II. The analysis of natural populations. *Genetics* 120:1145-1154 (1988).
100. Templeton A R, Weiss K M, Nickerson D A, Boerwinkle E, Sing C F. Cladistic structure within the human lipoprotein lipase gene and its implications for phenotypic association studies. *Genetics* 156:1259-1275 (2000).
101. Templeton A R. Cladistic approaches to identifying determinants of variability in multifactorial phenotypes and the evolutionary significance of variation in the human genome. *CIBA Found Symp* 197:259-277 (1996).
102. The Post Coronary Artery Bypass Graft Trial Investigators. The effect of aggressive lowering of low-density lipoprotein cholesterol levels and low-dose anticoagulation on obstructive changes in saphenous-vein coronary-artery bypass grafts. *N Engl J Med* 336:153-162 (1997).
103. Ukkola O, Garenc C, Perusse L, Bergeron J, Despres J P, Rao D C, Bouchard C. Genetic variation at the lipoprotein lipase locus and plasma lipoprotein and insulin levels in the Quebec Family Study. *Atherosclerosis* 158:199-206 (2001).
104. Wagenknecht L E, Mayer E J, Rewers M, Haffner S, Selby J, Borok G M, Henkin L, Howard G, Savage P J, Saad M F, Bergman R H, Hamman R. The insulin resistance atherosclerosis study (IRAS) objectives, design, and recruitment results. *Ann Epidemiol* 5:464-472 (1995).
105. Wallace T M, Matthews D R. The assessment of insulin resistance in man. *Diabet Med* 19:527-34 (2002).
106. Wang N, Akey J M, Zhang K, Chakraborty R, Jin L. Distribution of recombination crossovers and the origin of haplotype blocks: the interplay of population history, recombination, and mutation. *Am J Hum Genet.* 71:1227-1234 (2002).
107. Wu D A, Bu X, Warden C H, Shen D D, Jeng C Y, Sheu W H, Fuh M M, Katsuya T, Dzau V J, Reaven G M, Lusis A J, Rotter J I, Chen Y D. Quantitative trait locus mapping of human blood pressure to a genetic region at or near the lipoprotein lipase gene locus on chromosome 8p22. *J Clin Invest* 97:2111-2118 (1996).
108. Yost T J, Froyd K K, Jensen D R, Eckel R H. Change in skeletal muscle lipoprotein lipase activity in response to insulin/glucose in non-insulin dependent diabetes mellitus. *Metabolism* 44:786-790 (1995).
109. Zechner R, Newman T C, Steiner E, Breslow J L. The structure of the mouse lipoprotein lipase gene: a B1 repetitive element is inserted into the 3' untranslated region of the mRNA. *Genomics* 11:62-76 (1991).
110. Zeger S L, Liang K Y. Longitudinal data analysis for discrete and continuous outcomes. *Biometrics* 42:121-130 (1986).
111. Zhang H, Henderson H, Gagne S E, Clee S M, Miao L, Liu G, Hayden M R. Common sequence variants of lipoprotein lipase: standardized studies of in vitro expression and catalytic function. *Biochim Biophys Acta* 1302:159-166 (1996).

The invention claimed is:

1. A method of determining that a human subject has a genetic predisposition for a biological condition, said method comprising:
 a) obtaining a biological sample from said subject, said sample containing nucleic acids from said subject; and
 b) detecting in said nucleic acids haplotype 12-1 in the lipoprotein lipase (LPL) gene, said haplotype 12-1 comprising:
  i) a T at the position corresponding to position 8393 of SEQ ID NO: 25;
  ii) a C at the position corresponding to position 9040 of SEQ ID NO: 25;
  iii) SEQ ID NO: 60, or the complement thereof, in exon 10 of the LPL gene;
  iv) SEQ ID NO: 64, or the complement thereof, in exon 10 of the LPL gene;
  v) SEQ ID NO: 68, or the complement thereof, m exon 10 of the LPL gene;
  vi) SEQ ID NO: 70, or the complement thereof, m exon 10 of the LPL gene;
  vii) SEQ ID NO: 72, or the complement thereof, m exon 10 of the LPL gene;
  viii) SEQ ID NO: 74, or the complement thereof, m exon 10 of the LPL gene;
  ix) SEQ ID NO: 78, or the complement thereof, m exon 10 of the LPL gene;
  x) SEQ ID NO: 80, or the complement thereof, m exon 10 of the LPL gene;
  xi) SEQ ID NO: 82, or the complement thereof, in exon 10 of the LPL gene; and
  xii) SEQ ID NO: 84, or the complement thereof; in exon 10 of the LPL gene;

wherein said biological condition is a decreased risk of graft worsening and/or graft occlusion of a coronary artery bypass graft (CABG) and/or a decreased diastolic blood pressure (DBP).

2. A method of determining that a human subject has a genetic predisposition for a biological condition, said method comprising:
   a) obtaining a biological sample from said subject, said sample containing nucleic acids from said subject; and
   b) detecting in said nucleic acids haplotype 12-2 in the lipoprotein lipase (LPL) gene, said haplotype 12-2 comprising:
   i) a T at the position corresponding to position 8393 of SEQ ID NO.: 25;
   ii) a C at the position corresponding to position 9040 of SEQ ID NO: 25;
   iii) SEQ ID NO: 60, or the complement thereof, in exon 10 of the LPL gene;
   iv) SEQ ID NO: 64, or the complement thereof, in exon 10 of the LPL gene;
   v) SEQ ID NO: 68, or the complement thereof, in exon 10 of the LPL gene;
   vi) SEQ ID NO: 70, or the complement thereof, in exon 10 of the LPL gene;
   vii) SEQ ID NO: 72, or the complement thereof, in exon 10 of the LPL gene;
   viii) SEQ ID NO: 75, or the complement thereof, in exon 10 of the LPL gene
   ix) SEQ ID NO: 78, or the complement thereof, in exon 10 of the LPL gene;
   x) SEQ ID NO: 80, or the complement thereof; in exon 10 of the LPL gene;
   xi) SEQ ID NO: 82, or the complement thereof, in exon 10 of the LPL gene; and
   xii) SEQ ID NO: 84, or the complement thereof, in exon 10 of the LPL gene;
wherein said biological condition is a decreased level of high-density lipoprotein cholesterol (HDL-C) and/or a decreased amount of triglyceride (TG) reduction in response to lovastatin therapy.

3. A method of determining that a human subject has a genetic predisposition for a biological condition, said method comprising:
   a) obtaining a biological sample from said subject, said sample containing nucleic acids from said subject; and
   b) detecting in said nucleic acids haplotype 12-4 in the lipoprotein lipase (LPL) gone, said haplotype 12-4 comprising:
   i) a G at the position corresponding to position 8393 of SEQ ID NO: 25;
   ii) a G at the position corresponding to position 9040 of SEQ ID NO: 25;
   iii) SEQ ID NO: 61, or the complement thereof, in exon 10 of the LPL gone;
   iv) SEQ ID NO: 64, or the complement thereof, in exon 10 of the LPL gene;
   v) SEQ ID NO: 69, or the complement thereof, in exon 10 of the LPL gene;
   vi) SEQ ID NO: 70, or the complement thereof in exon 10 of the LPL gene;
   vii) SEQ ID NO: 73, or the complement thereof; in exon 10 of the LPL gene;
   viii) SEQ ID NO: 74, or the complement thereof, in exon 10 of the LPL gene;
   ix) SEQ ID NO: 79, or the complement thereof, in exon 10 of the LPL gene;
   x) SEQ ID NO: 81, or the complement thereof, in exon 10 of the LPL gene;
   xi) SEQ ID NO: 83, or the complement thereof, in exon 10 of the LPL gene; and
   xii) SEQ ID NO: 84, or the complement thereof, in exon 10 of the LPL gene;
wherein said biological condition is an increased diastolic blood pressure (DBP), an increased high-density lipoprotein cholesterol (HDL-C), and/or a decreased amount of HDL-C reduction in response to lovastatin therapy.

* * * * *

UNITED STATES PATENT AND TRADEMARK OFFICE
CERTIFICATE OF CORRECTION

PATENT NO. : 8,178,294 B2
APPLICATION NO. : 11/564243
DATED : May 15, 2012
INVENTOR(S) : Kent D. Taylor et al.

It is certified that error appears in the above-identified patent and that said Letters Patent is hereby corrected as shown below:

Page 1, Column 1, at (73) Assignee: please insert the following additional Assignee under Cedars-Sinai Medical Center, Los Angeles, CA (US):

--The Regents of the University of California, Oakland, CA (US)--

Signed and Sealed this
Twenty-seventh Day of November, 2012

David J. Kappos
*Director of the United States Patent and Trademark Office*

SEQUENCE LISTING

<160> NUMBER OF SEQ ID NOS: 85

<210> SEQ ID NO 1
<211> LENGTH: 28

```
<212> TYPE: DNA
<213> ORGANISM: Artificial
<220> FEATURE:
<223> OTHER INFORMATION: Forward Primer

<400> SEQUENCE: 1
tcaagtcatt aaaatcaatc tagccttt                                          28

<210> SEQ ID NO 2
<211> LENGTH: 35
<212> TYPE: DNA
<213> ORGANISM: Artificial
<220> FEATURE:
<223> OTHER INFORMATION: Reverse primer

<400> SEQUENCE: 2
ttctctttag attttatatt ccattttta ctatg                                   35

<210> SEQ ID NO 3
<211> LENGTH: 25
<212> TYPE: DNA
<213> ORGANISM: Artificial
<220> FEATURE:
<223> OTHER INFORMATION: Forward primer

<400> SEQUENCE: 3
cctggataat caaagattca aacca                                             25

<210> SEQ ID NO 4
<211> LENGTH: 25
<212> TYPE: DNA
<213> ORGANISM: Artificial
<220> FEATURE:
<223> OTHER INFORMATION: Reverse primer

<400> SEQUENCE: 4
ggagacaggt tgagattatc ttgga                                             25

<210> SEQ ID NO 5
<211> LENGTH: 29
<212> TYPE: DNA
<213> ORGANISM: Artificial
<220> FEATURE:
<223> OTHER INFORMATION: Forward primer

<400> SEQUENCE: 5
cataaaatga attacacaga gatcgctat                                         29

<210> SEQ ID NO 6
<211> LENGTH: 33
<212> TYPE: DNA
<213> ORGANISM: Artificial
<220> FEATURE:
<223> OTHER INFORMATION: Reverse primer

<400> SEQUENCE: 6
tcaatcctaa cttagagttt ttttaaatta aca                                    33

<210> SEQ ID NO 7
<211> LENGTH: 24
<212> TYPE: DNA
<213> ORGANISM: Artificial
<220> FEATURE:
<223> OTHER INFORMATION: Forward primer

<400> SEQUENCE: 7
gtggcctgag tgtgacagtt aatt                                              24
```

<210> SEQ ID NO 8
<211> LENGTH: 25
<212> TYPE: DNA
<213> ORGANISM: Artificial
<220> FEATURE:
<223> OTHER INFORMATION: Reverse primer

<400> SEQUENCE: 8
atcaaaagca ctgttcacaa aggta                                          25

<210> SEQ ID NO 9
<211> LENGTH: 23
<212> TYPE: DNA
<213> ORGANISM: Artificial
<220> FEATURE:
<223> OTHER INFORMATION: Forward primer

<400> SEQUENCE: 9
ttgtgaaatg ccatgacaag tct                                            23

<210> SEQ ID NO 10
<211> LENGTH: 21
<212> TYPE: DNA
<213> ORGANISM: Artificial
<220> FEATURE:
<223> OTHER INFORMATION: Reverse primer

<400> SEQUENCE: 10
ccagtcagct ttagcccaga a                                              21

<210> SEQ ID NO 11
<211> LENGTH: 20
<212> TYPE: DNA
<213> ORGANISM: Artificial
<220> FEATURE:
<223> OTHER INFORMATION: Forward primer

<400> SEQUENCE: 11
tccatgtggc agctgttagc                                                20

<210> SEQ ID NO 12
<211> LENGTH: 27
<212> TYPE: DNA
<213> ORGANISM: Artificial
<220> FEATURE:
<223> OTHER INFORMATION: Reverse primer

<400> SEQUENCE: 12
gagtagtgaa ggtcacatgc ttagtgt                                        27

<210> SEQ ID NO 13
<211> LENGTH: 17
<212> TYPE: DNA
<213> ORGANISM: Artificial
<220> FEATURE:
<223> OTHER INFORMATION: probe

<400> SEQUENCE: 13
cctgggtttc ctacaat                                                   17

<210> SEQ ID NO 14
<211> LENGTH: 17
<212> TYPE: DNA
<213> ORGANISM: Artificial
<220> FEATURE:
<223> OTHER INFORMATION: probe

```
<400> SEQUENCE: 14
cctgggtttc ctagaat                                                    17

<210> SEQ ID NO 15
<211> LENGTH: 17
<212> TYPE: DNA
<213> ORGANISM: Artificial
<220> FEATURE:
<223> OTHER INFORMATION: probe

<400> SEQUENCE: 15
ctcacccttc ttgaaga                                                    17

<210> SEQ ID NO 16
<211> LENGTH: 16
<212> TYPE: DNA
<213> ORGANISM: Artificial
<220> FEATURE:
<223> OTHER INFORMATION: probe

<400> SEQUENCE: 16
tcacccttct ggaaga                                                     16

<210> SEQ ID NO 17
<211> LENGTH: 18
<212> TYPE: DNA
<213> ORGANISM: Artificial
<220> FEATURE:
<223> OTHER INFORMATION: probe

<400> SEQUENCE: 17
cacatttagt ataaaagc                                                   18

<210> SEQ ID NO 18
<211> LENGTH: 18
<212> TYPE: DNA
<213> ORGANISM: Artificial
<220> FEATURE:
<223> OTHER INFORMATION: probe

<400> SEQUENCE: 18
cacatttagt ataaacgc                                                   18

<210> SEQ ID NO 19
<211> LENGTH: 18
<212> TYPE: DNA
<213> ORGANISM: Artificial
<220> FEATURE:
<223> OTHER INFORMATION: probe

<400> SEQUENCE: 19
agcatgatca tgtattat                                                   18

<210> SEQ ID NO 20
<211> LENGTH: 19
<212> TYPE: DNA
<213> ORGANISM: Artificial
<220> FEATURE:
<223> OTHER INFORMATION: probe

<400> SEQUENCE: 20
cagcatgatc atgtagtat                                                  19

<210> SEQ ID NO 21
<211> LENGTH: 13
```

```
<212> TYPE: DNA
<213> ORGANISM: Artificial
<220> FEATURE:
<223> OTHER INFORMATION: probe

<400> SEQUENCE: 21
ccagcctgac ttc                                                          13

<210> SEQ ID NO 22
<211> LENGTH: 14
<212> TYPE: DNA
<213> ORGANISM: Artificial
<220> FEATURE:
<223> OTHER INFORMATION: probe

<400> SEQUENCE: 22
accagcctca cttc                                                         14

<210> SEQ ID NO 23
<211> LENGTH: 15
<212> TYPE: DNA
<213> ORGANISM: Artificial
<220> FEATURE:
<223> OTHER INFORMATION: probe

<400> SEQUENCE: 23
ccagagcgtc agtac                                                        15

<210> SEQ ID NO 24
<211> LENGTH: 15
<212> TYPE: DNA
<213> ORGANISM: Artificial
<220> FEATURE:
<223> OTHER INFORMATION: probe

<400> SEQUENCE: 24
ccagagcatc agtac                                                        15

<210> SEQ ID NO 25
<211> LENGTH: 9734
<212> TYPE: DNA
<213> ORGANISM: Homo sapiens

<400> SEQUENCE: 25
tgtaacacaa aattaaaata agtagaatta gttttcagta tttcctatat ttggaaaaca         60
atatttatat tcattttgtt tcttttagtt ttattttttgg cagaactgta agcaccttca       120
ttttcttttt cttccaaagg aggagtttaa ctaccctctg acaatgtcc atctcttggg         180 atacagcctt ggagcccatg ctgctggcat tgcaggaagt ctgaccaata agaaagtcaa       240
cagaattact ggtaagaaag caatttcgtt ggtcttatca taagaggtga aaagactgtc       300
attctgagag agaatcagaa caaattttgt taaatacccca catgtgtggt gttcttcccg      360
gagacatgac cagcacttga ttatctcatt gtagggctct ttattaggga taagaaaaaa      420
cacagacgct ctcactggct tactatccac tggcaatagc acagaaataa agcataatta       480
cacacaatgc ctgcagattt ctctgggaag cctgtttcct cccactctca gctctgtgtt       540
ttagtagtgt aaatgcacat cagtactagg acaaaagaag aaggaccaat tccagaggcc       600
acttcgaaag aagaccgtca tctaggcaaa ggtgtggcat acacacagag agaaagaacc       660
caccactgtt tatacatctt ctcgacatat tcagaaataa tctacaaaag gaaatccagc       720
catcctgagt ggaaattgct gcataaggct agtttaagag actcaaattc attttagaag      780
gagccaagcc tccttttatg tctctctaag taaagatacc atgactgtag aataggagct       840
```

```
aataagaatc taaatagctg ccagtgcatt caaatgatga gcagtgacat gcgaatgtca    900
tacgaatgga aatttacaaa tctgtgttcc tgcttttttc cctttttaagg cctcgatcca    960
gctggaccta actttgagta tgcagaagcc ccgagtcgtc tttctcctga tgatgcagat   1020
tttgtagacg tcttacacac attcaccaga gggtcccctg gtcgaagcat tggaatccag   1080
aaaccagttg ggcatgttga catttacccg aatggaggta cttttcagcc aggatgtaac   1140
attggagaag ctatccgcgt gattgcagag agaggacttg gaggtaaata ttatttagaa   1200
gcgaattaaa tgtgactctt atccttaacc cttattgacc caatgtccta ctcagtagct   1260
tcaaagtatg tagttttcat atacacattt ggccaaatta tgtttctgaa gaattctgca   1320
atgttcagca tgaccacctt agagccaggc agacagccat tttatctttt atttactata   1380
ctgtaggcta cactgagcag tgcacttaca gtagcaagag aaaaaggtgg gattttagac   1440
aggaagactc cactgacctc aataatggca tcataaaatg ctatctggcc acatgttgtc   1500
ataccttgaa tgtagctgca aagccaatgg aaagatttta gatgttactg gaacagaaga   1560
tgttaattag cataaatctt ccaaaatgtt cagaacataa tgttagctta atgttttact   1620
ttaataatgt tagcttgtgt taaatttatg attttttgttt gtttgttttt tgagatagag   1680
tcttattcta ttgcccaagc tggggtgcag tcacacaatc acagcgactt gcaatgttgc   1740
ccaggctggt ctcaaactcc tggcctcaag tgatcctcct gcctcagcct cccaaagttc   1800
tgggattgca gctgtgagcc accacgccca gtttacgatt tatttttaag agccccttgc   1860
atactttata gacattggga cctacctagg atattctcgt tattttgtg cacgtaatag   1920
aacttagagc atattgttac tattttcgat tgtcctaaaa acttacaagg aattcattct   1980
tatggcattg ctgattattt ctatgttcat ttgatataaa agagtgttag taggggcaga   2040
accctcaatt gtacataata tcaatgataa aatacaattc atttaacaat taccctctta   2100
agatgtggtt tctagaaata caaattgtcc ctaacttaca gttttccaac tttacaattg   2160
ggctgtaaca ccatttttaag ttgagaagca cgtgatggtt tgacttaaaa cttttttgaca   2220
ttatgatggg ttttgggggt attaagtgca ttttgactta cagtatttt gacttatgaa   2280
gaatttattg taaggcaagg ggcaggtata tgtttctaga agcacctaga agtgttagac   2340
actttcaatg taagagaagg atgagataaa caaggaaatc acacctccac cttggaggct   2400
tattacagct tcataaacat actcataaat ataagaagca caaaagtcaa aaattccctg   2460
tgaacttgca actttcactc tcttgaaggt gggtgggccg ctaccaccaa gaatatctcc   2520
tgaaataggg cctacaatca taaatgcaca ggactatatc cttgggtgat tctactctaa   2580
caccacatct caccttatttt agacatgcca aatgaaacac tctttgtgaa tttctgccga   2640
gatacaatct tggtgtctct ttttttaccca gatgtggacc agctagtgaa gtgctcccac   2700
gagcgctcca ttcatctctt catcgactct ctgttgaatg aagaaaatcc aagtaaggcc   2760
tacaggtgca gttccaagga agccttttgag aaagggctct gcttgagttg tagaaagaac   2820
cgctgcaaca atctgggcta tgagatcaat aaagtcagag ccaaaagaag cagcaaaatg   2880
tacctgaaga ctcgttctca gatgccctac aaaggtaggc tggagactgt tgtaaataag   2940
gaaaccaagg agtcctattt catcatgctc actgcatcac atgtactgat tctgtccatt   3000
ggaacagaga tgatgactgg tgttactaaa ccctgagccc tggtgtttct gttgataggg   3060
ggttgcattg atccatttgt ctgaggcttc taattcccat tgtcagcaag gtcccagtgc   3120
tcagtgtggg atttgcagcc ttgctcgctg ccctcccctg taaatgtggc cattaccatg   3180
ggctaggcta tcagcacaga gctcagagct catttggaac catccacctc gggtcaacaa   3240
```

```
actataaccc ttgtgccaaa tccagcctac ttcctgcttt tgtaaatagt ttttttaaaa    3300
cttttaagtt caggggtacg tatgtaggtt tgctaaaaag gtaaacttgt gacatgggag    3360
tttgttgtcc agaatattcc atcacccagg tattaagctt agtacccatt agttactttt    3420
cctgaagctc tccctcctcc caccctctgg gaggcccag tgtctgttgt tcccctctat     3480
gtgctcatgc aaagttttat taggacacag ccacacacat tcattaccat attgtcaaag    3540
gctggtttca tgccaccata acagagttga tagcccacag agcctaaaat atttactccc    3600
tggcccttta cagaatgttc acaacttaca taaaggcaag gaccatctgt cttatttatt    3660
tatttattta atttgagatg aagtctagct ttctcctagg ctggaggaga ggggcatgat    3720
cttggctcac cacaacctct gcctcccggg ttcaaatgat tcccctgcct cagcctccgg    3780
agtagctggg ataacaggca tgcaccatca tgcccagcta attttgtat ttttagtaga     3840 gagggggttt caccgtgttg accaggctgg tctcgaactg ctgacctcag gtgatctgcc    3900
ctccttggcc tcatctgtct ttttaaatgc aactattcct ggaaggcaag aatatctcac    3960
accttctaag atactgccat tttgccagga gtttgtttca cacttgaatt tcaagcttgg    4020
cctcttgttt agaggcagac ctaaaggaat ggtcggaaaa tgagagagga ggtcttcgga    4080
taaatccggt gagagggacc aacttcagga agggtggctt ttgtggaatc cagatggaaa    4140
cctgagggaa gggatgatat taaagaacag tggccccagg taaaacatat ggcacccatg    4200
tgtaaggtga ttcttagaat ctgtagaggt gtctttcgtg gtatagaggt tgaggcacct    4260
gtgcttcaag gaaaccttaa ctcttcaaaa tcaggcaatg cgtatgaggt aaagagagga    4320
ctgtgggacc ataatcttga agacacagac aggcttcact catccctgcc tcctgcacca    4380
gtgggttcaa ggctctgtca gtgtcccta ggggcacctc accactccca gcttcttcag     4440
ctctggcctg tcctgctgcc tgcaagggtt ttgcttaatt ctcaattcaa tgtctcttca    4500
tcttttagta gctgtggggt tttgttgttg ttccttctgtt tttgcttagt atctgactac    4560 ttttaatta taaaaagaga tgtatctaaa caaaatagag attgttatca gaagttcaca     4620
acatttatta aaaatttttt cacctggaca agagtctaaa gcagcataaa aatatggtct    4680
gctatattct aaaccatcag tcttaagaga tctgtgtctc agcttaagag aaaatacatt    4740
taatagacag taacacaaat aagaaaaaaa tctgaccaag gatagtggga tatagaagaa    4800
aaaacattcc aagaattatt ttatttattt atttatttat ttatttattt atttatttat    4860
ttttgagaca cggtctcgct cagttaccca ggctggagtg cagcggcgca atcttaactc    4920
actgcaacct ctgctttccg gttcaagcga ttctcctgcc tcagcctcct gagtaactgg    4980
gattacaggc acccgccacc acgcccaact aatttctgta ttttttcttag tagaaacagg   5040 gtttcaccat gttggccaag ctagtctcaa actcctgacc tcaggtgatt cacccaccaa    5100
ggcctcccaa agtgctggga ttacaggcat gagccaccat gcctggcctc caaaaactct    5160
tttttcctcc atcatcatgg ttctatttta gtcctgctgc ctttccttt aacctctccc     5220 caggcccatt tgctcagggt ttttggtaga ccagagga ggggcaggga ggagatatag      5280
aagttcaact acctgcttcc agaggctgtc cctagtatag aatactttag gggctggctt    5340
tacaaggcag tccttgtggc ctcactgatg gctcaatgaa ataagttctt ttttaaaaaa    5400 aatttttattt atttccatag gttattgggg gaacaggtgt tgtttggtta catgagtaag    5460
ttctttagta gtgatttgtg agattttggt gtgcccatta cggaatggaa aaatcaacga    5520
aataagttct atgatgcacc tactagacac ctaatctgca ctagatggtg ggggaattaa    5580
gagcatgggc atgatcctgt gaccggaagc ccgcttacag tcagggtgga ggacagacct    5640
```

```
actcatgaaa caaacacagt gacatatagt gacacagaag caaatgtcaa atatgcttgc   5700
tccagatgct aaggcacaag atggccaagg atggcggagt tcatggagaa agcatcatga   5760
gtgttttggc cttctgattt gatctcccta gcacccctca agatggcta cttcctaatg    5820 ctgcttggca attcagacac atttgggttt ttcctatgca tataaccaca cttttctgaa   5880
agggagtaga attcaaggtc tgcatttttct aggtatgaac actgtgcatg atgaagtctt  5940
tccaagccac accagtggtt ccatgtgtgt gcacttccgg tttgagtgct agtgagatac   6000
ttctgtggtt ctgaattgcc tgactatttg gggttgtgat attttcataa agattgatca   6060
acatgttcga atttcctccc caacagtctt ccattaccaa gtaaagattc attttctgg    6120 gactgagagt gaaacccata ccaatcaggc ctttgagatt tctctgtatg caccgtggc    6180 cgagagtgag aacatcccat tcactctgtg agtagcacag gggggcggtc atcatggcac   6240
cagtccctcc cctgccataa cccttggtct gagcagcaga agcagagagc gatgcctaga   6300
aaacaagtct ttagttaaaa aaatcagaat ttcaaaattg aggtctttcc tctatttgat   6360
attgagaaaa aaatgcttca aattggccat tttatttttca cttactagtt atattttttt  6420
atttatcatc ttatatctgt ttatttcttt tataaagctg ctgttaaaca atataattaa   6480
actatctcaa aaggtttgac attaaagaaa atgagcaatg gtaacaggaa accactctat   6540
agatgtacat ataatatgta cagaaaatat aagtagtaag aagtccatga caaagtgtta   6600 gctcttttt tttttttttt ttttttttt tttgagatgg agtctctctc ctattgccca    6660
ggctggagtg cagtgattcg atctcagctc actgcaacct ctacctcccg agttcaaaca   6720
attcttctgt ctcagcctcc cgagtagctg gggctgcagg tgcccaccac catgcccagc   6780 taattttgt attttagta gcgacagggt ctcaccatgt tggccaagct ggtcttgaat     6840
tcctgatctc aggtgatcca cccgcctcgg cctcccaaag tgctgggatt acaggtgtga   6900
gccaccatgc ccagcctacc ctttactact aatcaaagaa ataaaagtaa ggcaacttga   6960 tactttaca attactagat gaacaaatct ttaaaaatag ccagtgcaga caaggtggtg    7020
aagcagaaca tgcgaaccta ccatgcatca ttcacggcta gaaccctcca ggtgcggaag   7080
gtagtatttt aataactttc catagctaca aaatattatt acatagaagg gagtgatttt   7140
tttctaatat ttatcctaaa gaaatagtca acaaacattt ttaaaaaaca tcaattacag   7200
tcgtacctat actagcataa attagaaacc cagtatccaa cattgaggca gtgggtaaat   7260
gaatcgtggt ttatcaagtc attaaaatca atctagcctt taaaaactat aattgtagga   7320
aacccaggaa aacatagtaa aaaatggaat ataaaatcta aagagaataa agaatagaga   7380
atcgtatgtg tgctatgatt gtagctaaat aatgttcaag tatcaacaca aattgaaaag   7440
gaatacatga aaatgaaaat tatatttctg aatgattgac ttcaggatttt tcttttagaa  7500 ttgtattaaa tagttcatgt cattaggata aatgctggaa tgtggatata atttaaaata   7560
tactaaatgc catcgacctt cattttgagt tctttgttgg acattttgt gcattttta     7620 aatatcccct aaataataaa gctatttata tttggagagg agaaaaaaa gtgggggca     7680 gggagagctg atctctataa ctaaccaaat ttattgcttt tttgtttagg cctgaagtt    7740 ccacaaataa gacatactcc ttcctaattt acacagaggt agatattgga gaactactca   7800
tgttgaagct caaatggaag agtgattcat actttagctg gtcagactgg tggagcagtc   7860
ccggcttcgc cattcagaag atcagagtaa aagcaggaga gactcagaaa agtaattaa    7920 atgtattttt cttccttcac tttagacccc cacctgatgt caggacctag ggctgtatt    7980 tcaggggcct tcacaattca gggagagctt taggaaacct tgtatttatt actgtatgat   8040
```

```
gtagattttc tttaggagtc ttctttaatt ttcttatttt tggggggcgg gggggaagt    8100 gacagtattt ttgtatttca tgtaaggaaa acataagccc tgaatcgctc acagttattc    8160
agtgagagct gggattagaa gtcaggaatc tcagcttctc atttggcact gtttcttgta    8220
agtacaaaat agttagggaa caaacctccg agatgctacc tggataatca agattcaaa    8280 ccaacctctt caagaagggt gagattccaa gataatctca acctgtctcc gcagccccac    8340
ccatgtgtac ccataaaatg aattacacag agatcgctat aggatttaaa gcttttatac    8400
taaatgtgct gggattttgc aaactatagt gtgctgttat tgttaattta aaaaaactct    8460
aagttaggat tgacaaatta tttctcttta gtcatttgct tgtatcacca aagaagcaaa    8520
caaacaaaca aaaaaaaaaa gaaaagatc ttggggatgg aaatgttata agaatctttt    8580
tttacactag caatgtctag ctgaaggcag atgccctaat tccttaatgc agatgctaag    8640
agatggcaga gttgatcttt tatcatctct tggtgaaagc ccagtaacat aagactgctc    8700
taggctgtct gcatgcctgt ctatctaaat taactagctt ggttgctgaa caccgggtta    8760
ggctctcaaa ttaccctctg attctgatgt ggcctgagtg tgacagttaa ttattgggaa    8820
tatcaaaaca attacccagc atgatcatgt attatttaaa cagtcctgac agaactgtac    8880
ctttgtgaac agtgctttg attgttctac atggcatatt cacatccatt tcttccaca    8940 gggtgatctt ctgttctagg gagaaagtgt ctcatttgca gaaaggaaag gcacctgcgg    9000
tatttgtgaa atgccatgac aagtctctga ataagaagtc aggctggtga gcattctggg    9060
ctaaagctga ctgggcatcc tgagcttgca ccctaaggga ggcagcttca tgcattcctc    9120
ttcaccccat caccagcagc ttgccctgac tcatgtgatc aaagcattca atcagtcttt    9180
cttagtcctt ctgcatatgt atcaaatggg tctgttgctt tatgcaatac ttcctctttt    9240
tttctttctc ctcttgtttc tcccagcccg gaccttcaac ccaggcacac attttaggtt    9300
ttattttact ccttgaacta cccctgaatc ttcacttctc cttttttctc tactgcgtct    9360
ctgctgactt tgcagatgcc atctgcagag catgtaacac aagtttagta gttcccgttc    9420
tggctgtggg tgcagctctt cccaggatgt attcagggaa gtaaaaagat ctcactgcat    9480
cacctgcagc cacatagttc ttgattctcc aagtgccagc atactccggg acacacagcc    9540
aacagggctg ccccaagcac ccatctcaaa accctcaaag ctgccaagca acagaatga    9600 gagttatagg aaactgttct ctcttctatc tccaaacaac tctgtgcctc tttcctacct    9660
gacctttagg gctaatccat gtggcagctg ttagctgcat cttttccagag cgtcagtact    9720 gagaggacac taag                                                     9734

<210> SEQ ID NO 26
<211> LENGTH: 20
<212> TYPE: DNA
<213> ORGANISM: Artificial
<220> FEATURE:
<223> OTHER INFORMATION: forward primer

<400> SEQUENCE: 26
caggcgggaa ttgtaaaaca                                                 20

<210> SEQ ID NO 27
<211> LENGTH: 20
<212> TYPE: DNA
<213> ORGANISM: Artificial
<220> FEATURE:
<223> OTHER INFORMATION: reverse primer

<400> SEQUENCE: 27
```
ttgacgtctg gaccacattc                                        20

<210> SEQ ID NO 28
<211> LENGTH: 20
<212> TYPE: DNA
<213> ORGANISM: Artificial
<220> FEATURE:
<223> OTHER INFORMATION: forward primer

<400> SEQUENCE: 28
ctggatcttt cggactgagg                                        20

<210> SEQ ID NO 29
<211> LENGTH: 20
<212> TYPE: DNA
<213> ORGANISM: Artificial
<220> FEATURE:
<223> OTHER INFORMATION: reverse primer

<400> SEQUENCE: 29
caggaacctc tccacccttt                                        20

<210> SEQ ID NO 30
<211> LENGTH: 21
<212> TYPE: DNA
<213> ORGANISM: Artificial
<220> FEATURE:
<223> OTHER INFORMATION: forward primer

<400> SEQUENCE: 30
ttccagtgcg tctcttttgt t                                      21

<210> SEQ ID NO 31
<211> LENGTH: 20
<212> TYPE: DNA
<213> ORGANISM: Artificial
<220> FEATURE:
<223> OTHER INFORMATION: reverse primer

<400> SEQUENCE: 31
attccaagcc tgatgatgtt                                        20

<210> SEQ ID NO 32
<211> LENGTH: 20
<212> TYPE: DNA
<213> ORGANISM: Artificial
<220> FEATURE:
<223> OTHER INFORMATION: forward primer

<400> SEQUENCE: 32
ttgttcctga tgtgccagaa                                        20

<210> SEQ ID NO 33
<211> LENGTH: 24
<212> TYPE: DNA
<213> ORGANISM: Artificial
<220> FEATURE:
<223> OTHER INFORMATION: reverse primer

<400> SEQUENCE: 33
tgctgagtga atctgaccta agaa                                   24

<210> SEQ ID NO 34
<211> LENGTH: 21
<212> TYPE: DNA
<213> ORGANISM: Artificial

```
<220> FEATURE:
<223> OTHER INFORMATION: forward primer

<400> SEQUENCE: 34
caggcgggaa ttgtaaaaca c                                         21

<210> SEQ ID NO 35
<211> LENGTH: 23
<212> TYPE: DNA
<213> ORGANISM: Artificial
<220> FEATURE:
<223> OTHER INFORMATION: reverse primer

<400> SEQUENCE: 35
ttgttctgta gattcgccca gtt                                       23

<210> SEQ ID NO 36
<211> LENGTH: 27
<212> TYPE: DNA
<213> ORGANISM: Artificial
<220> FEATURE:
<223> OTHER INFORMATION: Forward primer

<400> SEQUENCE: 36
cactcagaag ataataaatt gcccttt                                   27

<210> SEQ ID NO 37
<211> LENGTH: 22
<212> TYPE: DNA
<213> ORGANISM: Artificial
<220> FEATURE:
<223> OTHER INFORMATION: Reverse primer

<400> SEQUENCE: 37
cacatgccgt tctttgttct gt                                        22

<210> SEQ ID NO 38
<211> LENGTH: 18
<212> TYPE: DNA
<213> ORGANISM: Artificial
<220> FEATURE:
<223> OTHER INFORMATION: Forward primer

<400> SEQUENCE: 38
ggcgtattgg gccatagc                                             18

<210> SEQ ID NO 39
<211> LENGTH: 21
<212> TYPE: DNA
<213> ORGANISM: Artificial
<220> FEATURE:
<223> OTHER INFORMATION: Reverse primer

<400> SEQUENCE: 39
aaggcctcag tccgaaagat c                                         21

<210> SEQ ID NO 40
<211> LENGTH: 21
<212> TYPE: DNA
<213> ORGANISM: Artificial
<220> FEATURE:
<223> OTHER INFORMATION: Forward primer

<400> SEQUENCE: 40
ttgaaaatga gcctgtaatc c                                         21
```

```
<210> SEQ ID NO 41
<211> LENGTH: 20
<212> TYPE: DNA
<213> ORGANISM: Artificial
<220> FEATURE:
<223> OTHER INFORMATION: Reverse primer

<400> SEQUENCE: 41 tttttctgc accattcaaa                                                    20

<210> SEQ ID NO 42
<211> LENGTH: 25
<212> TYPE: DNA
<213> ORGANISM: Artificial
<220> FEATURE:
<223> OTHER INFORMATION: Forward primer

<400> SEQUENCE: 42
acacataatt tgaatggtgc agaaa                                             25

<210> SEQ ID NO 43
<211> LENGTH: 30
<212> TYPE: DNA
<213> ORGANISM: Artificial
<220> FEATURE:
<223> OTHER INFORMATION: Reverse primer

<400> SEQUENCE: 43
tcagatattg aatgatttta aattgatgaa                                        30

<210> SEQ ID NO 44
<211> LENGTH: 22
<212> TYPE: DNA
<213> ORGANISM: Artificial
<220> FEATURE:
<223> OTHER INFORMATION: Forward primer

<400> SEQUENCE: 44
caatgagcca gatggagtac ca                                                22

<210> SEQ ID NO 45
<211> LENGTH: 31
<212> TYPE: DNA
<213> ORGANISM: Artificial
<220> FEATURE:
<223> OTHER INFORMATION: Reverse primer

<400> SEQUENCE: 45
gttcactcac tcttgattag ttgttaaaaa c                                      31

<210> SEQ ID NO 46
<211> LENGTH: 31
<212> TYPE: DNA
<213> ORGANISM: Artificial
<220> FEATURE:
<223> OTHER INFORMATION: Forward primer

<400> SEQUENCE: 46
caactaatca agagtgagtg aacaactatt t                                      31

<210> SEQ ID NO 47
<211> LENGTH: 36
<212> TYPE: DNA
<213> ORGANISM: Artificial
<220> FEATURE:
<223> OTHER INFORMATION: Reverse primer

<400> SEQUENCE: 47
```

```
gagatatttg acatctttat catttcatat ttatac                                36
```

<210> SEQ ID NO 48
<211> LENGTH: 28
<212> TYPE: DNA
<213> ORGANISM: Artificial
<220> FEATURE:
<223> OTHER INFORMATION: Forward primer

<400> SEQUENCE: 48

```
cctattttc agaatgctct tctacgta                                          28
```

<210> SEQ ID NO 49
<211> LENGTH: 21
<212> TYPE: DNA
<213> ORGANISM: Artificial
<220> FEATURE:
<223> OTHER INFORMATION: Reverse primer

<400> SEQUENCE: 49

```
agtcgggttc ccagctatag c                                                21
```

<210> SEQ ID NO 50
<211> LENGTH: 22
<212> TYPE: DNA
<213> ORGANISM: Artificial
<220> FEATURE:
<223> OTHER INFORMATION: Forward primer

<400> SEQUENCE: 50

```
cagcacatag cactgggaac tc                                               22
```

<210> SEQ ID NO 51
<211> LENGTH: 23
<212> TYPE: DNA
<213> ORGANISM: Artificial
<220> FEATURE:
<223> OTHER INFORMATION: Reverse primer

<400> SEQUENCE: 51

```
agctccattt acacatccac aca                                              23
```

<210> SEQ ID NO 52
<211> LENGTH: 30
<212> TYPE: DNA
<213> ORGANISM: Artificial
<220> FEATURE:
<223> OTHER INFORMATION: Forward primer

<400> SEQUENCE: 52

```
atgttctggc tttacatttt atttattagc                                       30
```

<210> SEQ ID NO 53
<211> LENGTH: 23
<212> TYPE: DNA
<213> ORGANISM: Artificial
<220> FEATURE:
<223> OTHER INFORMATION: Reverse primer

<400> SEQUENCE: 53

```
gccacaatga cctttccaat atg                                              23
```

<210> SEQ ID NO 54
<211> LENGTH: 23
<212> TYPE: DNA
<213> ORGANISM: Artificial

```
<220> FEATURE:
<223> OTHER INFORMATION: Forward primer

<400> SEQUENCE: 54
ggtcattgtg gctatctgca ttt                                             23

<210> SEQ ID NO 55
<211> LENGTH: 25
<212> TYPE: DNA
<213> ORGANISM: Artificial
<220> FEATURE:
<223> OTHER INFORMATION: Reverse primer

<400> SEQUENCE: 55
gctctgtgag accatcactg ataaa                                           25

<210> SEQ ID NO 56
<211> LENGTH: 26
<212> TYPE: DNA
<213> ORGANISM: Artificial
<220> FEATURE:
<223> OTHER INFORMATION: Forward primer

<400> SEQUENCE: 56
gtgtctttat cagtgatggt ctcaca                                          26

<210> SEQ ID NO 57
<211> LENGTH: 24
<212> TYPE: DNA
<213> ORGANISM: Artificial
<220> FEATURE:
<223> OTHER INFORMATION: Reverse primer

<400> SEQUENCE: 57
ttctgttttg ttaaagccca tttc                                            24

<210> SEQ ID NO 58
<211> LENGTH: 26
<212> TYPE: DNA
<213> ORGANISM: Artificial
<220> FEATURE:
<223> OTHER INFORMATION: Forward primer

<400> SEQUENCE: 58
gtgtctttat cagtgatggt ctcaca                                          26

<210> SEQ ID NO 59
<211> LENGTH: 25
<212> TYPE: DNA
<213> ORGANISM: Artificial
<220> FEATURE:
<223> OTHER INFORMATION: Reverse primer

<400> SEQUENCE: 59
ctttcttgtt ttgttaaagc ccatt                                           25

<210> SEQ ID NO 60
<211> LENGTH: 18
<212> TYPE: DNA
<213> ORGANISM: Artificial
<220> FEATURE:
<223> OTHER INFORMATION: probe

<400> SEQUENCE: 60
ctgagaaaaa gcacagga                                                   18
```

<210> SEQ ID NO 61
<211> LENGTH: 18
<212> TYPE: DNA
<213> ORGANISM: Artificial
<220> FEATURE:
<223> OTHER INFORMATION: probe

<400> SEQUENCE: 61
tgagaaaaaa cacaggaa                                                 18

<210> SEQ ID NO 62
<211> LENGTH: 14
<212> TYPE: DNA
<213> ORGANISM: Artificial
<220> FEATURE:
<223> OTHER INFORMATION: probe

<400> SEQUENCE: 62
aaactgggcg aatc                                                     14

<210> SEQ ID NO 63
<211> LENGTH: 14
<212> TYPE: DNA
<213> ORGANISM: Artificial
<220> FEATURE:
<223> OTHER INFORMATION: probe

<400> SEQUENCE: 63
aaactgggca aatc                                                     14

<210> SEQ ID NO 64
<211> LENGTH: 15
<212> TYPE: DNA
<213> ORGANISM: Artificial
<220> FEATURE:
<223> OTHER INFORMATION: probe

<400> SEQUENCE: 64
cagaattcca attaa                                                    15

<210> SEQ ID NO 65
<211> LENGTH: 17
<212> TYPE: DNA
<213> ORGANISM: Artificial
<220> FEATURE:
<223> OTHER INFORMATION: probe

<400> SEQUENCE: 65
ccatgaattc cagttaa                                                  17

<210> SEQ ID NO 66
<211> LENGTH: 14
<212> TYPE: DNA
<213> ORGANISM: Artificial
<220> FEATURE:
<223> OTHER INFORMATION: probe

<400> SEQUENCE: 66
tcagctgaca cata                                                     14

<210> SEQ ID NO 67
<211> LENGTH: 14
<212> TYPE: DNA
<213> ORGANISM: Artificial
<220> FEATURE:
<223> OTHER INFORMATION: probe

<400> SEQUENCE: 67

-continued tcagctgaca cgta                                             14

<210> SEQ ID NO 68
<211> LENGTH: 17
<212> TYPE: DNA
<213> ORGANISM: Artificial
<220> FEATURE:
<223> OTHER INFORMATION: probe

<400> SEQUENCE: 68
tagattctcc aaatgat                                          17

<210> SEQ ID NO 69
<211> LENGTH: 20
<212> TYPE: DNA
<213> ORGANISM: Artificial
<220> FEATURE:
<223> OTHER INFORMATION: probe

<400> SEQUENCE: 69
attagattct ctaaatgatt                                       20

<210> SEQ ID NO 70
<211> LENGTH: 16
<212> TYPE: DNA
<213> ORGANISM: Artificial
<220> FEATURE:
<223> OTHER INFORMATION: probe

<400> SEQUENCE: 70
aacaaatagc aaccct                                           16

<210> SEQ ID NO 71
<211> LENGTH: 17
<212> TYPE: DNA
<213> ORGANISM: Artificial
<220> FEATURE:
<223> OTHER INFORMATION: probe

<400> SEQUENCE: 71
aacaaataac aaccctc                                          17

<210> SEQ ID NO 72
<211> LENGTH: 16
<212> TYPE: DNA
<213> ORGANISM: Artificial
<220> FEATURE:
<223> OTHER INFORMATION: probe

<400> SEQUENCE: 72
agaatgctct tctacg                                           16

<210> SEQ ID NO 73
<211> LENGTH: 17
<212> TYPE: DNA
<213> ORGANISM: Artificial
<220> FEATURE:
<223> OTHER INFORMATION: probe

<400> SEQUENCE: 73
cagaatgctc ttatacg                                          17

<210> SEQ ID NO 74
<211> LENGTH: 19
<212> TYPE: DNA
<213> ORGANISM: Artificial

```
<220> FEATURE:
<223> OTHER INFORMATION: probe

<400> SEQUENCE: 74
tgataaagat gtcaaatat                                                19

<210> SEQ ID NO 75
<211> LENGTH: 17
<212> TYPE: DNA
<213> ORGANISM: Artificial
<220> FEATURE:
<223> OTHER INFORMATION: probe

<400> SEQUENCE: 75
ataaaggtgt caaatat                                                  17

<210> SEQ ID NO 76
<211> LENGTH: 20
<212> TYPE: DNA
<213> ORGANISM: Artificial
<220> FEATURE:
<223> OTHER INFORMATION: probe

<400> SEQUENCE: 76
ctccgaaaaa ctttgttata                                               20

<210> SEQ ID NO 77
<211> LENGTH: 19
<212> TYPE: DNA
<213> ORGANISM: Artificial
<220> FEATURE:
<223> OTHER INFORMATION: probe

<400> SEQUENCE: 77
tccgaaaaac tttgctata                                                19

<210> SEQ ID NO 78
<211> LENGTH: 16
<212> TYPE: DNA
<213> ORGANISM: Artificial
<220> FEATURE:
<223> OTHER INFORMATION: probe

<400> SEQUENCE: 78
caagctccat ttacac                                                   16

<210> SEQ ID NO 79
<211> LENGTH: 15
<212> TYPE: DNA
<213> ORGANISM: Artificial
<220> FEATURE:
<223> OTHER INFORMATION: probe

<400> SEQUENCE: 79
caagctccgt ttaca                                                    15

<210> SEQ ID NO 80
<211> LENGTH: 18
<212> TYPE: DNA
<213> ORGANISM: Artificial
<220> FEATURE:
<223> OTHER INFORMATION: probe

<400> SEQUENCE: 80
acacatacag ttagcacc                                                 18
```

```
<210> SEQ ID NO 81
<211> LENGTH: 18
<212> TYPE: DNA
<213> ORGANISM: Artificial
<220> FEATURE:
<223> OTHER INFORMATION: probe

<400> SEQUENCE: 81
acacatacaa agttagca                                                 18

<210> SEQ ID NO 82
<211> LENGTH: 16
<212> TYPE: DNA
<213> ORGANISM: Artificial
<220> FEATURE:
<223> OTHER INFORMATION: probe

<400> SEQUENCE: 82
ccaactcact cttatg                                                   16

<210> SEQ ID NO 83
<211> LENGTH: 17
<212> TYPE: DNA
<213> ORGANISM: Artificial
<220> FEATURE:
<223> OTHER INFORMATION: probe

<400> SEQUENCE: 83
agccaactta ctcttat                                                  17

<210> SEQ ID NO 84
<211> LENGTH: 16
<212> TYPE: DNA
<213> ORGANISM: Artificial
<220> FEATURE:
<223> OTHER INFORMATION: probe

<400> SEQUENCE: 84
ccaactcaat cttatg                                                   16

<210> SEQ ID NO 85
<211> LENGTH: 17
<212> TYPE: DNA
<213> ORGANISM: Artificial
<220> FEATURE:
<223> OTHER INFORMATION: probe

<400> SEQUENCE: 85
agccaactta atcttat                                                  17
```